(12) United States Patent
Russell et al.

(10) Patent No.: US 8,591,933 B2
(45) Date of Patent: *Nov. 26, 2013

(54) TEMPORAL RELEASE OF GROWTH FACTORS FROM 3D MICRO ROD SCAFFOLDS FOR TISSUE REGENERATION

(75) Inventors: Brenda Russell, Evanston, IL (US); Tejal A. Desai, San Francisco, CA (US); Paul Goldspink, Northfield, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 423 days.

This patent is subject to a terminal disclaimer.

(21) Appl. No.: 12/689,906

(22) Filed: Jan. 19, 2010

(65) Prior Publication Data
US 2010/0158979 A1   Jun. 24, 2010

Related U.S. Application Data

(63) Continuation-in-part of application No. PCT/US2008/070471, filed on Jul. 18, 2008.

(60) Provisional application No. 60/950,454, filed on Jul. 18, 2007, provisional application No. 61/179,584, filed on May 19, 2009.

(51) Int. Cl.
| A61F 2/00 | (2006.01) |
| A61K 31/74 | (2006.01) |
| A61K 38/00 | (2006.01) |

(52) U.S. Cl.
USPC ................. 424/423; 424/78.08; 514/12.1

(58) Field of Classification Search
None
See application file for complete search history.

(56) References Cited

U.S. PATENT DOCUMENTS

| 5,868,745 | A | 2/1999 | Alleyne |
| 5,916,597 | A | 6/1999 | Lee et al. |
| 6,106,558 | A | 8/2000 | Picha |
| 6,214,618 | B1 | 4/2001 | Hillegas et al. |
| 6,221,109 | B1 | 4/2001 | Geistlich et al. |
| 6,328,990 | B1 | 12/2001 | Ducheyne et al. |
| 6,398,819 | B1 | 6/2002 | Bell |
| 6,423,092 | B2 | 7/2002 | Datta et al. |
| 6,461,640 | B1 | 10/2002 | Hubbell et al. |
| 6,531,146 | B2 | 3/2003 | Calhoun et al. |
| 6,548,728 | B1 | 4/2003 | Faries et al. |
| 6,572,878 | B1 | 6/2003 | Blaine |
| 6,942,873 | B2 | 9/2005 | Russell et al. |
| 6,967,086 | B2 | 11/2005 | Guarine et al. |
| 7,273,620 | B1 | 9/2007 | Zhigaltsev et al. |
| 7,790,456 | B2 | 9/2010 | Terstegge et al. |

(Continued)

FOREIGN PATENT DOCUMENTS

| WO | WO-2006/053836 | 5/2006 |
| WO | WO-2007/073035 | 6/2007 |

OTHER PUBLICATIONS

Leary Swan et al. J Biomed Mater Res 72A: 288-295 (2005).*
Sung et al., Biomaterials 26: 4557-4567 (2005).*

(Continued)

*Primary Examiner* — Abigail Fisher
*Assistant Examiner* — Thor Nielsen
(74) *Attorney, Agent, or Firm* — Marshall, Gerstein & Borun LLP

(57) ABSTRACT

The present invention relates to the use of three-dimensional microrod scaffolds for the temporal release of growth factors useful in tissue regeneration, engineering and treatment of disorders.

35 Claims, 22 Drawing Sheets

(56) References Cited

U.S. PATENT DOCUMENTS

| | | |
|---|---|---|
| 2003/0078588 A1 | 4/2003 | Alleyne |
| 2004/0018149 A1 | 1/2004 | Noll et al. |
| 2004/0137033 A1 | 7/2004 | Calhoun et al. |
| 2007/0249044 A1 | 10/2007 | Desai et al. |

OTHER PUBLICATIONS

Thacharodi et al., Int J Pharmaceutics 120: 115-118 (1995).*
Alberts et al., Cell junctions, cell adhesions, and the extracellular matrix. In: Molecular Biology of the Cell. New York: Garland Publishing, Chapter 19, 950-1006 (1994).
Albrecht et al., Photo- and electropatterning of hydrogel-encapsulated living cell arrays, *Lab Chip*, 5: 111-8 (2005).
Anderson et al., Biodegradation and biocompatibility of PLA and PlGA microspheres, *Adv. Drug Del. Rev.*, 28: 5-24 (1997).
Angst et al., Dissociated spatial patterning of gap junctions and cell adhesion junctions during postnatal differentiation of ventricular myocardium, *Circ. Res.*, 80: 88-94 (1997).
Arshady, Preparation of biodegradable microspheres and microcapsules: Polyactides and related polyesters, *J. Controlled Rel.*, 17:1-22 (1991).
Asakura et al., Side population cells from diverse adult tissues are capable of in vitro hematopoietic differentiation, *Exp. Hematol.*, 30(11): 1339-45 (2002).
Black et al., Photocarcinogenesis: an overview, *J. Photochem. Photobiol.*, 40: 29-47 (1997).
Bloch et al., Lateral force transmission across costameres in skeletal muscle, *Exerc. Sport Sci. Rev.*, 31(2): 73-8 (2003).
Boateng et al., Inhibition of fibroblast proliferation in cardiac myocyte cultures by surface microtopography, *Am. J. Physiol. Cell Physiol.*, 285: C171-82 (2003).
Boheler et al., Differentiation of pluripotent embryonic stem cells into cardiomyocytes, *Circ. Res.*, 91: 189-201 (2002).
Boheler et al., ES cell differentiation to the Cardiac Lineage. In Methods in Enzymology. Editors: P.M. Wassarman and G.M. Keller, vol. 365, Chapter 16, pp. 228-241 (2003).
Bryant et al., Cytocompatibility of UV and visible light photoinitiating systems on cultured NIH/3T3 fibroblasts in vitro, *J. Biomater. Sci. Polymer Ed.*, 11: 439-57 (2000).
Buerke et al., Cardioprotective effect of insulin-like growth factor I in myocardial ischemia followed by reperfusion, *Proc. Natl. Acad. Sci. USA*, 92: 8031-5 (1995).
Cascone et al., Collagen and hyaluronic acid based polymeric blends as drug delivery systems for the release of physiological concentrations of growth hormone, *J. Mater. Sci.*, 5: 770-4 (1994).
Caspi et al., Potential applications of human embryonic stem cell-derived cardiomyocytes, *Ann. NY Acad. Sci.*, 1015: 285-98 (2004).
Cheng et al., Programmed myocyte cell death affects the viable myocardium after infarction in rats, *Exp. Cell Res.*, 226: 316-27 (1996).
Chicurel et al., Cellular control lies in the balance of forces, *Curr. Opin. Cell Biol.*, 10(2): 232-9 (1998).
Chicurel et al., Integrin binding and mechanical tension induce movement of mRNA and ribosomes to focal adhesions, *Nature*, 392(6677): 730-3 (1998).
Cohen et al., Controlled delivery systems for proteins based on poly(lactic/glycolic acid) microspheres, *Pharmacol. Res.*, 8: 713-20 (1991).
Cooper et al., Load regulation of the properties of adult feline cardiocytes. The role of substrate adhesion, *Circ. Res.*, 58: 692-705 (1986).
Crotts et al., Protein delivery from poly(lactic-co-glycolic acid) biodegradable microspheres: Release kinetics and stability issues, *J. Microencapsul.*, 15: 699-713 (1998).
Cukierman et al., Taking cell-matrix adhesions to the third dimension, *Science*, 294: 1708-12 (2001).
Davis et al., Local myocardial insulin-like growth factor 1 (IGF-1) delivery with biotinylated peptide nanofibers improves cell therapy for myocardial infarction, *Proc. Natl. Acad. Sci. USA*, 103(21): 8155-60 (1996).

Deutsch et al., Fabrication of microtextured membranes for cardiac myocyte attachment and orientation, *J. Biomed. Mater. Res.*, 53: 267-75 (2000).
Deutsch-Snyder et al., Fabrication of multiple microscale features on polymer surfaces for applications in tissue engineering, *J. Biomat. Sci. Polymer Ed.*, 3: 293-300 (2001).
Dluzniewska et al., A strong neuroprotective effect of the autonomous C-terminal peptide of IGF-1 Ec (MGF) in brain ischemia, *FASEB J.*, 19(13): 1896-8 (2005).
Duerr et al., Cardiovascular effects of insulin-like growth factor-1 and growth hormone in chronic left ventricular failure in the rat, *Circulation*, 93(12): 2188-96 (1996).
Dunn et al., Synthesis of N-(aminoalkyl) chitosan for microcapsules, *J. Appl. Polymer Sci.*, 50: 353-65 (1993).
Edelman et al., Controlled and modulated release of basic fibroblast growth factor, *Biomaterials*, 12: 619-26 (1991).
Ehler et al., Human foetal lung (IMG-90) cells: Myofibroblasts with smooth muscle-like contractile properties, *Cell Mot. Cytoskel.*, 34: 288-98 (1996).
Engler et al., Matrix elasticity directs stem cell lineage specification, *Cell*, 126(4): 677-89 (2006).
Engler et al., Myotubes differentiate optimally on substrates with tissue-like stiffness: Pathological implications for soft or stiff microenvironments, *J. Cell Biol.*, 166(6): 877-87 (2004).
Ennett et al., Temporally regulated delivery of VEGF in vitro and in vivo, *J. Biomed. Mater. Res. A.*, 79(1): 176-84 (2006).
Fawcett et al., Blood lymph vascular systems. In: Textbook of Histology. Philadelphia, PA: W.B. Saunders, pp. 367-400 (1986).
Fazal et al., Inhibiting myosin light chain kinase induces apoptosis in vitro and in vivo, *Mol Cell Biol.*, 25(14): 6259-66 (2005).
Fazel et al., Cardioprotective c-kit+ cells are from the bone marrow and regulate the myocardial balance of angiogenic cytokines, *J. Clin. Invest.*, 116(7): 1865-77 (2006).
Fazio et al., A preliminary study of growth hormone in the treatment of dilated cardiomyopathy, *N. Engl. J. Med.*, 334(13): 809-14 (1993).
Fishman et al., Expression of connexin43 in the developing rat heart, *Circ Res.*, 68: 782-7 (1991).
Folch et al., Microengineering of cellular interactions, *Annu. Rev. Biomed. Eng.*, 2: 227-56 (2000).
Foyt et al., Differential association of insulin-like growth factor I mRNA variants with polysomes in vivo, *J. Biol. Chem.*, 266(11): 7300-5 (1991).
Fu et al., Crucial role of the sarcoplasmic reticulum in the developmental regulation of $Ca^{2+}$ transients and contraction in cardiomyocytes derived from embryonic stem cells, *FASEB J.*, 20(1): 181-3 (2006).
Georges et al., Matrices with compliance comparable to that of brain tissue select neuronal over glial growth in mixed cortical cultures, *Biophys. J.*, 90: 3012-8 (2006).
Ghosh et al., Cell adaptation to a physiologically relevant ECM mimic with different viscoelastic properties, *Biomaterials*, 289: 671-9 (2007).
Goessl et al., Control of shape and size of vascular smooth muscle cells in vitro by plasma lithography, *J. Biomed. Mater. Res.*, 57: 15-24 (2001).
Goldspink et al., Protein kinase Cε over-expression alters myofilament properties and composition during the progression of heart failure, *Circ. Res.*, 95(4): 424-32 (2004).
Goldspink, Impairment of IGF-I gene splicing and MGF expression associated with muscle wasting, *Int. J. Biochem. Cell Biol.*, 37: 2012-22 (2005).
Gray et al., Repositioning of cells by mechanotaxis on surfaces with micropatterned Young's modulus, *J. Biomed. Mater. Res. A.*, 66(3): 605-14 (2003).
Grish et al., Affordable image analysis using NIH Image/Image, *Indian J. Cancer*, 41: 47 (2004).
Grossman et al., Wall stress and patterns of hypertrophy in the human left ventricle, *J. Clin. Invest.*, 56: 56-64 (1975).
Gumbiner, Cell adhesion: the molecular basis of tissue architecture and morphogenesis, *Cell*, 84: 345-57 (1996).
Hahn et al., Three-dimensional biochemical and biomechanical patterning of hydrogels for guiding cell behavior, *Adv. Mater.*, 18: 2679-84 (2006).

(56) References Cited

OTHER PUBLICATIONS

Hardikar et al., Hepatobiliary function. In: Medical Physiology. Philadelphia, PA: W.B. Saunders, Chapter 45, pp. 975-1002 (2003).
Helary et al., Fibroblast populated dense collagen matrices: cell migration, cell density, and metalloproteinases expression, *Biomaterials*, 26: 1533-43 (2005).
Holland et al., Polymers for biodegradable medical devices: the potential of polyesters as controlled macromolecular release systems, *J. Controlled Rel.*, 4: 155-80 (1986).
Holmes et al., Structure and mechanics of healing myocardial infarcts, *Annu. Rev. Biomed. Eng.*, 7: 223-53 (2005).
Hossenlopp et al., Characterization of epoxy resin (SU-8) film using thickness-shear mode (TSM) resonator under various conditions, *J. Polymer Sci.: Polymer Phys.*, 42: 2373-84 (2004).
Huang et al., The structural and mechanical complexity of cell-growth control, *Nat. Cell Biol.*, 1(5): E131-8 (1991).
Ingber et al., Mechanical control of tissue morphogenesis during embryological development, *Int. J. Dev. Biol,.* 50(2-3): 255-66 (2006).
Ingber et al., Neoplastic disorganization of pancreatic epithelial cell-cell relations. Role of basement membrane, *Am. J. Pathol.*, 121(2): 248-60 (1985).
Ingber, Cellular mechanotransduction: Putting all the pieces together again, *FASEB J.*, 20: 811-27 (2006).
Ingber, Mechanobiology and diseases of mechanotransduction, *Ann. Med.*, 35(8): 564-77 (2003).
Ingber, Tensegrity I. Cell structure and hierarchical systems biology, *J. Cell Sci.*, 116: 1157-73 (2003).
Jain et al., The manufacturing techniques of various drug loaded biodegradable poly(lactide-co-glycolide) (PLGA) devices, *Biomaterials*, 21: 2475-90 (2000).
Kajstura et al., Apoptotic and necrotic myocyte cell deaths are independent contributing variables of infarct size in rats, *Lab Invest.*, 74(1): 86-107 (1996).
Kelly et al., The anterior heart-forming field: voyage to the arterial pole of the heart, *Trends Genet.*, 18(4): 210-6 (2002).
Khetani et al., Exploring interactions between rat hepatocytes and nonparenchymal cells using gene expression profiling, *Hepatology*, 40: 545-54 (2004).
Kim et al., Control of degredation rate and hydrophilicity in electrospun non-woven poly (D,L-lactide) nanofiber scaffolds for biomedical applications, *Biomaterials*, 24(27):4977-85 (2003).
Kimura et al., Time course of de novo adipogenesis in matrigel by gelatin microspheres incorporating basic fibroblast growth factor, *Tissue Eng.*, 8(4): 603-13 (2002).
Krieg et al., Tensile forces govern germ-layer organization in zebrafish, *Nat. Cell Biol.*, 10(4): 429-36 (2008).
Kumar et al., Distinct signaling pathways are activated in response to mechanical stress applied axially and transversely to skeletal muscle fibers, *J. Biol. Chem.*, 277(48): 46493-503 (2002).
Kumar et al., Distinct mouse coronary anatomy and myocardial infarction consequent to ligation, *Coron. Artery Dis.*, 16(1): 41-4 (2005).
Kurihara et al., Cell adhesion ability of artificial extracellular matrix proteins containing a long repetitive Arg-Gly-Asp sequence,*J. Biosci. Bioeng.*, 100: 82-7 (2005).
Kurpinski et al., Anisotropic mechanosensing by mesenchymal stem cells, *Proc. Natl. Acad. Sci. USA*, 103(44): 16095-100 (2006).
Langer, Drug delivery and targeting,*Nature*, 392(6679): 5-10 (1998).
Langer, Tissue engineering, *Science*, 260(5110): 920-6 (1993).
Lee et al., Controlled growth factor release from synthetic extracellular matrices, *Nature*, 408: 998-1000 (2000).
Lele et al., Force meets chemistry: analysis of mechanochemical conversion in focal adhesions using fluorescence recovery after photobleaching, *J. Cell Biochem.*, 97: 1175-83 (2006).
Lele et al., Mechanical forces alter zyxin unbinding kinetics within focal adhesions of living cells, *J. Cell Physiol.*, 207(1): 187-94 (2006).

Lemaire et al., Structural modeling of drug release from biodegradable porous matrices based on a combined diffusion/erosion process, *Int. J. Pharm.*, 258: 95-107 (2003).
Li et al., Biology on a chip: microfabrication for studying the behavior of cultured cells, *Crit. Rev. Biomed. Eng.*, 31: 423-88 (2003).
Li et al., Overexpression of insulin-like growth factor I in mice protects from myocyte death after infarction, attenuating ventricular dilation, wall stress, and cardiac hypertrophy, *J. Clin. Invest.*, 100: 1991-9 (1997).
Lo et al., Cell movement is guided by the rigidity of the substrate, *Biophys. J.*, 79(1): 144-52 (2000).
Mahoney et al., Millimeter-scale positioning of a nerve-growth-factor source and biological activity in the brain, *Proc. Natl. Acad. Sci. USA*, 96: 4536-9 (1999).
Mansour et al., Restoration of resting sarcomere length after uniaxial static strain is regulated by protein kinase Cepsilon and focal adhesion kinase, *Circ. Res.*, 94(5): 642-9 (2004).
Mata et al., Characterization of polydimethylsiloxane (PDMS) properties for biomedical micro/nanosystems, *Biomed. Microdevices*, 7: 281-93 (2005).
Matthews et al., Changes in IGFs in cardiac tissue following myocardial infarction, *J. Endocrinol.*, 163(3): 433-45 (1999).
McKoy et al., Expression of insulin growth factor-1 splice variants and structural genes in rabbit skeletal muscle induced by stretch and stimulation, *J. Physiol.*, 516: 583-92 (1999).
Miller et al., Laser-scanning lithography (LSL) for the soft lithographic patterning of cell-adhesive self-assembled monolayers, *Biotechnol. Bioeng.*, 93: 1060-8 (2006).
Miyazaki et al., Drug release from oral mucosal adhesive tablets of chitosan and sodium alginate, *Int. J. Pharm.*, 118: 257-63 (1995).
Motlagh et al., Microfabricated grooves recapitulate neonatal myocyte connexin43 and N-cadherin expression and localization, *J. Biomed. Mater. Res.*, 67A: 148-57 (2003).
Motlaugh, Microtextured substrata alter gene expression, protein localization, and the shape of cardiac myocytes, *Biomaterials*, 24: 2463-76 (2003).
Muta et al., Apoptosis of human erythroid colony-forming cells is decreased by stem cell factor and insulin-like growth factor I as well as erythropoietin, *J. Cell Physiol.*, 156: 264-71 (1993).
Nahmias et al., Laser-guided direct writing for three-dimensional tissue engineering, *Biotechnol. Bioeng.*, 92: 129-36 (2005).
Nahta et al., Insulin-like growth factor-I receptor/human epidermal growth factor receptor 2 heterodimerization contributes to trastuzumab resistance of breast cancer cells, *Cancer Res.*, 65(23): 11118-28 (2005).
Norman et al., Control of cellular organization in three dimensions using a microfabricated polydimethylsiloxane-collagen composite tissue scaffold, *Tissue Eng.*, 11: 378-86 (2005).
Norman et al., Methods for fabrication of nanoscale topography for tissue engineering and scaffolds, *Ann. Biomed. Eng.*, 34: 89-101 (2006).
Norman et al., Microstructures in 3D biological gels affect cell proliferation, *Tissue Eng.*, 14(3): 379-90 (2008).
Oh et al., Cardiac progenitor cells from adult myocardium: homing, differentiation, and fusion after infarction, *Proc. Natl. Acad. Sci. USA*, 100(21): 12313-8 (2003).
Olson et al., Sizing up the heart: development redux in disease, *Genes Dev.*, 17(16): 1937-56 (2003).
Park et al., Microfabricated grooved substrates as platforms for bioartificial liver reactors, *Biotechnol. Bioeng.*, 90: 632-44 (2005).
Pedrotty et al., Engineering skeletal myoblasts: roles of three-dimensional culture and electrical stimulation, *Am. J. Physiol. Heart Circ. Physiol.*, 288: H1620-6 (2005).
Pelham et al., Cell locomotion and focal adhesions are regulated by the mechanical properties of the substrate, *Biol. Bull.*, 194: 348-50 (1998).
Pelham et al., Cell locomotion and focal adhesions are regulated by substrate flexibility, *Proc. Natl. Acad. Sci. USA*, 94(25): 13661-5 (1997).
Pfister et al., CD31− but not CD31+cardiac side population cells exhibit functional cardiomyogenic differentiation, *Circ Res.*, 97(1): 52-61 (2005).

(56) References Cited

OTHER PUBLICATIONS

Pitt, The controlled parenteral delivery of polypeptides and proteins, *Int. J. Pharm.*, 59: 173-96 (1990).
Popat et al., Influence of nanoporous alumina membranes on long-term osteoblast response, *Biomaterials*, 26: 4516-22 (2005).
Raines, The extracellular matrix can regulate vascular cell migration, proliferation, and survival: relationships to vascular disease, *Int. J. Exp. Pathol.*, 81: 173-82 (2000).
Reinecke et al., Survival, integration, and differentiation of cardiomyocyte grafts: A study in normal and injured rat hearts, *Circulation*, 100: 193-202 (1999).
Reiss et al., Acute myocardial infarction leads to upregulation of the IGF-1 autocrine system, DNA replication, and nuclear mitotic division in the remaining viable cardiac myocytes, *Exp. Cell Res.*, 213(2): 463-72 (1994).
Reiss et al., Overexpression of insulin-like growth factor-1 in the heart is coupled with myocyte proliferation in transgenic mice, *Proc. Natl. Acad. Sci. USA*, 93(16): 8630-5 (1996).
Richardson et al., Polymeric system for dual growth factor delivery, *Nat. Biotechnol.*, 19: 1029-34 (2001).
Rodriguez-Tarduchy et al., Insulin-like growth factor I inhibits apoptosis in IL-3-dependent hemopoietic cells, *J. Immunol.*, 149: 535-40 (1992).
Russell et al., Local injections of human or rat growth hormone or of purified human somatomedin-C stimulates unilateral tibial epiphyseal growth in hypophysectomized rats, *Endocrinol.*, 116(6): 2563-7 (1985).
Sahn et al., Recommendations regarding quantitation in M-mode echocardiography: results of a survey of echocardiographic measurements, *Circulation*, 58: 1072-83 (1978).
Samarel et al., Costameres, focal adhesions, and cardiomyocyte mechanotransduction, *Am. J. Physiol. Heart Circ. Physiol.*, 289(6): H2291-301 (2005).
Sarkar et al., Vascular tissue engineering: microtextured scaffold templates to control organization of vascular smooth muscle cells and extracellular matrix, *Acta Biomaterialia*, 1: 93-100 (2005).
Sauer et al., Characteristics of calcium sparks in cardiomyocytes derived from embryonic stem cells, *Am. J. Physiol. Heart Circ. Physiol.*, 281(1): H411-21 (2001).
Schiaffino et al., Molecular diversity of myofibrillar proteins: gene regulation and functional significance, *Physiol. Rev.*, 76(2): 371-423 (1996).
Semler et al., Mechanochemical manipulation of hepatocyte aggregation can selectively induce or repress liver-specific function, *Biotechnol. Bioeng.*, 69: 359-69 (2000).
Senyo et al., Stimulus interval, rate and direction differentially regulate phosphorylation for mechanotransduction in neonatal cardiac myocytes, *FEBS Lett.*, 581(22): 4241-7 (2007).
Sharp et al., Mechanical forces regulate focal adhesion and costamere assembly in cardiac myocytes, *Am. J. Physiol.*, 273: H546-56 (1997).
Shimatsu et al., Mosaic evolution of the insulin-like growth factors. Organization, sequence, and expression of the rat insulin-like growth factor I gene, *J. Biol. Chem.*, 262(16): 7894-900 (1987).
Shimizu et al., Cell sheet engineering for myocardial tissue reconstruction, *Biomaterials*, 24(13): 2309-16 (2003).
Shiraishi et al., Controlled-release preparation of indomethacin using calcium alginate gel, *Biol. Pharm. Bull.*, 16: 1164-8 (1993).
Shyy et al., Role of integrins in endothelial mechanosensing of shear stress, *Circ. Res.*, 91(9): 769-75 (2002).
Siegfried et al., A mitogenic peptide amide encoded within the E peptide domain of the insulin-like growth factorIB prohormone, *Proc. Natl. Acad. Sci. USA*, 89(17): 8107-11 (1992).
Sommer et al., Comparative anatomy: in praise of a powerful approach to elucidate mechanisms translating cardiac excitation into purposeful contraction, *J. Mol. Cell Cardiol.*, 27(1): 19-35 (1995).
Spach et al., Electrophysiological effects of remodeling cardiac gap junctions and cell size: Experimental and model studies of normal cardiac growth, *Circ. Res.*, 86: 302-11 (2000).
Street et al., Lateral transmission of tension in frog myofibers: a myofibrillar network and transverse cytoskeletal connections are possible transmitters, *J. Cell Physiol.*, 114(3): 346-64 (1983).
Streeter et al., Gross morphology and fiber geometry of the heart. Washington, DC: American Physiological Society; Chapter 4, 61-112 (1979).
Sung et al., The use of temperature-composition combinatorial libraries to study the effects of biodegradable polymer blend surfaces on vascular cells, *Biomaterials*, 26(22): 4557-67 (2005).
Swan et al., Fabrication and evaluation of nanoporous alumina membranes for osteoblast culture, *J. Biomed. Mater. Res.*, 72: 288-95 (2005).
Tao et al., Gastrointestinal patch systems for oral drug delivery, *Drug Discov. Today*, 10(13): 909-15 (2005).
Thacharodi et al., Collagen-chitosan composite membranes for controlled release of propranolol hydrochloride, *Int. J. Pharm.*, 120: 115-8 (1995).
Thakar et al., Regulation of vascular smooth muscle cells by micropatterning, *Biochem. Biophys. Res. Commun.*, 307: 883-90 (2003).
Torsoni et al., RhoA/ROCK signaling is critical to FAK activation by cyclic stretch in cardiac myocytes, *Am. J. Physiol. Heart Circ. Physiol.*, 289: H1488-96 (2005).
Tracy et al., Factors affecting the degradation rate of poly(lactide-co-glycolide) microspheres in vivo and in vitro, *Biomaterials*, 20: 1057-62 (1999).
Ungaro et al., Microsphere-integrated collagen scaffolds for tissue engineering: Effect of microsphere formulation and scaffold properties on protein release kinetics, *J. Control. Rel.*, 113(2): 128-36 (2006).
Vetter et al., Human fetal and adult chondrocytes. Effect of insulin-like growth factors I and II, insulin, and growth hormone on clonal growth, *J. Clin. Invest.*, 77(6): 1903-8 (1986).
Von Oepen et al., Injection moulding of biodegradable implants, *Clin. Mater.*, 10: 21-8 (1992).
Wang et al., Control of cytoskeletal mechanics by extracellular matrix, cell shape, and mechanical tension, *Biophys. J.*, 66: 2181-9 (1994).
Wang et al., Mechanotransduction across the cell surface and through the cytoskeleton, *Science*, 260: 1124-7 (1993).
Wang et al., Simple photografting method to chemically modify and micropattern the surface of SU-8 photoresist, *Langmuir*, 22: 2719-25 (2006).
Welch et al., Cardiac-specific IGF-1 expression attenuates dilated cardiomyopathy in tropomodulin-overexpressing transgenic mice, *Circ. Res.*, 90(6): 641-8 (2002).
Westfall et al., Troponin I isoform expression is developmentally regulated in differentiating embryonic stem cell-derived cardiac myocytes, *Dev. Dyn.* 206: 24-38 (1996).
Whitesides et al., Soft lithography in biology and biochemistry, *Annu. Rev. Biomed. Eng.*, 3: 335-73 (2001).
Wilson et al., Modeling the dynamic composition of engineered cartilage, *Arch. Biochem. Biophys.*, 408: 246-54 (2002).
Wobus et al., Embryonic stem cells—Prospects for developmental biology and cell therapy, *Physiol. Rev.*, 85(2): 635-78 (2005).
Wobus et al., Embryonic stem cells as a model to study cardiac, skeletal muscle, and vascular smooth muscle cell differentiation, *Methods Mol. Biol.*, 185: 127-56 (2002).
Yang et al., Cloning and characterization of an IGF-1 isoform expressed in skeletal muscle subjected to stretch, *J. Muscle Res. Cell Motil.*, 17(4): 487-95 (1996).
Zampino et al., Sex-related dimorphic response of HIF-1 alpha expression in myocardial ischemia, *Am. J. Physiol. Heart Circ. Physiol.*, 291(2): H957-64 (2006).
Zimmermann et al., Heart muscle engineering: an update on cardiac muscle replacement therapy, *Cardiovasc. Res.*, 71(3): 419-29 (2006).
Zimmermann et al., Tissue engineering of a differentiated cardiac muscle construct, *Circ. Res.*, 90(2): 223-30 (2002).
International Search Report, European Patent Office, PCT/US2008/070471, dated Oct. 28, 2008.
Office Action, U.S. Appl. No. 11/699,840, dated Oct. 6, 2009.
Office Action, U.S. Appl. No. 11/699,840, dated Jun. 24, 2010.
Office Action, U.S. Appl. No. 11/699,840, dated Nov. 3, 2010.

* cited by examiner

TEMPORAL RELEASE OF GROWTH FACTORS FROM 3D MICRO ROD SCAFFOLDS FOR TISSUE REGENERATION

This application is a continuation in part application of PCT application number PCT/US2008/070471, which was filed Jul. 18, 2008, claiming the benefit of priority of U.S. Provisional Application No. 60/950,454, which was filed Jul. 18, 2007. The present application also claims the benefit of priority of U.S. Provisional Application No. 61/179,584, which was filed May 19, 2009. The entire text of each of these priority documents is specifically incorporated herein by reference.

This invention was made with government support under HL 64956 and HL 62426 awarded by the National Institutes of Health (NIH). The government has certain rights in the invention.

FIELD OF THE INVENTION

The present invention relates to the use of three-dimensional microrod scaffolds for the temporal release of growth factors useful in tissue regeneration, engineering, and treatment of disorders.

BACKGROUND OF THE INVENTION

A major challenge in engineering tissues is mimicking the complex cellular organization and function of the native tissues of the human body. Tissue structure and function are very highly interrelated so that cellular and macromolecular organization of the tissue often brings about mechanical and biological functionality. For example, it is the circumferential arrangement of smooth muscle fiber layers that allows for change in the caliber in the lumen of blood vessels (Fawcett, 1986); the wickerwork pattern of collagen fibers in the skin give it mechanical strength (Alberts, 1994); the polygonal phenotype and complex arrangement of hepatocytes are essential for proper liver function (Boron, 2003); and the spiraling parallel arrangements of myocytes in the ventricle eject blood (Streeter, 1979; Sommer, 1995). Without proper cellular organization, an artificial tissue does not function adequately.

Many approaches to regain, for example, cardiac function depend on making layers of bundles of contractile myocytes in vitro with the intention of surgical implantation. Seeding of cardiac cells randomly into matrices or hydrogels fails because the cells are isolated from each other promoting cellular atrophy and apoptosis. The surviving cells are few in number and not electrically connected resulting in poor force production (Langer and Vacanti, 1993). Rat neonatal cells from primary culture have been grown on surfaces adhering to peptides stamped in parallel lines but are not all electrically connected laterally (Reinecke, 1999) and have all the disadvantages of two-dimensional culture. Another 2D approach involves releasing a monolayer of cells by temperature sensitive chemistry allowing the randomly oriented myocytes to contract (Shimizu, 2003). Multiple layers were tightly stacked and implanted by 'poly-surgery' to generate a thicker construct. Repeat surgeries at daily intervals would not be acceptable for human application.

A more promising approach involves myocytes grown on collagen networks that are mechanically paced to form 3D electrically connected strips that have been grafted in vivo (Zimmerman, 2002). This is appealing because it recreates trabeculae ensheathed with fibroblasts and endothelium ~100 µm in diameter. However, it is not easy to see how this approach could be scaled up for surgery. The recent exterior "chain-mail jacket" approach (Zimmerman, 2006) is fraught with practical difficulties for use in human patients. This model has an outer layer of connective tissue that might well cause fibrosis and prevent the myocytes of the graft from connecting directly with the healthy heart of the host. Without a good electrical connection the electrocardiogram would show incomplete synchronous activity. The cell source also remains an unresolved challenge.

There are inadequate local repair mechanisms within the heart to deal with physical and free radical damage following ischemic injury or mechanical overload. This problem is exacerbated by a wave of programmed death (apoptosis) of susceptible myocytes resulting in contractile dysfunction (Cheng, 1996; Kajstura, 1996). As in many cell types, IGF-1 can inhibit apoptosis (Muta, 1993; Rodriquez, 1992; Beurke, 1995) and thus, delivery of IGF-1 to the stressed heart may prevent myocyte cell death and improve cardiac function. However, data from animal studies have been equivocal, and data from human clinical trials have not demonstrated any significant effects of either administration of the mature IGF-1 or growth hormone (Deurr, 1996; Fazio, 1996). This result may not be too surprising since there is no evidence showing increased secretion of growth hormone or elevation of systemic IGF-I levels following myocardial infarcts. Furthermore, there are limitations to this approach due to the bioavailability in the heart because IGF-1 binds very rapidly to proteins in the systemic circulation. However, over-expression of the IGF-1 gene in the heart has proven beneficial in eliciting cardiac hyperplasia (Reiss, 1996), inhibiting apoptosis (Li, 1997) and preventing dilation in a transgenic mouse model of cardiomyopathy (Welch, 2002). Consequently, these salutary effects were attributed to the IGF-1 produced by the muscle even though the cDNAs used could not be spliced to produce muscle specific isoforms.

Thus there exists a need in the art to develop materials and methods for improving tissue regeneration in not only cardiac tissue but other tissue as well.

SUMMARY OF THE INVENTION

The present invention provides a scaffold comprising non-degradable or biodegradable microrods and optionally a carrier. In certain aspects, the carrier is a matrix. In various embodiments, the matrix is selected from the group consisting of: collagen, gelatin, gluten, elastin, albumin, chitin, hyaluronic acid, cellulose, dextran, pectin, heparin, agarose, fibrin, alginate, carboxymethylcellulose, Matrigel™, hydrogel and organogel.

In various embodiments, the microrods modulate the local microenvironment of a cell, alter a cell's cytoskeletal architecture, alter a cell's proliferation, including but not limited to promoting or suppressing cell proliferation, or regulating cellular organization, structure, phenotype or function.

In another aspect, the microrods are biodegradable. In other aspects, the microrods are porous, have a textured surface or are porous and have a textured surface.

In various aspects, the carrier is aqueous. In still other aspects, the carrier is saline or a buffer.

In one embodiment, the microrods are synthesized from one or more polymers. In other embodiments, polymer is selected from the group consisting of polylactic acid (PLA), polyglycolic acid (PGA), poly(ε-caprolactone) (PCL), poly(ethylene glycol) diacrylate (PEGDA), poly(ethylene glycol) dimethacrylate (PEGDMA) and SU-8.

In another embodiment, the microrods are synthesized from one or more copolymers. In yet another embodiment, the copolymer is selected from the group consisting of poly (lactide-co-glycolide) (PLGA) and poly(DL-lactide-co-ε-caprolactone) (DLPLCL).

In various aspects, the microrods are on average, each about 1 micron to 1,000 microns in length.

In other aspects, the microrods each have a cross-sectional area of about A microns times B microns where A=1 micron to 1000 microns and B=1 micron to 1000 microns.

In still other aspects, the microrods have a range of stiffness from about 1 kPa to about 1 GPa.

In certain embodiments, the microrods have a shape of a regular or irregular polyhedron. In other embodiments, the microrods have a three-dimensional shape selected from the group consisting of: rod, cube, cone, cylinder, sphere, spiral, deltoid, asteroid, rhombus, parallelogram, trapezoid, cuboid, pyramid, prism, tetrahedron, pentahedron, hexahedron, septahedron, octahedron, nonahedron and decahedron, and irregular cross-sections.

In one aspect, the microrods are associated with a biomolecule. In various aspects, the biomolecule is a protein in the insulin-like growth factor (IGF) family of proteins, an isoform of the IGF family of proteins, an E-domain peptide of the IGF family of proteins, or an Ea, Eb, or Ec domain peptide of the IGF family of proteins.

In other aspects, the biomolecule is mechano-growth factor (MGF). In still other aspects, the MGF is stabilized or native. In another embodiment, the biomolecule is an E-domain peptide of MGF or a biologically active fragment of MGF.

In one embodiment, the biomolecule is associated with the microrods by covalent interaction. In another embodiment, the biomolecule is elutable from the microrod.

In certain aspects, the microrods are associated with a targeting molecule that interacts with target cells expressing a binding partner for said targeting molecule. In other aspects, the targeting molecule is selected from the group consisting of: an organic compound, a drug, a peptide hormone, a cell adhesion molecule, a cell adhesion molecule ligand, an antibody immunospecific for an epitope expressed on a surface of a target cell type, a growth factor, a growth factor receptor expressed on the surface of a target cell type, a growth factor that modifies stem cell behavior, an anti-cancer agent, an anti-apoptosis agent, an agent that depresses fibrosis, an agent that builds blood vessels, an agent that suppresses cell proliferation, a cytokine, a chemokine and an anti-inflammatory agent.

In one embodiment, the microrods are associated with cells in vivo. In various embodiments, the microrods are associated with progenitor cells in vivo. In still other embodiments, the cells are cardiac cells, fibroblasts, cardiac myocytes, bone marrow mesenchymal cells, endothelial cells, smooth muscle cells, vascular cells, cardiac stem/progenitor cells, neuronal cells, neuroendocrine cells, skeletal muscle cells, bone cells, tendon cells, connective tissue cells, stem cells, or fibroblasts.

In one aspect, the microrod scaffold is an injectable composition or is surgically implantable.

Methods are also contemplated by the present invention. In one embodiment, a method for repairing damaged tissue comprising the step of administering the microrod scaffold to damaged tissue in an amount and over a time effective to repair damaged tissue is provided.

In one embodiment, the damaged tissue is muscle tissue or arises from a muscular disorder or trauma. In another embodiment, the damaged tissue is cardiac tissue or arises from a cardiovascular disorder or trauma. In still another embodiment, the damaged tissue is neuronal tissue or arises from a neurological disorder or trauma. In another aspect, the damaged tissue is neuroendocrine tissue or arises from a hormonal disorder such as diabetes or trauma.

In various aspects, the damaged tissue is selected from the group consisting of skeletal, bone, tendon and connective tissue or arises from growth abnormalities, osteoporosis, fractures, and ischemic damage due to peripheral vascular disease.

In one aspect, a method for promoting cell survival of differentiated cells comprising the step of administering the microrod scaffold to damaged tissue in an amount and over a time effective to promote cell survival is provided.

In another aspect, a method for promoting differentiation of a stem/progenitor cell comprising the step of administering the microrod scaffold to damaged tissue in an amount and over a time effective to promote differentiation is provided.

In still another aspect, a method for promoting cell proliferation of a stem/progenitor cell comprising the step of administering the microrod scaffold to damaged tissue in an amount and over a time effective to promote cell proliferation is provided.

Figure 18:
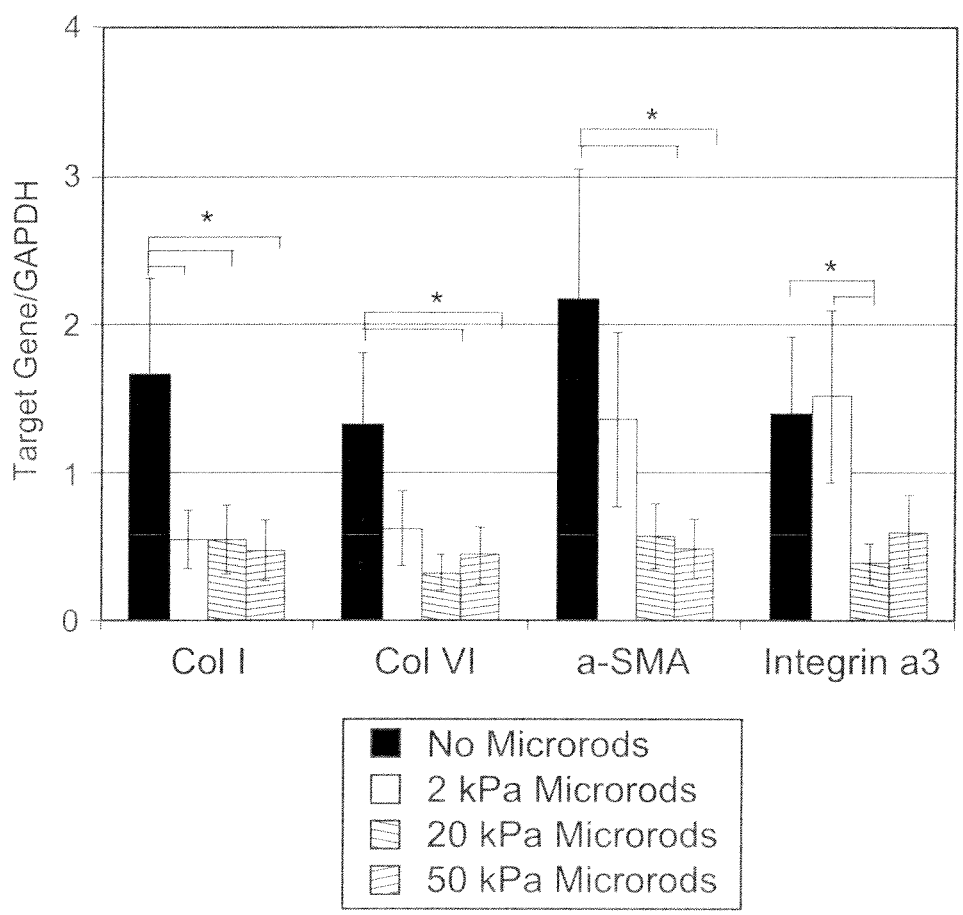

FIG. 18. PEGDMA MRS of different stiffness have a varied response on ECM synthesis and gene expression in 3D gels. Type I collagen was down-regulated in all MRS cultures. Fibroblasts with stiffer MRS showed down-regulation of type VI collagen and contractility marker α-SMA. Adhesion molecule integrin α3 was only down-regulated in cultures with 20 kPa microrods. Cultures with soft microrods showed no significant difference on the expression of Col VI, α-SMA, and integrin α3 compared to cultures with no microrods. Bars indicate SEM and (*) indicates p<0.05, (n=6).

Figure 19:
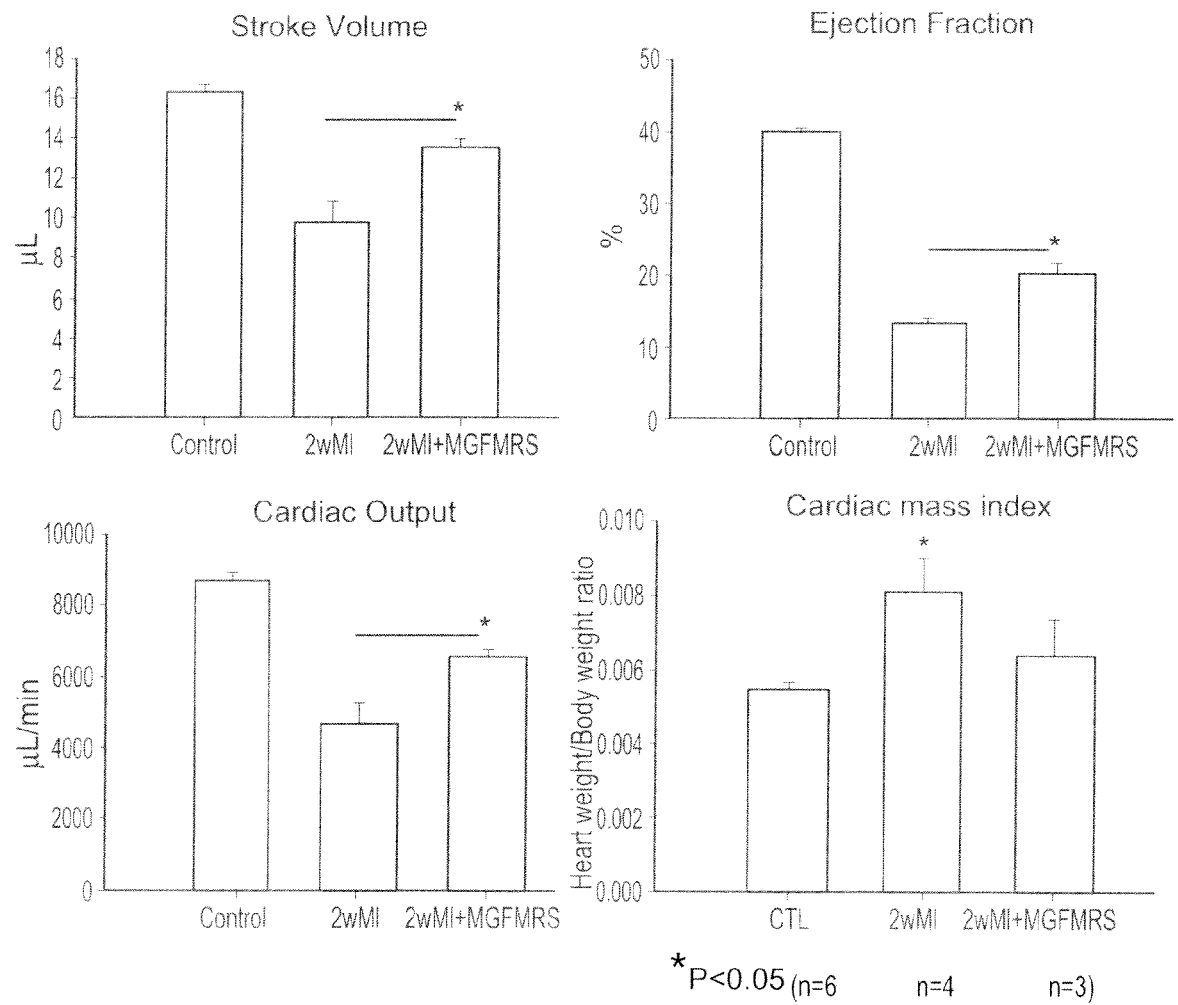

FIG. 19. shows cardiac parameters stroke volume, ejection fraction, cardiac output and cardiac mass index in control and mouse hearts injected with MGF E-domain MRS 10 minutes post infarct.

Figure 20:
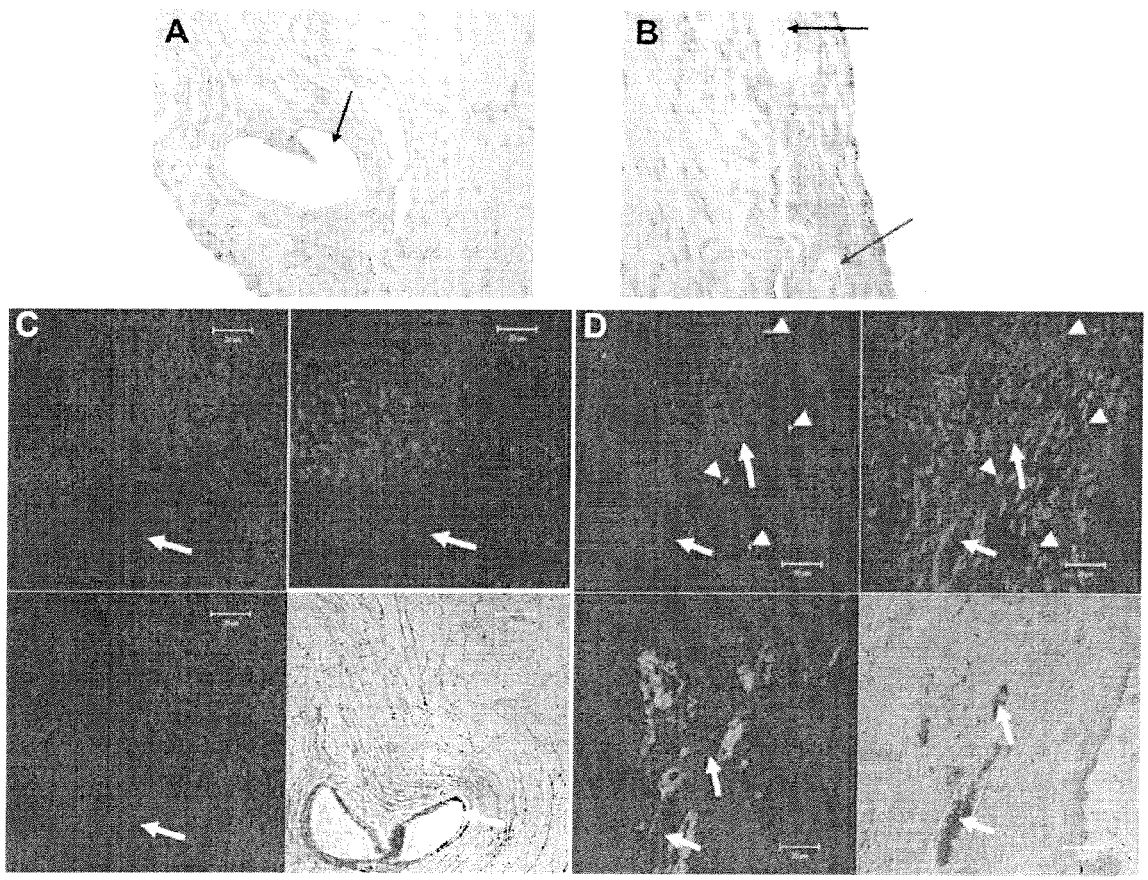

FIG. 20. shows control and MGF E-domain loaded MRS injected into mouse hearts. A. H&E staining of empty 50% PEGDA rod; B. H&E staining of E-domain loaded 50% PEGDA rod; C. Split panel images of Ki67 (green), ssTnI (red), DAPI (blue), staining of sections cut from empty PEGDA rod injection; D. Split panel images of Ki67 (green), ssTnI (red), DAPI (blue), staining of sections cut from E-domain loaded PEGDA rod injection. Arrows=MRS, arrowheads=Ki67+nuclei.

Figure 21:
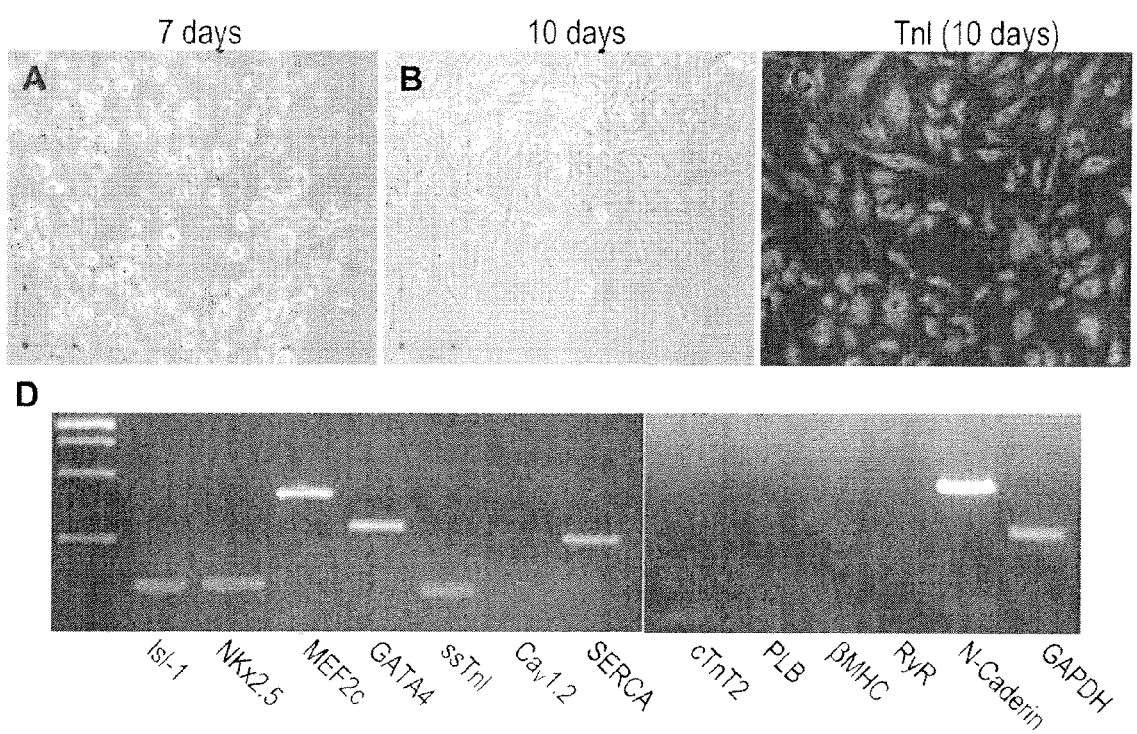

FIG. 21. shows isolated resident cardiac progenitor cells in vitro with time. A. 7 days; B. 10 days; C. 10 days staining with TnI antibody that recognizes ssTnI; and D. gene expression analysis in RP cells after 10 days in culture using RT-PCR.

Figure 22:
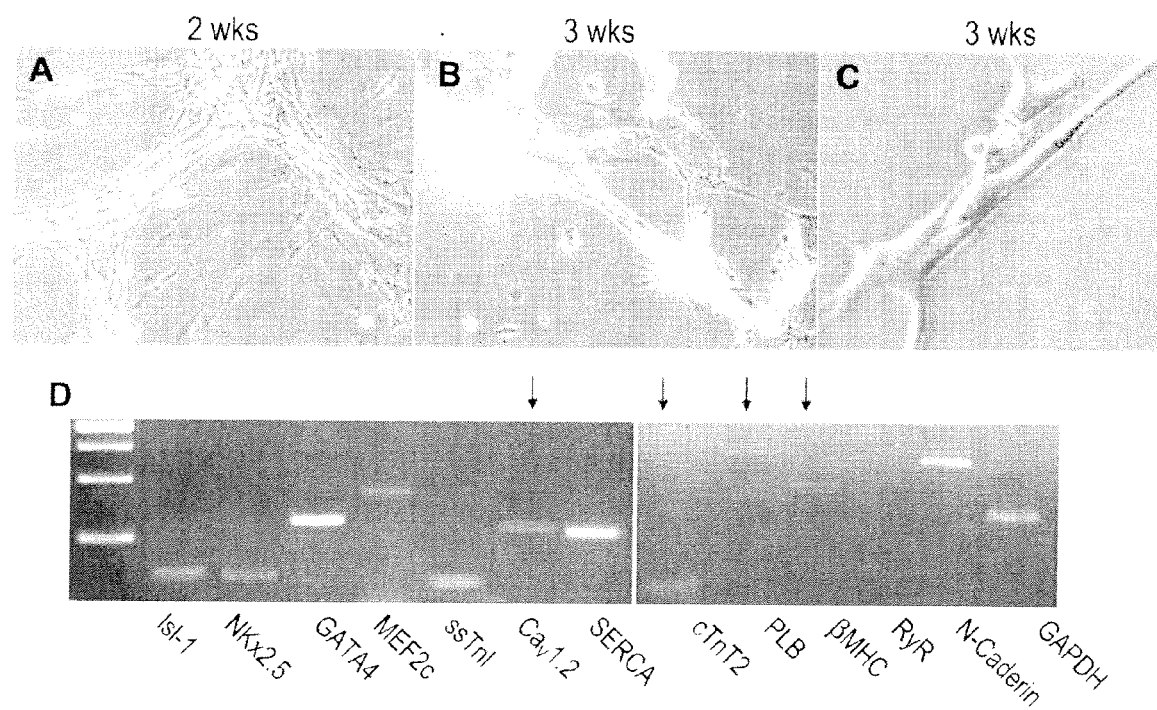

FIG. 22. shows differentiation of RP cells in vitro with Wnt 5a and Dkk1. A. treatment for 2 weeks; B. treatment for 3 weeks; C. treatment for 3 weeks with higher magnification showing cells that form cell-to-cell connections; D. gene expression analysis of RP cells after 3 weeks of treatment using RT-PCR. Arrows highlight genes expressed during differentiation.

DETAILED DESCRIPTION THE INVENTION

The present invention provides a scaffold comprising microrods and an optional carrier. The term "microrod" is a generic description that in only one aspect is a "rod-like" product. The term does not, however, imply that all microrods have the same shape, much less that they are all rod-like; despite the name, microrods of the scaffold can have any three dimensional shape. In various embodiments, microrods of the scaffold are cubes, cones, cylinders, spheres, rods, cuboids, pyramids, prisms, tetrahedrons, pentahedrons, hexahedrons, septahedrons, octahedrons, nonahedrons or decahedrons. Mixtures of microrods having one or more different shapes are contemplated in additional aspects of the scaffold. Accordingly, in various aspects, microrods have a three-dimensional shape of any regular polyhedron, any irregular polyhedron, and combinations thereof. The shape of a microrod is, in some ways dictated by the intended use. That is to say, certain microrod shapes may be more desirable for specific tissues, specific locations in specific tissues or specific modes of administration or implantation. For example, an injectable scaffold may require microrods of a shape that is amenable to the flow in an injection stream.

In certain instances, microrods having an increased surface area are beneficial. Surface area of any microrod is increased by synthesizing the microrod having a textured surface. Alternatively, microrods can be synthesized to be porous as another means to increase surface area. In still another alternative, the microrods are synthesized in such a way that they are both textured and porous.

Also, depending on their intended use, microrods are either non-degradable, partially biodegradable, wholly biodegradable, or combinations and/or mixtures thereof.

In various aspects, the microrods are synthesized from one or more polymers, one or more copolymers, one or more block polymers (including di-block polymers, tri-block polymers, and/or higher multi-block polymers), as well as combinations thereof. Useful polymers include but are not limited to polylactic acid (PLA), polyglycolic acid (PGA), poly(ϵ-caprolactone) (PCL), poly(ethylene glycol) diacrylate (PEGDA), poly(ethylene glycol) dimethacrylate (PEGDMA), SU-8, poly(methyl methacrylate), polylactic acid, polyglycolic acid, poly(lactide-co-glycolide), poly-caprolactone, and elatin/caprolactone, collagen-GAG, collagen, fibrin, poly(anhydrides), poly(hydroxy acids), poly (ortho esters), poly(propylfumerates), polyamides, polyamino acids, polyacetals, biodegradable polycyanoacrylates, biodegradable polyurethanes and polysaccharides, polypyrrole, polyanilines, polythiophene, polystyrene, polyesters, non-biodegradable polyurethanes, polyureas, poly (ethylene vinyl acetate), polypropylene, polyethylene, polycarbonates, poly(ethylene oxide), polydioxanone, "pseudo-polyamino acid" polymer based on tyrosine, tyrosine-derived polycarbonate poly(DTE-co-DT carbonate), polyethylene, tyrosine-derived polyarylate, polyanhydride, trimethylene carbonate, poly(β-hydroxybutyrate), poly(g-ethyl glutamate), poly(DTH iminocarbonate), poly(bisphenol A iminocarbonate), poly(ortho ester), polycyanoacrylate, and polyphosphazene, poly(lactide-co-glycolide) (PLGA), poly (DL-lactide-co-ϵ-caprolactone) (DLPLCL), a modified polysaccharide (cellulose, chitin, dextran) a modified protein, casein- and soy-based biodegradable thermoplastics, collagen, polyhydroxybutyrate (PHB), multiblock copolymers of poly(ethylene oxide) (PEO) and poly(butylene terephthalate) (PBT), polyrotaxanes (which are polymers comprising cyclic compounds that are threaded onto linear polymeric chains capped with bulky end groups). In other aspects, the microrods are formed from one or more phospholipids. 2-methacryloyloxyethyl phosphorylcholine (MPC), one or more cationic polymers (poly(a-[4-aminobutyl]-L-glycolic acid), or one or more silicone-urethane copolymers. In still other aspects, microrods in the scaffold are formed from co-polymers of any of the above, mixtures of the above, and/or adducts of the above. The worker of ordinary skill will readily appreciate that any other known polymer is suitable for making microrods of the instant scaffolds.

Because microrods of the invention are synthesized, physical properties of the microrods can be designed and controlled. In one aspect of the scaffold, microrods are on average, each about 0.01, about 0.05, about 0.1, about 0.5, about 1, about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400, about 405, about 410, about 415, about 420, about 425, about 430, about 435, about 440, about 445, about 450, about 455, about 460, about 465, about 470, about 475, about 480, about 485, about 490, about 495, about 500, about 505, about 510, about 515, about 520, about 525, about 530, about 535, about 540, about 545, about 550, about 555, about 560, about 565, about 570, about 575, about 580, about 585, about 590, about 595, about 600, about 605, about 610, about 615, about 620, about 625, about 630, about 635, about 640, about 645, about 650, about 655, about 660, about 665, about 670, about 675, about 680, about 685, about 690, about 695, about 700, about 705, about 710, about 715, about 720, about 725, about 730, about 735, about 740, about 745, about 750, about 755, about 760, about 765, about 770, about 775, about 780, about 785, about 790, about 795, about 800, about 805, about 810, about 815, about 820, about 825, about 830, about 835, about 840, about 845, about 850, about 855, about 860, about 865, about 870, about 875, about 880, about 885, about 890, about 895, about 900, about 905, about 910, about 915, about 920, about 925, about 930, about 935, about 940, about 945, about 950, about 955, about 960, about 965, about 970, about 975, about 980, about 985, about 990, about 995, or about 1000 or more microns in length.

In another aspect, microrods of the scaffold have a cross-sectional area of about A microns times B microns, wherein A and B are independently selected from about 1, about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400, about 405, about 410, about 415, about 420, about 425, about 430, about 435, about 440, about 445, about 450, about 455, about 460, about 465, about 470, about 475, about 480, about 485, about 490, about 495, about 500, about 505, about 510, about 515, about 520, about 525, about 530, about 535, about 540, about 545, about 550, about 555, about 560, about 565, about 570, about 575, about 580, about 585, about 590, about 595, about 600, about 605, about 610, about 615, about 620, about 625, about 630, about 635, about 640, about 645, about 650, about 655, about 660, about 665, about 670, about 675, about 680, about 685, about 690, about 695, about 700, about 705, about 710, about 715, about 720, about 725, about 730, about 735, about 740, about 745, about 750, about 755, about 760, about 765, about 770, about 775, about 780, about 785, about 790, about 795, about 800, about 805, about 810, about 815, about 820, about 825, about 830, about 835, about 840, about 845, about 850, about 855, about 860, about 865, about 870, about 875, about 880, about 885, about 890, about 895, about 900, about 905, about 910, about 915, about 920, about 925, about 930, about 935, about 940, about 945, about 950, about 955, about 960, about 965, about 970, about 975, about 980, about 985, about 990, about 995, or about 1000 or more microns.

In another embodiment, the microrods are designed to have a specific stiffness which provides extracellular attachment and force transmission. Forces generated by cells are important in tissue morphogenesis and have been shown to affect a number of cellular processes including: assembly and organization of the extracellular matrix, gene transcription, cell motility, growth, differentiation, apoptosis, and signal transduction (reviewed in Chicurel, 1998; Shyy and Chien, 2002; Samarel, 2005). Matrix rigidity also affects cellular phenotype (Pelham and Wang, 1997): on more compliant substrates, cells were less spread, focal adhesions were irregular, and motility rates were higher than on stiffer substrata. Substrate rigidity also can be manipulated to direct cell movement (Lo, 2000) and to optimize differentiation and myofibril assembly in skeletal myotubes (Engler, 2004) and stem cell phenotype and differentiation (Engler, 2006). Physical forces encountered by cardiac cells in vivo include active force production, gain and loss of adhesion, membrane stretch, and compression due to changes in ventricular cavity pressure. The molecular systems through which cells convert mechanical cues from the extracellular matrix, ECM, into intracellular signals (mechanotransduction) have been the subject of active investigation (Wang and Ingber, 1994; Ingber, 2003, 2006; Lele, 2006). Cardiomyocytes adhere to their ECM through membrane-associated structures known as costameres, vinculin-rich complexes that simultaneously engage ECM filaments through transmembrane integrin receptors and contractile cellular myofibrils through various adapter proteins. Thus, costameres mechanically couple the ECM to the cytoskeleton and may be regarded as specialized versions of focal adhesions (FAs), which anchor many cultured cells to the ECM (Holmes, 2005; Samarel, 2005). FAs play a central role in intracellular signaling by both serving as concentration points for canonical signaling enzymes which may directly regulate cell survival (Cooper, 1986), and by providing direct physical channels through which ECM distortion may be transmitted to the cellular interior (Wang, 1993). Often, these channels serve as a foundation for complex feedback relationships between mechanical inputs and cellular contractility; for example, externally applied mechanical loads feed back through activation of Rho GTPase to increase FA density, which in turn supports the development of additional contractile myofibrils (Sharp, 1997; Torsoni, 2005). In other words, there is a mechanical force balance between contractile tension exerted by myofibrils and the resistance to deformation (i.e., stiffness) of the ECM that stabilizes cardiomyocyte shape and directly drives signaling events in cardiomyocytes.

External stiffness is balanced by internal remodeling of the cell's cytoskeletal proteins for the assemblage of contractile filaments. Based on this model, intracellular tension depends on a mechanical force balance between cytoskeletal traction forces and the ability of the ECM substrate to resist these stresses. This creates a state of tensional "prestress" in the cytoskeleton dependent on the ECM (Huang and Ingber, 1999; Ingber and Jamieson, 1985). This is important because it suggests that local variations in ECM structure and mechanics may contribute to the regional differentials in cell shape, cytoskeletal organization, and intracellular biochemistry that affect certain disease processes.

Forces generated by cells have been shown to affect a number of cellular processes including: assembly and organization of the ECM, gene transcription, cell motility, growth, differentiation, apoptosis, signal transduction and even tissue morphogenesis (Chicurel, 1998; Shyy, 2002; Samarel, 2005). Myosin light chain kinase is essential for the cell contractility that makes cells stiffer and able to divide less often (Fazal, 2005). Matrix rigidity also affects adhesion, mobility and cellular phenotype (Pelham, 1997; Lo, 2000, Engler, 2004; Gray, 2003). Stem cell lineage and differentiation is also affected by the stiffness of the stubstratum (Engler, 2006) and the tension in the ectoderm and endoderm layers of early embryos is stiffer than the mesoderm tension. Interestingly, cells sort according to tension rather than adhesivity and they require internal contractility to generate this tension in order to do so (Krieg, 2008).

Another example of the matching of external and internal forces is seen in muscle where it is well known that work against a heavy load leads to an increase in muscle mass (hypertrophy). Muscle cells are unique in that they respond to both externally applied mechanical forces, as well as generating very large internal loads that are transmitted to adjacent cells and their surrounding ECM. Physical forces encountered by cardiac cells in vivo include active force production, adhesion and compression due to changes in ventricular cavity pressure. The molecular systems through which muscle cells convert mechanical cues from the ECM into intracellular signals (mechanotransduction) have been the subject of active investigation (Wang, 1994; Ingber, 2003, 2006; Lele, 2006). The anisotropic geometry of the cardiac myocyte with its longitudinal and lateral structure may allow for distinct pathways of force recognition and transmittance (Street, 1983; Bloch, 2003; Collinsworth, 2003). Separate directional pathways are implicated by static transverse and longitudinal loading to activate stress induced-MAP kinase (Kumar, 2002) and anisotropic mechanosensing with focal adhesion kinase (FAK) phosphorylation (Senyo, 2007).

Accordingly, microrods of the scaffolds have a stiffness of about 0.01, about 0.05, about 0.1, about 0.5, about 1, about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400, about 405, about 410, about 415, about 420, about 425, about 430, about 435, about 440, about 445, about 450, about 455, about 460, about 465, about 470, about 475, about 480, about 485, about 490, about 495, about 500, about 505, about 510, about 515, about 520, about 525, about 530, about 535, about 540, about 545, about 550, about 555, about 560, about 565, about 570, about 575, about 580, about 585, about 590, about 595, about 600, about 605, about 610, about 615, about 620, about 625, about 630, about 635, about 640, about 645, about 650, about 655, about 660, about 665, about 670, about 675, about 680, about 685, about 690, about 695, about 700, about 705, about 710, about 715, about 720, about 725, about 730, about 735, about 740, about 745, about 750, about 755, about 760, about 765, about 770, about 775, about 780, about 785, about 790, about 795, about 800, about 805, about 810, about 815, about 820, about 825, about 830, about 835, about 840, about 845, about 850, about 855, about 860, about 865, about 870, about 875, about 880, about 885, about 890, about 895, about 900, about 905, about 910, about 915, about 920, about 925, about 930, about 935, about 940, about 945, about 950, about 955, about 960, about 965, about 970, about 975, about 980, about 985, about 990, about 995, about 1000, about 2000, about 3000, about 4000, about 5000, about 6000, about 7000, about 8000, about 9000, about 10000, about 11000, about 12000, about 13000, about 14000, about 15000, about 16000, about 17000, about 18000, about 19000, about 20000, about 21000, about 22000, about 23000, about 2400, about 25000, about 26000, about 27000, about 28000, about 29000, about 30000, about 31000, about 32000, about 33000, about 34000, about 35000, about 36000, about 37000, about 38000, about 39000, about 40000, about 41000, about 42000, about 43000, about 44000, about 45000, about 46000, about 47000, about 48000, about 49000, about 50000, about 51000, about 52000, about 53000, about 54000, about 55000, about 56000, about 57000, about 58000, about 59000, about 600000, about 61000, about 62000, about 63000, about 64000, about 65000, about 66000, about 67000, about 68000, about 69000, about 70000, about 71000, about 72000, about 73000, about 7400, about 75000, about 76000, about 77000, about 78000, about 79000, about 80000, about 81000, about 82000, about 83000, about 84000, about 85000, about 86000, about 87000, about 88000, about 89000, about 90000, about 91000, about 92000, about 93000, about 94000, about 95000, about 96000, about 97000, about 98000, about 99000 or about 1000000 kilopascals or more.

In various aspects the scaffold comprising the microrods also includes a carrier. As discussed above, the nature of the carrier, if present, is in certain aspects dictated by the intended use of the scaffold, and in other aspects, the means by which the scaffold in placed in a target tissue. In various aspects, therefore, the carrier is simply water, and in one aspect pharmaceutical grade water. In other aspects, the carrier is a buffer, and in certain aspect, the buffer is pharmaceutically acceptable. Buffers in the scaffold include, but are not limited to, saline, glycine, histidine, glutamate, succinate, phosphate, acetate, aspartate, or combinations of any two or more buffers. The worker of skill in the art will appreciate any pharmaceutically acceptable buffer is contemplated for use in the scaffold as a carrier.

In other aspects, the carrier, if present, is a matrix. A matrix is useful as a carrier in those instances when the scaffold is required to maintain some degree form, regardless of the pliability or permanence of the form. As such, in one aspect, the matrix is viscous, yet still flowable, and in other aspects, the matrix is solid, semi-solid, gelatinous or of any density in between. Accordingly, in various embodiments and without limitation, the matrix is collagen, gelatin, gluten, elastin, albumin, chitin, hyaluronic acid, cellulose, dextran, pectin, heparin, agarose, fibrin, alginate, carboxymethylcellulose, Matrige™ (a hydrogel formed by a solubilized basement membrane preparation extracted from the Engelbreth-Holm-Swarm EHS) mouse sarcoma), hydrogel organogel or mixtures and/or combinations thereof. Again, the worker of ordinary skill in the art will appreciate that any pharmaceutical grade matrix is amendable for use in a scaffold of the invention.

Scaffolds of the invention are useful simply as microrods, or as microrods and a carrier in view of the fact that the microrods are capable of influencing the local environment of target cells, and in certain instances, alter cellular cytoskeletal architecture, alter cellular proliferation, suppress cellular proliferation, promote cellular proliferation or regulate cellular organization, structure, phenotype and/or function. However, in certain aspects, the scaffold is utilized to further modulate a biological process in or around a target cell or tissue type beyond the effect of the microrod itself, and in those instances, the scaffold further comprises one or more biomolecules which has the ability to modulate one or more desired biological effects.

A biomolecule is any naturally-occurring or synthetic chemical compound that is produced by or can play a role in the processes of living cells. Accordingly, biomolecule includes but is not limited to naturally-occurring and synthetic nucleic acids, including DNAs, RNAs, antisense RNAs, siRNAs, ribozymes, oligonucloetoides; lipids, including but not limited to phospholipids, glycolipids, steriods, sterols, cholesterol, prostaglandins, leukotrienes; carbohydrates, including but not limited to sugars, oligosaccharides, polysaccharides, monosaccharides, disaccharides; polypeptides, including but not limited to amino acids, peptides, enzymes, hormones, cytokines, chemokines, growth factors, vitamins, neurotransmitters; therapeutics, including but not limited to analgesics, antibiotics, anticancer agents, anti-inflammatory agents, anti-apoptotic agents; drugs, including but not limited to agents that depress fibrosis, build blood vessels, suppress cell proliferation, promote wound healing, promote treatment of disease, and/or combinations of the above.

In one aspect, the biomolecule is a protein in the IGF family of proteins. In one embodiment, the biomolecule is IGF or a biologically active fragment thereof, including, but not limited to mechano-growth factor (MGF) or a biologically active fragment thereof. In yet another aspect, a IGF E-domain peptide is the Ea, Eb or Ec domain or a biologically active fragment thereof. In yet another aspect, MGF E-domain peptide is the biologically active fragment thereof. The E-domain of MGF is produced by the heart within days after stress but not bound by circulating binding proteins and thus is available to potentiate the actions of local IGF-1. MGF is up-regulated in skeletal muscle under conditions of increased growth (Yang, 1996, 2002; McCoy, 1999), and it is a splice variant of IGF-1 only produced by the tissue at times of stress. While IGF-1 functions as an endocrine factor secreted by the liver, it also functions as a paracrine/autocrine growth factor expressed in non-hepatic tissues mediating regenerative processes thus having the potential for undesirable effects for therapeutic application (Russell, 1985; Vetter, 1986). Multiple IGF-1 isoforms are expressed in different tissues that arise by alternate splicing from a common translated prepro-hormone. The preprohormone is cleaved by cellular endoproteases leaving the prohormone (mature 70 amino acid peptide+E-domains), which is further cleaved to yield identical mature peptides from all isoforms but different E-domains (Foyt, 1991). One isoform, the IGF-1Ea, has a similar structure to the major endocrine form produced by the liver and has been given various abbreviations including (confusingly) muscle-liver type IGF-1 and muscle IGF-1. Another, IGF-1Eb, or MGF is produced in stressed skeletal muscle. In the rodent, MGF (IGF-1Eb) has a 52 base pair insert from exon 5, which causes a reading frame shift at the carboxyl end encoding a unique 24 amino acid E-domain which distinguishes it from the predominant IGF-1Ea isoform (Shimatsu, 1987). Note, however, rodent Eb is named Ec in humans. Stabilized IGF, MGF and/or E-domain peptides are chemically modified to increase the molecule's stability, preserve its activity, or resistance to degradation. Conversely, native IGF, MGF and/or E-domain peptides refers to non-stabilized or not otherwise modified MGF.

In various aspects, the biomolecule is associated with the microrods by covalent interaction, and in other aspects the biomolecule is associated with the microrods by non-covalent association. In a covalent interaction, one or more biomolecules are directly attached to the microrod through any suitable means. Alternatively, one or more biomolecule is attached to the microrod through a space or linker that has no biological activity itself, or through a second biomolecule which possesses the same or a different biological activity compared to the first biomolecule. In still another aspect, the biomolecule is elutable from the microrod. Elutable in various aspects means that the biomolecule can be separated from the microrods through, for example, simply diffusion, cleavage of a covalent bond, dissociation or some other type of interaction. The biomolecule, in various aspects, is released in a controlled manner and in other aspect, the release is bolus in nature.

In yet another embodiment of the invention, the microrods are associated with a targeting molecule that interacts with a target cell or tissue expressing a binding partner for said targeting molecule. In various specific aspects, the targeting molecule is without limitation and for purposes of exemplification only, a cell adhesion molecule, a cell adhesion molecule ligand, an antibody immunospecific for an epitope expressed on the surface of a target cell type, or any member of a binding pair wherein one member of the binding pair is expressed on the target cell or tissue of interest.

In another embodiment, the microrods are associated with cells in vitro and in vivo. In this aspect of the invention, the microrods are mixed with cells and/or modified in such a way that the microrods attract cells from the environment, whether in vivo or in vitro. In certain aspects, the cells associated with the microrods are of the same type as the target tissue or cell type for which the microrods are intended for use. In various aspects, and without limitation, the cells are stem cells, muscle cells, cardiac cells, smooth muscle cells, bladder cells, brain cells, kidney cells, muscle (skeletal, smooth and cardiac) cells, neuronal cells, liver cells, pancreatic cells, and skin cells, as well as cells associated with tendons, cartilage and bone.

Accordingly, the cells may be, but are not limited to: stem cells, embryonic, adult or progenitor cells; muscle cells, cardiac, smooth or skeletal myocytes, myoblasts, myoepithelial, myofibroblasts, myoendothelial or pericytes; bladder epithelial cells; brain cells, neuron, glial, epithelial or oligodendrocytes; kidney cells, parietal, podocytes, proximal tubule brush border, Loop of Henle thin segment, thick ascending limb, distal tubule, cortical collecting duct, medullary collecting duct or interstitial; neuronal cells, neurons, Schwann, basket, Betz, Purkinje, pyramidal, Renshaw, granule, anterior horn, motor neurons or alpha motor neurons; liver cells, hepatocytes, cholangiocytes or ovalocytes; pancreatic cells, Islet, alpha, beta, delta or polypeptide producing; skin cells, epidermal, melanocytes, Merkel, keratinocytes or Langerhans; tendon cells, tenocytes; cartilage cells, chondrocytes, chondroclasts, chondroprogenitor or chondroblasts; bone cells, osteoclasts, osteoblasts, osteocytes, osteoprogenitor or osteoid cells.

As discussed herein, compositions comprising the scaffold of the invention are designed based on the intended use of the scaffold, for example, with respect to the target tissue or cell type and/or the route or means of administration. In certain aspects, the route or means of administration is an overriding factor is preparation of the scaffold or a composition comprising a scaffold. Administration of the scaffold compositions may be accomplished in a number of ways including, but not limited to, surgical implantation, injection, parenteral delivery, including intramuscular, subcutaneous, intramedullary as well as intrathecal, direct intraventricular, intravenous, intraperitoneal, intranasal, intraocular, intestinal administration, topical, inhalation, transdermal, transmucosal, buccal, pulmonary, sublingual, oral, rectal or vaginal. Osmotic mini-pumps and timed-released pellets or other depot forms of administration may also be used.

Methods are also contemplated by the present invention. In one embodiment, a method for repairing damaged tissue comprising the step of administering an aforementioned composition to damaged tissue in an amount and over a time effective to stimulate tissue repair, is provided. Methods of the invention are useful for the treatment of disorders such as, but not limited to, muscular disorders such as, but not limited to all forms of muscular dystrophy, atrophy, cachexia, sarcopenia and weakness of urethral sphincter muscle. In another aspect, the damaged tissue is cardiac tissue, wherein the method are useful for the treatment of, among other disorders, cells damaged by trauma, cardiomyopathies, ischemic cardiac injury, myocardial infarction, congestive heart failure, coronary artery disease or other damage. In yet another aspect, the damaged tissue is neuronal tissue, and methods are useful for the treatment of, among other disorders, neurological disorders (loss of neurons due to damage or maintenance of CNS, stroke), and neurodegenerative disorders (ALS, Parkinson's Alzheimer's). In still another aspect, the damaged tissue is neuroendocrine tissue, and methods of the invention are useful for the treatment of, among other disorders, hormonal disorders (diabetes). In yet another aspect, the damaged tissue is skeletal, bone, tendon and connective tissue. And methods of the invention are useful for the treatment of, among other disorders, growth abnormalities, osteoporosis, and fractures.

Ischemic damage due to peripheral vascular disease affects many of the tissues in body mentioned above, as well as others. All tissues damaged by ischemic disease would benefit from treatments with the invention.

The invention provides methods for use of the microrod scaffold for veterinary uses. In animal husbandry, the administration of drugs to animals involves a great deal of handling which is laborious for the handler and stressful for the animals. Often animals must be brought in from long distances making prolonged or frequent treatment difficult if not prohibitive. In some cases the stress levels caused by handling stock can impair the performance of the treatment, this is particularly true in deer. Many drugs are given in slow release capsules that can cause problems when still remaining in the animal at slaughter. (U.S. Pat. No. 6,669,682)

Many formulations are designed for long release to reduce stock handling requirements but concentrations often fall below the effective therapeutic levels long before the next dose is administered thus increasing the risk of drug resistance. Bacterial drug resistance is a growing problem that affects both animals and humans and commonly arises from the ineffective administration of drug treatments. Parasite drug resistance is now a major problem particularly with anti-parasite drugs such as anthelminthics. (U.S. Pat. No. 6,669,682)

Accordingly, the present invention contemplates uses of the microrod scaffold for biomolecule delivery in veterinary applications.

The invention provides methods for use of the microrod scaffold for tissue engineering. Tissue engineering often involves delivering a gel material such as hydrogel into a defective area of the body or to a body area where repair or reconstruction is desired. The gel material can be used as a support matrix for the growth of surrounding tissue cells. (U.S. Pat. No. 6,991,652) Often cells or tissues, or as in the present invention, microrods are also dispersed in the gel material and injected or surgically implanted into the body along with the gel material to promote tissue regeneration, promote or suppress cell proliferation, alter cytoskeletal architecture, modulate the local environment of a cell or otherwise regulate cellular organization, structure, phenotype or function.

The condition of skin tissue is affected by factors such as humidity, ultraviolet rays, cosmetic compositions, aging, diseases, stress and eating habits. As the result, various skin troubles can arise. The skin also becomes less resilient with age as illustrated by the formation of wrinkles. Aging is generally associated with the thinning and general degradation of skin. As the skin naturally ages, there is a reduction in the number of cells and blood vessels that supply the skin. There is also a flattening of the dermal-epidermal junction that results in weaker mechanical resistance of this junction. As a consequence, older persons are more susceptive to blister formation in cases of mechanical trauma or disease processes. (U.S. Pat. No. 7,196,162).

The skin also contains an elaborate network of elastin fibers that is responsible for maintaining its elastic properties. With excessive exposure to sunlight the elastic fiber system becomes hyperplastic, disorganized and ultimately disrupted. This process is known as actinic elastosis and it is the principal cause of wrinkling, discoloration and laxity of the skin in the exposed areas of the body. As new fibroblasts, endothelial cells and keratinocytes form, the skin can repair itself. However, the skin becomes less able to do so as it ages. Therefore, agents that can accelerate the growth and repair of prematurely aged skin are needed. (U.S. Pat. No. 7,196,162)

Accordingly, the invention contemplates methods for treating symptoms of aging where the microrod scaffold is administered in an amount and over a time effective to reverse or treat the symptoms of aging.

The compositions of the invention are also used for anabolic therapeutics. In various embodiments, the invention is used to treat anabolic disorders including but not limited to, andropause, adisopogenital syndrome, functional metrorragia, fibroma and endometriosis as well as asthenia, osteoporosis, senescence and metabolic perturbations after prolonged treatment with corticotheraphy. Methods are also contemplated for anabolic therapeutics. In one embodiment, the invention is used for treating anabolic disorders by administering an anabolically effective amount of the microrod scaffold over a time effective to reverse the effects of the anabolic disorder (U.S. Pat. No. 4,431,640).

Methods are also provided for promoting survival of differentiated cells comprising the step of administering a scaffold to damaged tissue in an amount and over a time effective to stimulate tissue repair. Methods are contemplated for promoting differentiation of a stem/progenitor cell comprising the step of administering an aforementioned composition to damaged tissue in an amount and over a time effective to stimulate tissue repair, is provided. In yet another embodiment, a method for promoting cell proliferation of a stem/progenitor cell is provided comprising the step of administering an aforementioned composition to damaged tissue in an amount and over a time effective to stimulate tissue repair.

EXAMPLES

Integrating the E-domain of MGF in a microrod scaffold (MRS) offers many advantages as an innovative cardiac therapy. It is advantageous to design drug and peptide delivery systems that reproducibly and safely carry drugs to their point of action at the required level, thus controlling the pharmacokinetic parameters. Poly(lactide-co-glycolide) (PLGA) is an FDA-approved biocompatible and biodegradable copolymer of poly(lactic acid) (PLA) and poly(glycolic acid) (PGA) that can be formulated into MRS. PLGA for drug delivery usually consists of the amorphous racemer D,L-PLA, which allows for more homogeneous drug dispersions (Jain, 2001). The PLA:PGA monomer ratio dictates the physical and chemical characteristics of the copolymer. For example, the PLA methyl group (—CH3) renders the copolymer more hydrophobic and less crystalline than PGA, and thus it degrades slower. During PLGA degradation, the ester bonds of the polymer backbone are hydrolyzed to form soluble oligomers and monomers that then enter the citric acid cycle (Shive, 1997). MGF E-domain peptide molecules in the PLGA MRS core are protected from enzymatic and chemical degradation until they are released from the matrix. This protection within the MRS permits the delivery of insoluble drugs and, most importantly, increases the chances that an otherwise unstable peptide can be delivered to its site of action.

Example 1

Effect of Biodegradable Microrod Scaffolds on Myocyte Organization and Function

Microstructure Size

Microstructures with the volume (cross-sectional area 15×15 µm2, length 100 µm) but varying in stiffness (tensile moduli 0.01 kPa to 1 GPa) are used and fabricated as described below. All experiments are repeated with 5 primary cultures for statistical analysis.

Microstructure Stiffness

PLGA/PCL blends are initially chosen because this material can easily be microfabricated, is biocompatible, has a tunable modulus, and can degrade and release drug over a suitable time period (~2 weeks). Specifically, the effects of MRS made from polymer blends of varying stiffness are compared. The stiffness of the polymer MRS can be modulated in the proposed range by varying the PLGA co-polymer ratio and incorporation of a less stiff PCL component. This systematic tuning in mechanical properties was recently demonstrated by Sung (2005). The following blends are initially used: 50/50 poly(DL-lactide-co-glycolide) (PLGA) (Amorphous, Tg=45 to 50° C.), 25/75 poly(DL-lactide-co-ε-caprolactone) (25/75 DLPLCL) (Amorphous, Tg=20° C.), 80/20 poly(DL-lactide-co-ε-caprolactone) (80/20 DLPLCL) (Amorphous, Tg=20° C.), and poly(ε-caprolactone) (PCL) (Tm=58-63° C., Tg=65 to −60° C.). PDMS masters are created from silicon wafers supporting SU-8 microrods. Microtransfer molding is then used to form the structures in PLGA and PLGA-PCL blends. Specifically, PLGA is dissolved in solvent and deposited on the PDMS mold and placed under vacuum to displace trapped air. A silicon wafer is placed over the mold and the mold is inverted, placed under pressure, and cured. Once cured, the mold is peeled off. One disadvantage of using microtransfer molding is the residual thin film of polymer interconnecting each individual microrod. This film can be removed by etching or by applying excess pressure to the mold to separate MRS from the film. In this manner, several batches of MRS may be generated from a single master. Using these preparation techniques, 50/50 PLGA microstructures with moduli ranging from 500 MPa to 1300 MPa were obtained. Furthermore, peptides may be added to the prepolymer solution and incorporated into the MRS during the transfer process.

Material Evaluation

Tensile properties of the polymer blends used for the MRS can be measured using a method adapted from Huang (2006). Effects of polymer composition on mechanical properties are assessed through uniaxial cyclic loading using an electromechanical testing system. Uniform individual films (200 µm thick) are stretched to 10% strain, allowed to recover for 2 min, and loaded again to 0.3 N to failure. Linear (Young's) moduli, maximum stresses, yield strains and recovery percentages (working strains) are determined from the stress-strain curves. All experiments are repeated three or more times with triplicate samples.

Cell Density

The chance that a cell encounters a microstructure in 3D volume depends on the concentration and volumes of cells and of the MRS. Neonatal rat ventricular fibroblasts (NRVF) are relatively small cells (under 1,000 µm3) while NRVM are at least three-fold larger, for cell isolation and culture see Boateng 2003. Three seeding concentrations of the NRVF (250, 500 and 1,000×103/µm3 of Matrigel™) and various MRS concentrations from 0, 5,000, 10,000 and 20,000 rods/microliter of gel are used.

Cell Proliferation of NRVF and MRS Stiffness

Cell number is rapidly assessed by dissolving the gel and counting directly by cytometry or by the WST-1 colorimetric assay. The amount and distribution of NRVF proliferation is also measured directly using BrDU immunolocalization to compare the DNA replication proteins in cells near the MRS with those distant. The mixed cell population complicates interpretation of cell proliferation. However, the relative contribution of NRVF is determined by western blots to assess NRVM by myosin and fibroblasts by the aminopropeptide of procollagen then calculating the NRVM/NRVF ratio, as done before (Boateng, 2003). Hypertrophy of NRVM is desirable in healthy heart cell culture, reflected by the increase in the amount of contractile protein per DNA. Therefore, cells are isolated from the gel and determine the cell size, total protein and total myosin per dish to calculate protein/DNA.

NRVM Phenotype and Gene Expression and Microrod Stiffness

NRVM are terminally differentiated cells that no longer have the capacity to divide. Instead, NRVM are known to respond to increased workload, or increased reactive forces, by becoming larger (hypertrophy) and expressing a more mature contractile phenotype. Hypertrophy and maturation of the muscle phenotype increases proportionately when NRVM are exposed to embedded MRS of varying stiffness. Maturation of a muscle phenotype is not simply an increased size, but involves myofibrillar organization, contractile isoform expression as well as myriad calcium handling and energetic modifications.

Tissue Architecture of NRVM and NRVF and Microrod Stiffness

MRS with stiffness varying from 50 MPa to 500 MPa or cells grown in the Matrigel™ alone is used to analyze the effect of microrod stiffness on tissue architecture of NRVM and NRVF. Myofibrillar organization is assessed morphologically using confocal microscopy to identify well-organized sarcomeres by myosin heavy chain (MF-20) and α-actinin antibodies followed by counterstaining with FITC-phalloidin for anti-sarcomeric and F-actin. The Z-stack mode permits analysis of 3D structural features to determine the extent of longitudinally running myofibrils vs. the non-striated stress cables (Motlagh, 2003).

Figure 16:
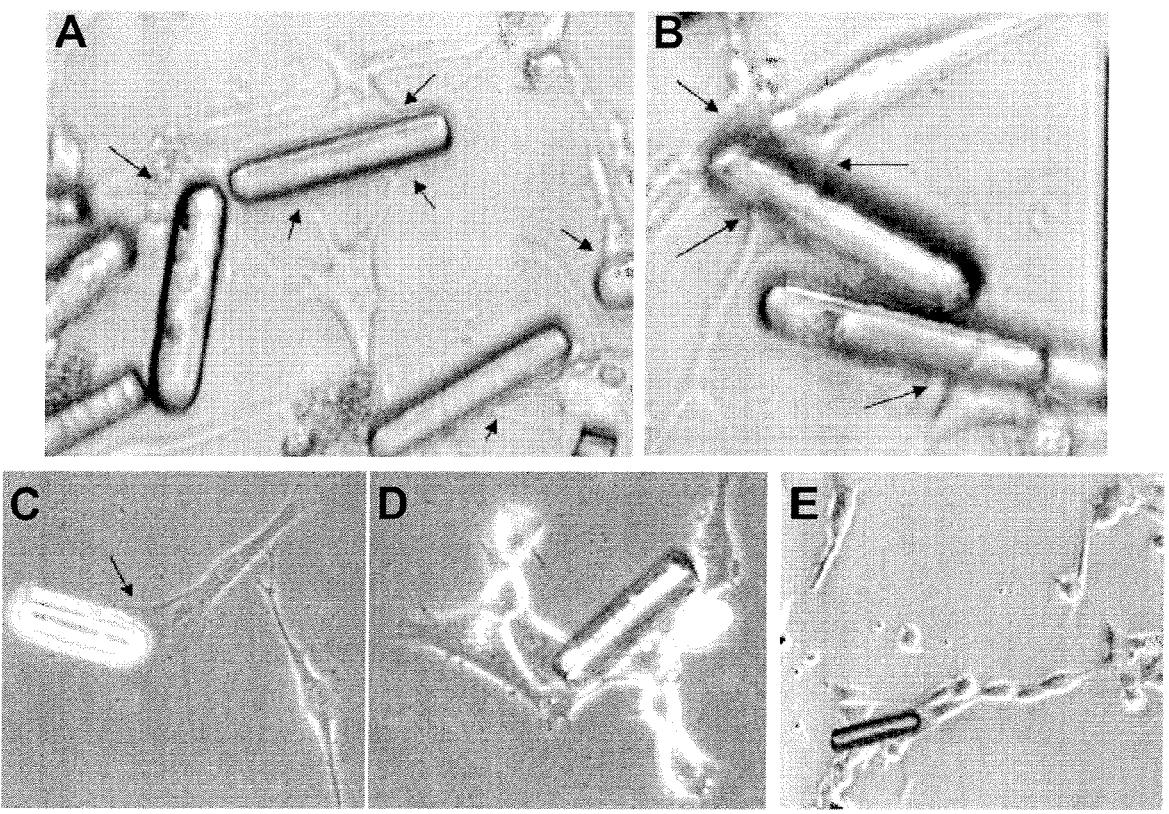
FIG. 16. shows resident cardiac progenitor (RP) cells cultured with MRS of different materials and stiffness. A. RP cells cultured with SU-8 rods for 7 days. B. Higher magnification. C. RP cells cultured with 50% PEGDA rods for 2 days. D. 7 days. E. 2 weeks.

Physical cues of MRS stiffness alone (without grown factors) can serve as a scaffold system to support resident cardiac progenitor cell interaction and lineage commitment. Resident cardiac progenitor (RP) cells were cultured with MRS of different materials and stiffness (FIG. 16). FIG. 16A shows RP cells cultured with SU-8 MRS for seven days whereas FIGS. 16C-E shows RP cells cultured with 50% PEGDA MRS for two days, seven days and two weeks, respectively. These data show that RP cells contact and assemble on the MRS and that the material of choice (PEGDA), which can be tuned to different stiffness, is appropriate. Extended culture with PEGDA MRS supports the formation of cell-to-cell contacts that appear to be the initial steps of RP cell differentiation (FIG. 16E). Together, these data demonstrate that the physical cues supplied by the MRS alone can serve as a scaffold system that supports RP cell interaction and lineage commitment.

Figure 17:
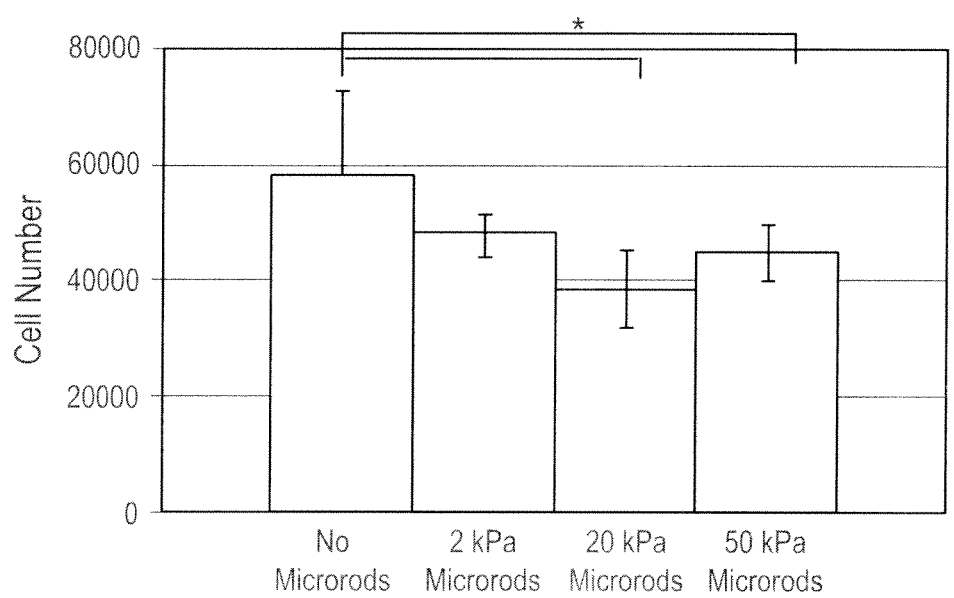
FIG. 17. shows fibroblast proliferation significantly reduced in gels with PEGDMA MRS of higher stiffness (20 kPa, 50 kPa). No significant difference was found with softer MRS (2 kPa) as analyzed by MTT assay. Bars indicate standard deviation and (*) indicates p<0.05, (n=6).

3T3 fibroblasts were cultured in Matrigel™ with PEGDA MRS of different stiffness (2 kPa, 20 kPa and 50 kPa) at an initial MRS to cell ratio of 1:5 for five days. The 3T3 cells and MRS directly interact and stretch along and across MRS in a similar manner (data not shown). A MTT assay was used to assess proliferation of 3T3 cells in 3D Matrige™ gels with MRS of varying stiffnesses (FIG. 17). This data show that gels with stiffer MRS (20 kPa and 50 kPa) significantly downregulated fibroblast proliferation compared to gels with no MRS. Soft MRS (2 kPa) appear to have a lesser effect (not statistically different) on fibroblast proliferation. This response to the stiffer MRS suggests that a reduction in cell proliferation may be associated with an alteration in mechanotransduction; cells attached to stiffer MRS generate a mechanical force that results in changes in cell proliferation.

In addition to cell proliferation, MRS also affect gene expression and matrix production in a three dimensional system. 3T3 fibroblast were cultured as described above with different stiffnesses of MRS (2 kPa, 20 kPa and 50 kPa). Quantitative PCR was used to investigate expression of type I collage, type IV collagen, $\alpha$-SMA and integrin $\alpha$-3. The latter two cell markers are elevated post myocardial infarction (FIG. 18). Type I collagen gene expression was downregulated in 3T3 cells cultured with all three MRS stiffnesses, suggesting that MRS can be used to modulate extracellular matrix synthesis. Conversely, cultures with soft MRS showed no significant difference on the expression of type VI collage, $\alpha$-SMA or integrin $\alpha$-3 compared to cultures with no MRS. However, fibroblasts seeded with stiffer MRS (20 kPa and 50 kPa) showed downregulation of type IV collagen and $\alpha$-SMA, with the most pronounced effect being observed in the 20 kPa MRS system. Likewise, the adhesion molecule integrin $\alpha$-3 was only downregulated in cultures with 20 kPa MRS. This data suggest that MRS of muscle-like stiffness (~20 kPa) could provide structural support that prevents fibroblasts from acquiring a more fibrotic state, therefore limiting deposition of matrix molecules.

Microrod Stiffness and Contractile Isoforms and Junctional Proteins for NRVM

NRVM maturation is characterized by the molecular diversity of myofibrillar isoforms, e.g. the troponin I (TnI) isoform transformation from the slow skeletal (ssTnI) to the cardiac (cTnI) isoform and from the $\beta$- to $\alpha$-myosin heavy chain (MHC) (Schiaffino, 1996). In the whole heart, the intercalated disks strengthen the mechanical adhesion between myocytes allowing for transmission of force between contractile units while the electrical gap junctions ensure synchronicity by allowing the depolarization wave to pass from one cell to its neighbor. Western blots are used to visualize the focal adhesions and mechanical junctions by n-cadherin, vinculin and paxillin. The quantity and distribution of electrical gap junctions are observed with antibodies to connexin 43, the major gap junction protein in the heart. Morphometric studies of junctions for MRS of different stiffness are made for NRVM, identified by desmin counterstaining (Motlagh, 2003; Boateng, 2003).

The aforementioned methods have been employed as follows.

Microrod Fabrication

Figure 1:
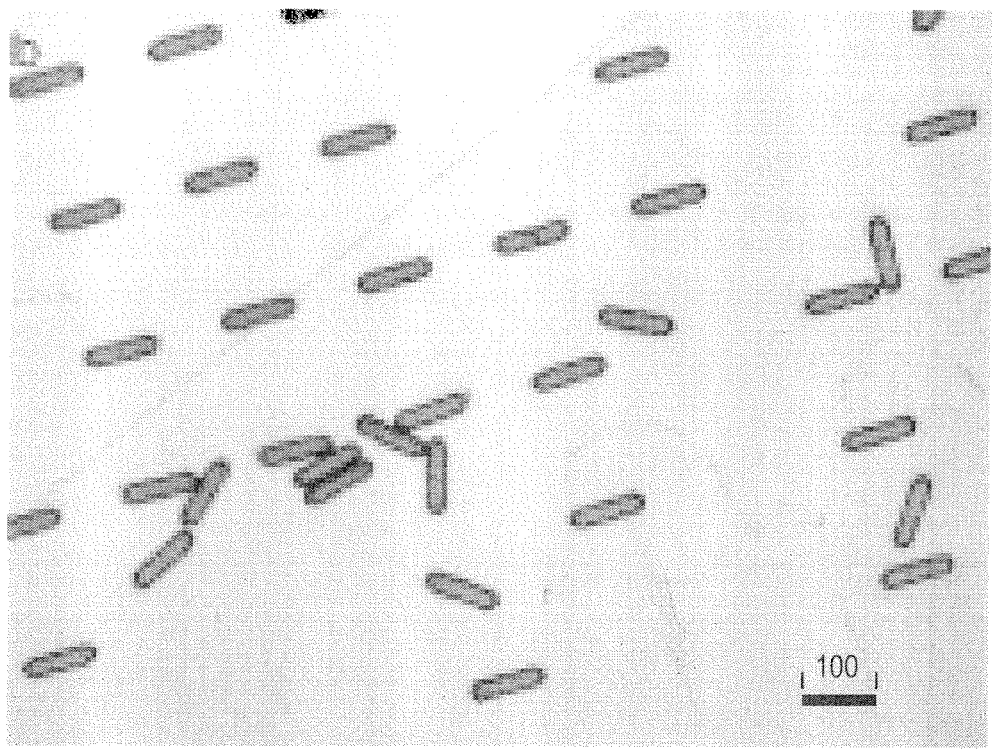
FIG. 1. shows a bright-field image of polymer microrods on wafer showing some released while others are still attached.
Figure 5:
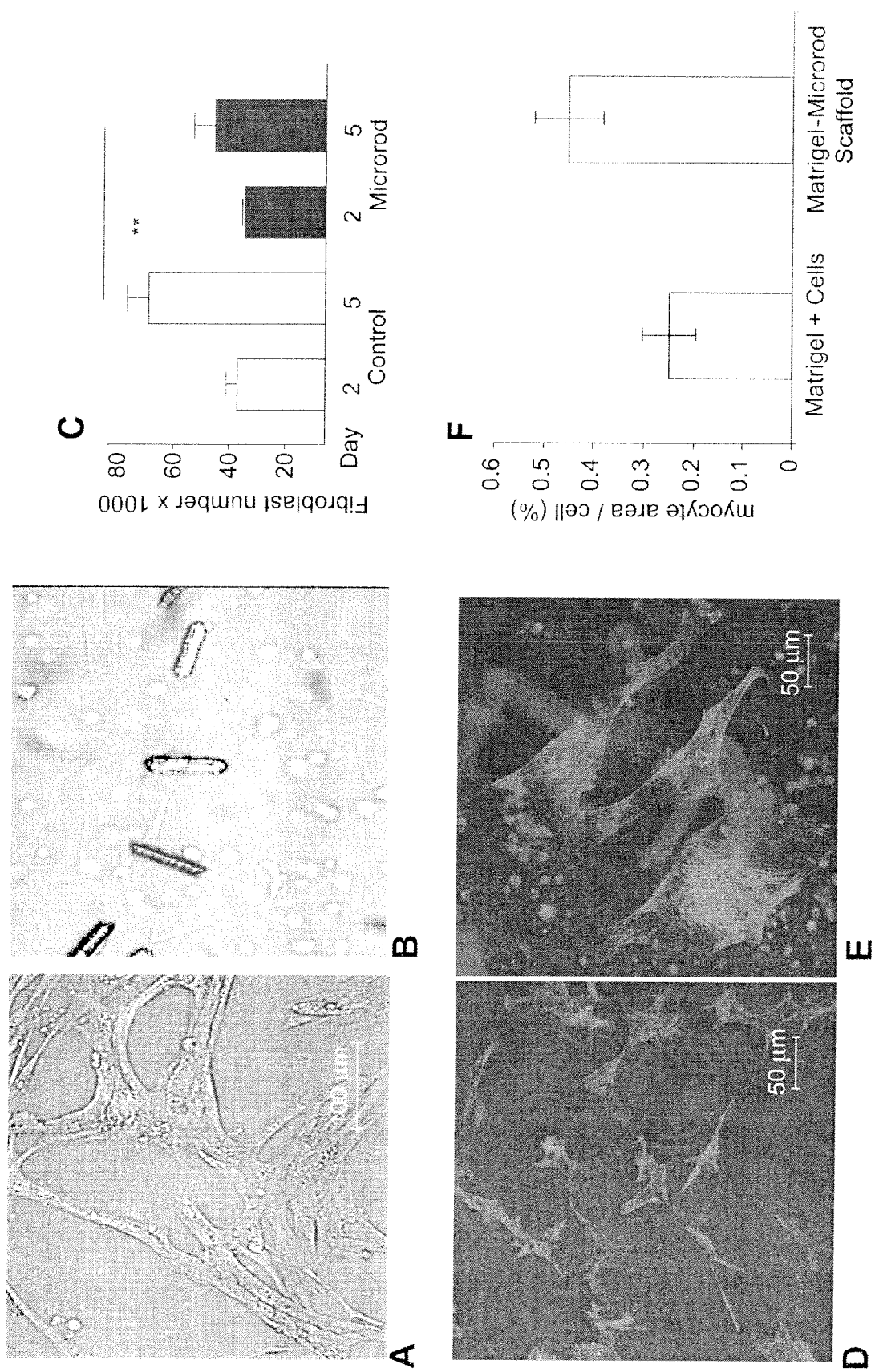
FIG. 5. shows microrods (100 µm long) retard the proliferation of fibroblasts and increase myocyte size compared to growth in Matrigel™ alone.

Microrods (MRS) were created in a variety of polymeric materials, including biodegradable materials, using soft lithographic techniques previously developed (Deutsch-Snyder and Desai, 2001; Tao and Desai, 2005). Using this approach, rod-like structures were molded from a master template in a biodegradable polymer such as poly-lactic-acid, poly-glycolic acid or co-polymers whose features slowly degrade over time when incubated in warm, physiologic solution. MRS were designed to be ~100 µm long with a 15 µm×15 µm cross-section (FIG. 1). After mixing the MRS into Matrigel™, a commercial hydrogel, (BD Biosciences, Bedford, Mass.) and allowing it to set, the MRS had a random organization and distribution throughout the gel (FIG. 5). To ensure that the bulk properties of the gels, such as stiffness, are not changed by the inclusion of microrods, a parallel plate rheometer was used to examine gels with varying concentrations of MRS. Matrigel™ alone is a soft gel with a low shear modulus of 34 Pa (Semler, 2000). The values of G' and G" for Matrigel™ with MRS were not significantly different from Matrigel™ without MRS of varying concentrations.

Figure 2:
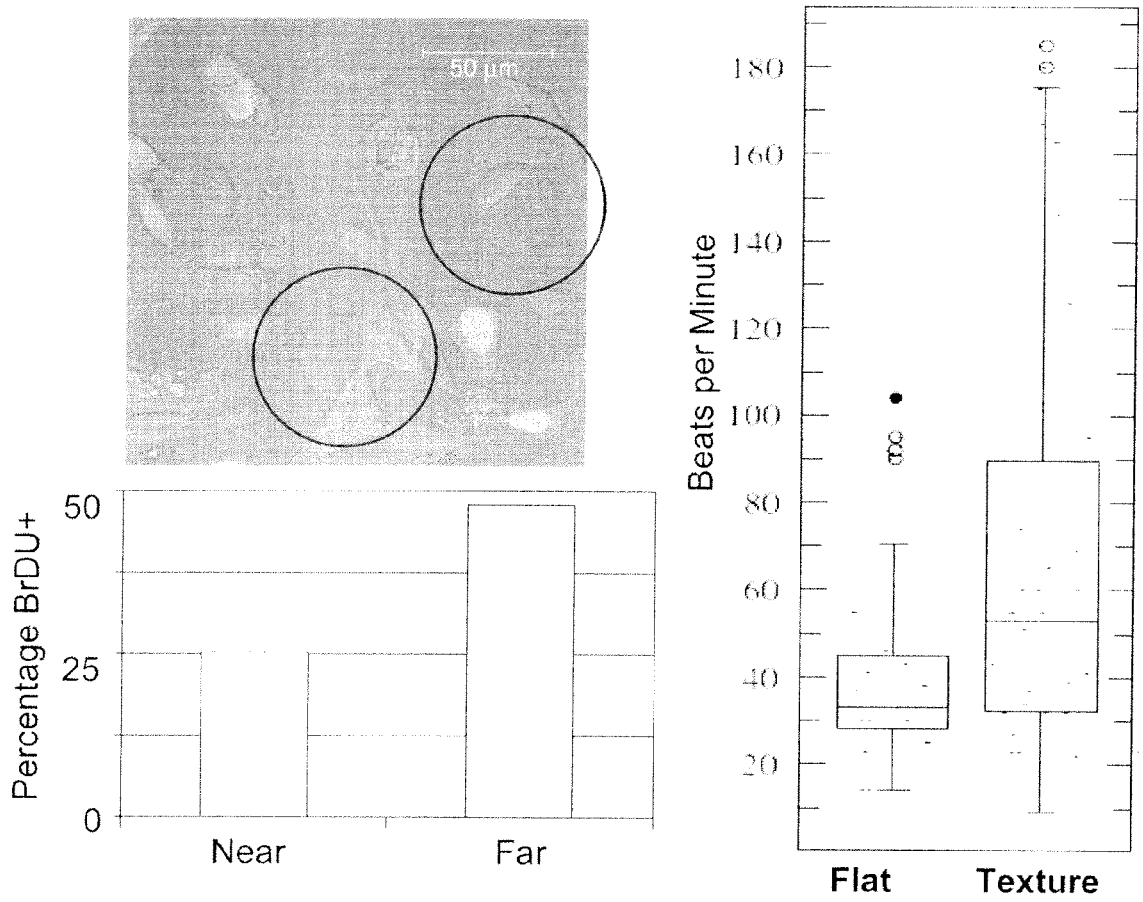
FIG. 2. shows microprojection effects on immature stem cell DNA replication as well as range and rate of beating.

Studies on cardiac stem cells interacting with suspended microrods were carried out (FIG. 2). Heterogeneous mouse embryonic stem cells of the R1 were grown on 15 µm high microprojections made in poly-dimethyl-silicone (PDMS) membranes (FIG. 2). The majority of dividing cells were non-myocytes detected by 5-bromo-2-deoxyuridine, BrDU incorporation in cells undergoing DNA replication. Individual cells partially wrapped around the microprojections and many were myocytes ($\alpha$-actinin stain, not shown). The beating rate per minute of the cardiomyocytes was recorded by video microscopy as 1.8±0.4 fold higher on the microprojections compared to the flat with surprising changes in coefficients of variance of 0.50 and 0.21 respectively (n=5). These results suggest that microtopography limits cell expansion and alters beating characteristics of stem cell progeny.

Figure 3:
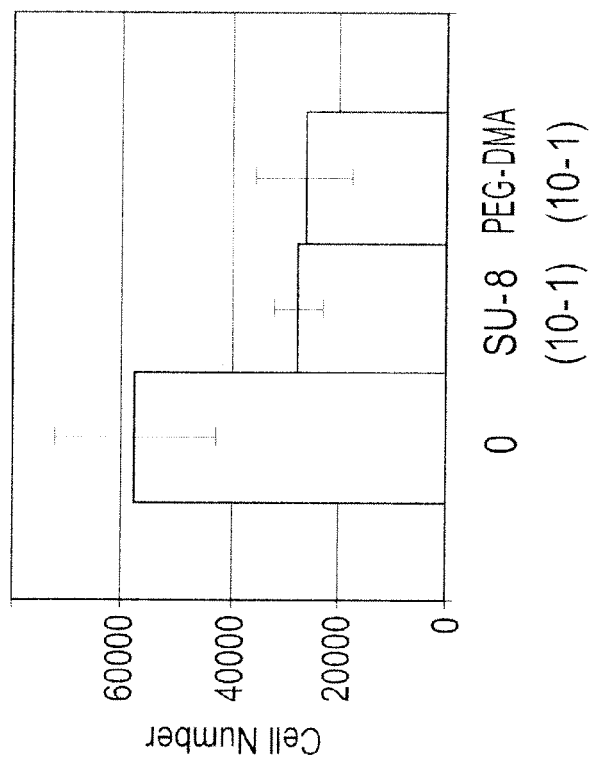
FIG. 3. shows the effect of microrod stiffness on 3T3 cell proliferation in a 3D gel.
Figure 3:
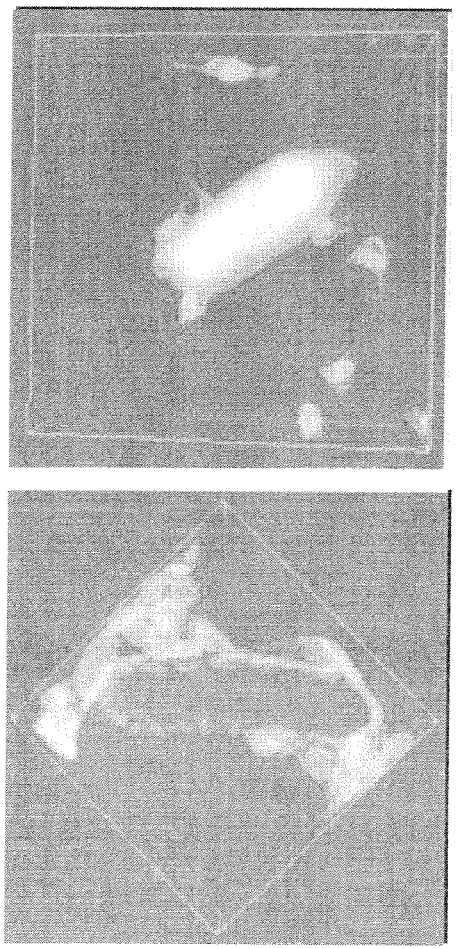

Fibroblasts also interact with SU-8 microrods suspended in gel (FIG. 3) and PEGDA microrods of two different concentrations (FIG. 3). In a 1 mm-thick layer of Matrigel™, fibroblasts migrated and spread in a manner typical in culture. However, inclusion of microstructures dramatically changed both the appearance and proliferation of the fibroblasts. Polarized fibroblasts interacted with microrods by attaching, spanning to another microrod, or growing alongside with the long axis of the cell following the long axis of the rod. A few cells had no interaction with the microrods. Cell number was counted after release from the Matrigel™ by BD Biosciences Cell Recovery Solution and hemocytometry, or the WST-1 colorimetric assay (Roche Applied Science, Manheim, Germany) where absorbance (abs 450-abs 630) directly correlated to the number of viable cells. Cell division was rapid for cells suspended in Matrigel™ alone but reduced significantly by the inclusion of 100 µm SU-8 or PEGDA microrods. Fibroblast proliferation decreased in the presence of the microrods. Fibroblast proliferation was affected by both SU-8 (FIG. 3A) and by PEGDA (FIG. 3B) microrods, two materials with different chemical properties but similar microarchitecture.

Mouse bone marrow mesenchymal cells (mBMSC) were plated in Matrigel™ with and without microrods (FIG. 4A). Phase contrast images show that mBMSC migrated to and aggregated around microrods of higher stiffness than the surrounding gel, i.e. mechanotaxis with different morphology.

Figure 4:
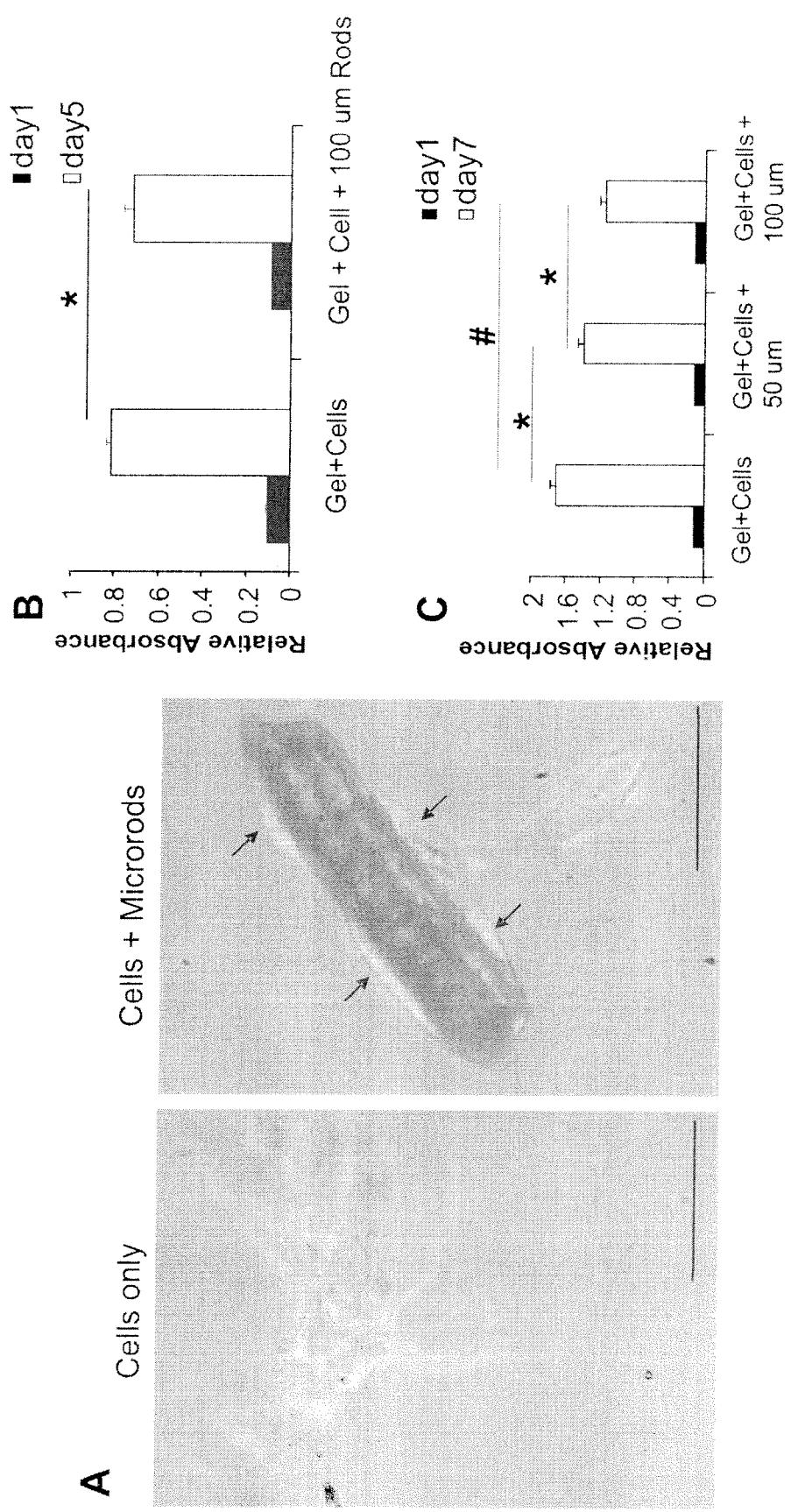
FIG. 4. shows the effect of microrods on mouse bone marrow mesenchymal cell (mBMSC) proliferation.

The WST-1 assay determined the relative absorbance over Matrigel™ alone (intensity of experimental wells—intensity of Matrigel™ only) and thus, relative cell number after 1 and 5 or 7 days of culture (FIG. 4 B, C). Both 50 and 100 µm microrod scaffold blunt proliferation is detected, but this effect was greater for longer microrods.

Studies on neonatal rat ventricular fibroblasts (NRVF) interacting with polymer microrods suspended in gel were carried out (FIG. 5). In a 1 mm-thick layer of Matrigel™, fibroblasts migrated and spread in a manner typical in culture (FIG. 5A). However, inclusion of microstructures dramatically changed both the appearance and proliferation of the fibroblasts. Polarized fibroblasts interacted with microrods by attaching, spanning to another microrod, or growing alongside with the long-axis of the cell following the long-axis of the rod (FIG. 5B). A few cells had no interaction with microrods. Cell number was counted by release from the Matrigel™ by BD Biosciences Cell Recovery Solution and hemocytometry, or the WST-1 colorimetric assay (Roche Applied Science, Manheim, Germany) where absorbance (abs450-abs630) directly correlates to the number of viable cells. Cell division was rapid for cells suspended in Matrigel™ alone but reduced significantly by the inclusion of 100 µm SU-8 microrods (FIG. 5C). Similarly, neonatal rat ventricular myocytes (NRVM) were cultured in Matrigel™ with or without microrods. In gel alone, NRVM remain atrophic, stellate, angular and beat very weakly (FIG. 5D). However, when microrods were present the NRVM are hypertrophied, and formed clusters that beat vigorously (FIG. 5 E,F). NRVM were able to move the microrods in Matrigel™ like a pendulum with a steady detectable rhythm. NRVM also spanned two SU-8 microrods with strong anchorage (data not shown).

Example 2

MRS Stiffness and NRVM Retention of the Organization and Cell Connectivity as the 3D-architecture Degrades Microengineered systems can be made to degrade over an intended time period. Given the appropriate biomaterial one can observe long-term maintenance of cellular organization with and without structural cues. The ability to microfabricate structures out of biodegradable materials (a PLGA co-polymer blend) (FIGS. 1 & 2; Snyder and Desai, 2001) and have achieved short-term cell organization has been demonstrated.

Control of Degradation by Selection Materials

MRS are manufactured from biodegradable materials instead of traditional microfabrication polymers such as PDMS or SU-8 to assess survival of tissue architecture after the topography disappears. Factors such as molecular weight, exposed surface area and crystallinity affect degradation rates (Lanza, 2000). Also, processing conditions have can alter degradation characteristics of a material. For instance, heat molding can accelerate the degradation rate (von Oepen, 1992). Substantial degradation of a microstructure takes about a week in PGA and 3 weeks to a month on PLA (Snyder 2001). Therefore, a PLGA co-polymer blend is used.

Time Course of Degradation of PLGA Scaffolds In Vitro

The degradation properties of PLA, 25:75 PLGA, 50:50 PLGA, 75:25 PLGA, and PGA (listed in order from slower to faster degradation rate) are examined to select the appropriate scaffold material. The stability of MRS are tested in three ways: 1) by looking at wet and dry weight over time; 2) by determining the feature size using scanning electron microscopy over time. To determine biodegradation, initial length, width and thickness of the MRS (approximately 100 microns long and 15×15 µm cross section) are measured. Next, initial weight of the substrata are measured; and 3) MRS are suspended in 3D gels with PBS (pH ~7). The dishes are placed in a 37° C. incubator and the PBS changed regularly to simulate tissue culture conditions. Scaffolds are observed for weight, thickness, width and length loss at different time intervals every 24 hours (Kim, 2003; Wilson, 2002). This is repeated every 3 days over the 2-week period. These experiments establish a time course for degradation of the different polymer mixtures discussed above. The optimal material concentration is one in which the microscale features degrade in the two week time frame and is biocompatible and non-toxic to the NRVM and NRVF.

Tissue Architecture, Electrical Communication and Synchronous Beating

The effects of degradation of MRS in 3D gel on the primary culture cell mixture of NRVM and NRVF are monitored using polymer or co-polymers optimized as described above. Myocytes are observed to see how they affected over a 2-week time course of MRS degradation using time-lapse video of living cells to observe synchronicity and strength of beating throughout the scaffold. Cell-to-cell arrangements are monitored with samples taken at 1, 3, 7 and 14 days in 3D gel cultures, and special attention is paid to the regions adjacent to the MRS. We also determine if cells are striated and spontaneously beating in a synchronous manner around the MRS. Assessment of cell type is made by confocal immuno-microscopy as above, using α-actinin to identify NRVM and procollagen for NRVF, respectively. Cell junctions, sarcomeric architecture of NRVM are delineated by the same set of immunochemical markers used previously with confocal analysis.

The aforementioned methods have been employed as follows.

Degradation of Microtexture

Figure 6:
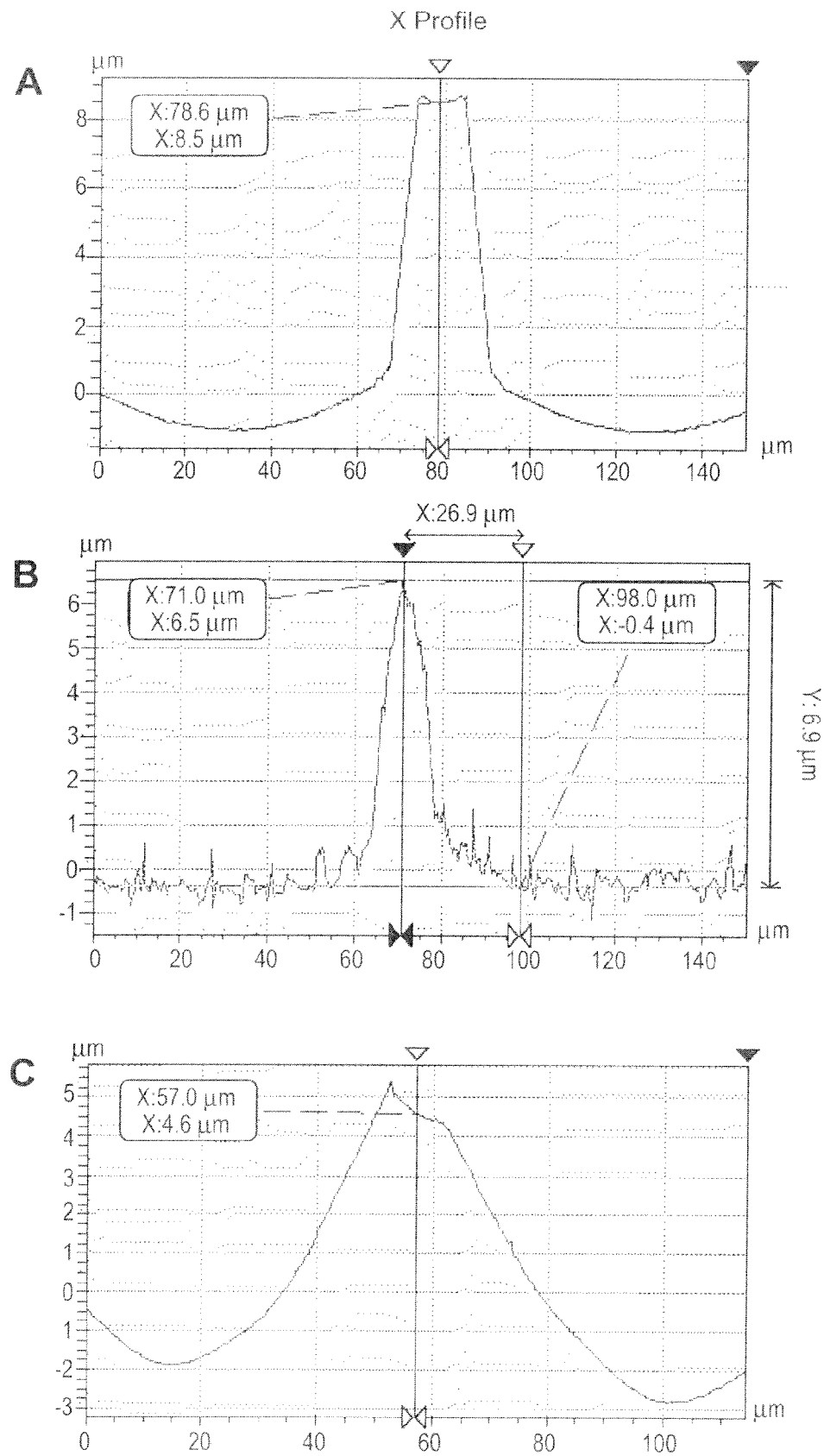
FIG. 6. shows a time course of degradation of a PGA micropeg as example for expected microrod degradation.

Biodegradable, biocompatible, deformable grooved substrata (10 µm trench and mesa, 5 µm deep groove, 15-20 µm thick layer) were prepared from PLA, PGA, or PLGA. The surface was sterilized in 70% ethanol, coated with laminin and seeded with NRVM at 500,000/cm$^2$. This membrane floats so it is weighted down. After four days in culture, the NRVM were fixed and processed for immuno-localization. Degradation of microtexture was seen when incubated in DMEM culture media at 37° C. over a period of 7 days. The initial height was 8.5 µm as seen in the X-profile. After 4 days, the height decreased to 6.5 µm. Finally at 7 days, features were ~4.6 µm in height. Such slowly degrading microstructure was useful in our tissue engineering or drug delivery platforms (FIG. 6).

Example 3

Effects of Microscaffolds Contractile Maturation and Proliferation on Mouse Embryonic Stem Cell Derived Cardiomyocytes (ESCM)

ESCM

Although cell-cell or cell-ECM interactions are important, how changes in the physical niches affect the differentiation capacity of these cells and their potential to form viable, robust cardiomyocytes remain unknown. The niche in which stem cells reside and differentiate is a complex physico-chemical microenvironment that regulates cell function. The role played by three-dimensional physical contours was studied on cell progeny derived from mouse embryonic stem cells using microtopographies created on PDMS (poly-dimethylsiloxane) membranes. While markers of differentiation were not affected, the proliferation of heterogeneous mouse embryonic stem cell-derived progeny was attenuated by 15 m-, but not 5 m-high microprojections. This reduction was reversed by Rho kinase and myosin light chain kinase inhibition, which diminishes the tension generating ability of stress fibers. Purified cardiomyocytes derived from embryonic stem cells also showed significant blunting of proliferation and increased beating rates compared with cells grown on flat substrates. Thus, proliferation of stem cell-derived progeny appears to be regulated by microtopography through tension-generation of contractility in the third-dimension. These results emphasize the importance of topographic cues in the modulation of stem cell progeny behavior. This data is described in Biehl et al., *Developmental Dynamics,* 238: 1964-1973, 2009, and is incorporated by reference herein in its entirety.

Mouse ES Cell Derived Cardiomyocytes (ESCM)

The well-established R1 ES cell line is used and can be grown indefinitely to derive a heterogeneous cell population, including cardiomyocytes (ESCM), see reviews (Boheler, 2002; Wobus, 2002; Boheler, 2003; Caspi and Gepstein, 2004; Wobus and Boheler, 2005). The wild type R1 cells are used to form an embryoid body by the hanging drop method and suspended for 2 days. Cells are dispersed and plated and after 2-3 days, clusters of beating cells are dissected, dispersed by 15-20 minutes in collagenase, spun and replated on gelatin coated dishes. These are allowed to attach, and additional media is added. Cells are cultivated and observed over the following week, and used over 2-4 weeks. A heterogeneous cell population of cells is derived that includes cardiomyocytes.

ESCM and General Bioengineering Approach

ESCMs are in the 10 μm size range and, based on our previous findings, microstructured features in the cell size range are recognized and effective in regulation. ESCM are grown in 3D gel with or without MRS. Thus, cell responses can be separated due to the MRS stiffness from those due to the 3D gel. Cells are grown on non-textured, flat PLGA surfaces as an additional 2D control. Gene expression is attainable with RT-PCR with specific primers used on cells isolated by laser trap.

Affect of MRS in 3D Gels on Proliferation of Cells from R1 ES Line Cell

All of the heterogeneous cell types in the culture can divide, including early myocytes, unlike their adult counterparts. MRSs of different stiffnesses are used to quantify blunting of proliferation of non-cardiomyocytes from the heterogeneous population of ES cells, using desmin and α-actinin as muscle specific markers to identify the ESCM. Specifically, BrDU is used to compare the extent of cell proliferation of cells near the 3D microscaffolds with those distant or grown on flat surfaces. The WST-1 colorimetric assay is used to assess the overall proliferation of cells on MRS in 3D gel vs. gel alone. All experiments are repeated at least five times for statistical analysis.

Affect of MRS in 3D Gel on Contractile Maturation of ESCM from the Mouse R1 ES Line Cell Beating rates provide indices of contractile maturity and are used to guide study of development and organization of the sarcomeric structures. Cells are fixed, permeabilized and stained and traditional immunochemistry used to compare cells near the 3D MRS gels with those in 3D gel alone. Myofibrils and sarcomeres are evaluated by myosin, α-actinin and actin stains. The progression of early contractile isoforms is well known to provide useful information about the maturation of the myocyte early in cardiogenesis (Schiaffino, 1996; Westfall, 1996). The maturation level of ESCMs is assessed using quantitative RT-PCR to determine the levels of cTnI and ssTnI isoform expression in ESCMs at 2 and 7 days after exposure to MRS on varying stiffness.

Affect of MRS in 3D on Calcium Handling

The sensitive immunochemical approach assesses distribution of proteins (such as phospholamban, calsequestrin) in ES cells at various locations near or distant from MRS. The phospholamban transcript is present several days after the initiation of spontaneous contractions, while the SR calcium binding protein calsequestrin (Casq2) is expressed at a much later time point (~day 14 after EB plating). The physiologic transcript profile in vivo is mirrored for the proteins, such as phospholamban, and Casq2 (Fu, 2005). Data suggest that SR maturation occurs only with continued in vitro developments (Boheler, 2002; Yang, 2002; Sauer, 2001).

Affect of MRS in 3D Gel on Electrical and Adherens Cell Junctions

Using the data from the beating studies and contractility as a guide, time points are selected for a more penetrating analysis of the cell junctions. Topography may provide a spatial and physical niche that mimics a remodeling process for many proteins that occurs with the heart's maturation (Spach, 2000; Angst, 1997), e.g. gap junctions and connexin 43 expression increases sharply during embryonic stages (Fishman, 1991). Focal adhesions are detected (n-cadherin, vinculin, paxillin), and connexin 43.

The aforementioned methods have been employed as follows.

Cardiac Stem Cells

Figure 7:
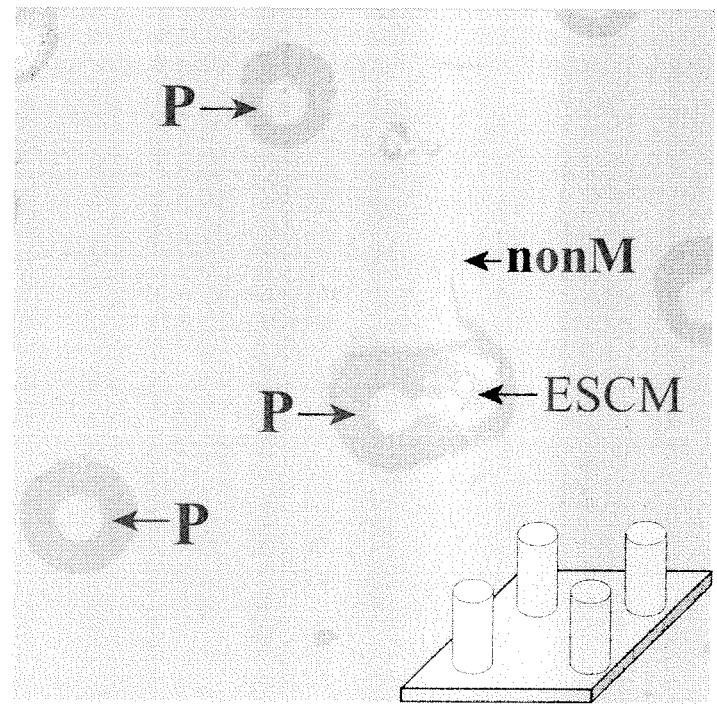
FIG. 7. shows myocyte-positive mouse embryonic stem cell derived cardiomyocytes (ESCM) cells.

Cardiac stem cells were derived from the R1 ES cell line and grown on microtextured surfaces and had distinct morphologies depending on attachment to the micro-projections (FIG. 7).

Cells Near Microprojections

Individual cells partially wrapped around the microprojections and groups of cells tended to cluster and form mushroom-like caps that beat in a range from 30-90 bpm (typical 60-80) 12 days after embryoid body (EB) formation (7 days before and 5 days after plating). Isolated cells and beating clusters looked like cardiomyocyte (CM) clusters contained within intact and plated EBs, where CM proliferation occurs during early stages of differentiation and spontaneous contractions are maintained for weeks. Cells on flat surface had a flattened morphology and tended to beat arrhythmically and much more slowly (ranging from 7-30 bpm). Thus, attachment of ES cells to the microprojections allowed ESCM to be derived and affects contractile properties.

Bone-marrow-derived Mesenchymal Stem Cells

Bone-marrow-derived mesenchymal stem cells (MSCs) are self-renewing cells that retain their ability to differentiate into mesenchymal tissue including bone, cartilage and adipose tissue as well as skeletal muscle cells, liver cells, neural cells, smooth muscle cells and fibroblasts. These properties make MSCs an attractive cell source for regeneration of damaged tissue. In a recent publication, Collins et al., *Small,* 2009 (E-pub ahead of print; DOI: 10.1002/smll.200901757; PMID: 19943257), human MSC function was assessed in manipulated 3D microenvironments. Collins et al. is incorporated by reference herein in its entirety.

Photolithography was used to fabricate MRS (100 μm long and 15 μm$^2$ cross section) of SU-8 photoresist material for culture in a 3D Matrigel™ environment. hMSCs with or without MRS are uniformly distributed throughout this 1-2-mm-deep matrix. hMSCs spread out with fingerlike projections between days 1 and 2 with this morphology persisting throughout the 10 day culture period. The cell body spreading and area of hMSCs are smaller in 3D matrix than when grown on 2D tissue culture plastic. hMSCs begin noticeable interaction with MRS as early as day 2, which becomes more pronounced between days 5-6. The hMSCs are flattened, more polarized, and less stellate-shaped with MRS compared to without (data not shown). The decreased number of fingerlike projections suggests less active filopodial activity, which likely coincides with decreased motility. Cells have decreased rates of motility on large expanses of hard substrates compared to softer substrates, and apparently the small contact area presented by the microstructure surface acts in a similar manner.

Cell proliferation in 3D hMSC cultures increased approximately 3.3% due to microdomains of stiffness introduced by MRS within the gel. Equal cell numbers resulted on the bottom surface of the dish with or without MRS in the overarching gel. Thus, the MRS appeared to induce increased proliferation of hMSCs. This was further probed by analysis of cell cluster size at both days 5 and 10. Cluster size and distribution are both larger with MRS than in the gel alone at days 5 and 10.

Microarray experiments also revealed many transcript-level differences between hMSCs cultured in 3D gel alone and in 3D gel with MRS. Raw p-values revealed 1659 significantly differentially expressed transcripts that can be grouped by hierarchal clustering into enriched functional groups including cell adhesion, developmental process, actin cytoskeletal organization and biogenesis and cell proliferation (Collins et al., 2009, Table 1). Twenty-two genes (including 60 of 88 probe sets) showed trends for decreased expression of a bone development program with MRS. Altogether the data show that after ten days of culture, MRS in a 3D gel decrease or slow hMSC bone differentiation with gene expression profiles approaching the early expression levels seen in hMSCs in 2D culture at two days. This decreased differentiation likely corresponds to the increased proliferation of hMSCs with MRS. Taken together, these data demonstrate that optimization of MRS topography and stiffness coupled with growth factor incorporation and release is capable of improving stem cells properties for regenerative therapy.

Example 4

Encapsulation Efficiency, MGF E-domain Biostability, and Acellular Release Kinetics from the Microrod Scaffolds This Example permits verification of optimal formulation of MRS, time-release properties, ratios of MRS/myocyte, dosage of MGF. Biodegradable, PLGA-based microspheres have already demonstrated their potential for GF delivery in tissue equivalents (background). Protein release profiles from PLGA microspheres result from the interplay of drug diffusion through the polymeric time-evolving matrix, internal morphology of the system, and polymer erosion (Crotts, 1998; Ungaroa, 2006). In aqueous environments, water rapidly hydrates the particle and drug diffusion occurs through the innate PLGA micropores (angstrom- or nanometer-dimension) and the macroporous structure of the particle. In the case of growth factors, the diffusion through the polymeric matrix is prevented until micropores grow in size and/or coalesce because of polymer erosion (i.e., mesopore formation) (Ungaroa, 2006). Release rates can be generally regulated by selecting adequate formulation conditions (e.g., polymer type and concentration), which affect initial hydration phase, internal morphology and erosion rate of the matrix (Tracy 1999, Lemaire, 2003). In the case of our MRS scaffolds, the shape of the structure and the hydrophobicity of the growth factor may also affect the release kinetics and should be taken into account. Furthermore, the knowledge of protein concentration gradients realized within the scaffold is crucial to effectively direct neo-tissue growth. Therefore, we propose to first study acellular release kinetics of free floating and matrix incorporated MRS.

Microrod Master Template

The methods used to create MGF loaded PLGA MRS are similar to those described for unloaded MRS above. After the PDMS MRS master is created via soft lithography, MGF-PLGA solution is deposited on the PDMS mold and placed under vacuum to displace trapped air. MGF-PLGA solution is obtained by dissolving MGF and PLGA in acetonitrile to give the desired concentration. Excess PLGA is removed from the surface and a silicon wafer is placed over the mold. The mold is inverted, placed under pressure (50-150 psi) and cured at 65° C. Once cured, the PDMS mold is peeled off resulting in freestanding MRS. It is important to note that the solvent used (acetonitrile) and processing conditions are compatible with preserving MGF bioactivity as shown by the Goldspink lab as shown in preliminary data.

Growth Factor Incorporation

The incorporation (encapsulation) efficiency measures the amount of peptide loaded into PLGA MRS in relation to the initial amount of peptide in the solvent during MRS fabrication. To measure the encapsulation efficiency, MGF-loaded PLGA MRS are solubilized in appropriate solvents, which liberate the incorporated MGF molecules. The released MGF is analyzed using a customized Enzyme Linked Immunosorbent assay (ELISA). This parameter is necessary in order to calculate the equivalency of MRS and MGF doses. To measure growth factor release in a cell-free system, the released MGF from MRS in solution are analyzed using methods described in Cohen 1991. The MGF-loaded PLGA MRS is suspended in 1 mL of sterile PBS supplemented with 5 wt % penicillin/streptomycin and place in a 37° C. incubator for the duration of the study. At intervals of 1, 2, 4, 6, and 24 hours and daily thereafter, 1000 μL of eluant is collected and replaced by 1000 μL of new sterile PBS. The removed eluant is stored in two separate volumes of 250 and 750 μL for ELISA and bioactivity assays, respectively, at −80° C. until analyzed.

The aforementioned methods have been employed as follows.

Growth Factor Incorporation and Release

Figure 8:
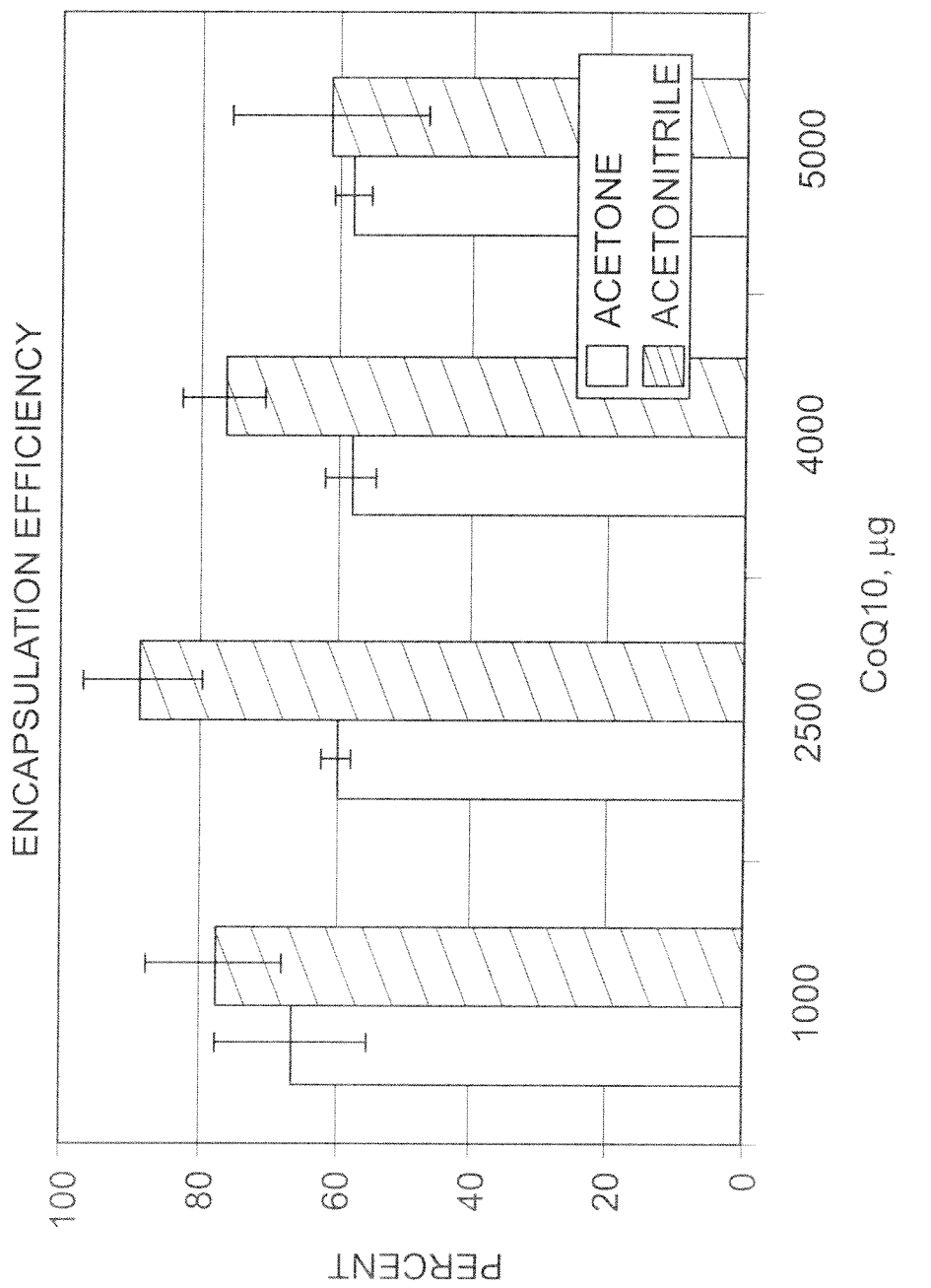
FIG. 8. shows encapsulation efficiency of drug (µg) of PLGA particles (0.4 dL/g) synthesized using acetone or acetonitrile as the solvent.
Figure 9:
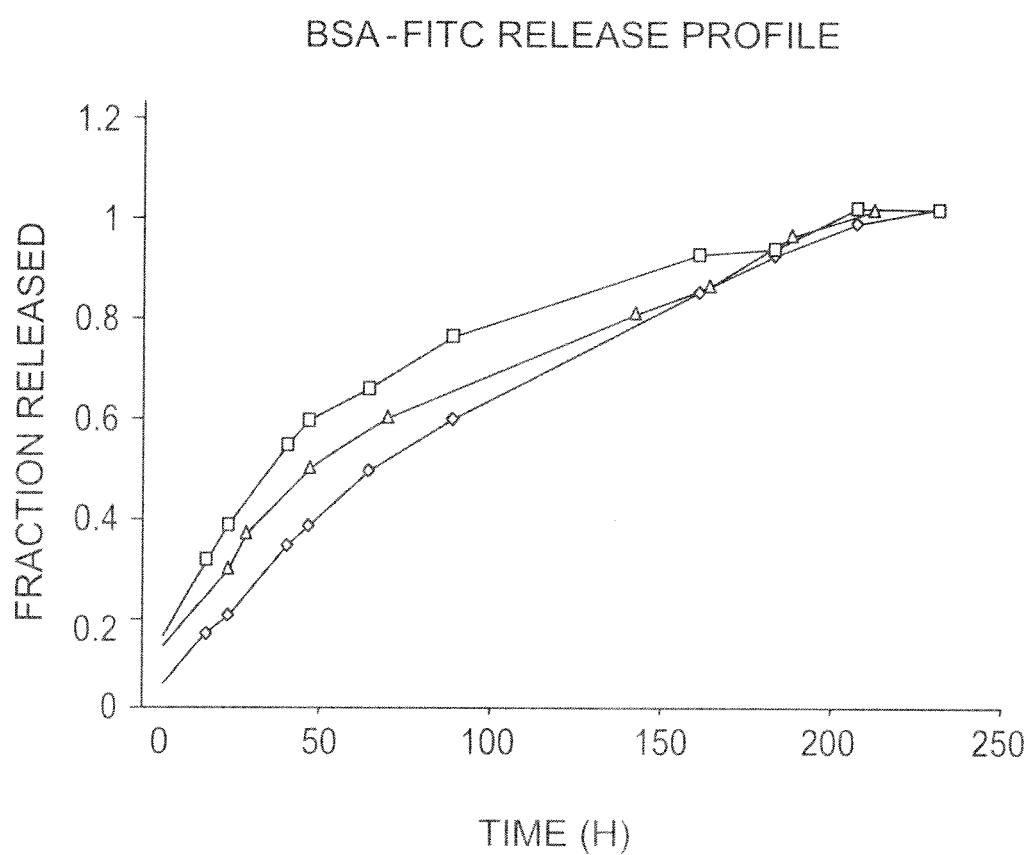
FIG. 9. shows peptide release from biodegradable microstructured films.

An excellent encapsulation efficiency of 60 to 80% was achieved for hydrophobic peptides such as MGF within PLGA particles (0.4 dL/g) synthesized using acetone or acetonitrile as the solvent (FIG. 8). Acetonitrile is an ideal solvent for both the polymer and MGF. For an initial drug concentration of 1 mg/ml, MGF loading of ~500 μg/ml microrods was achieved. Peptide release was controlled over a period of several days. FIG. 9 shows a typical release profile from peptide-containing microstructures. Preliminary cell culture assays confirmed a functional effect of the MGF released from the MGF loaded polymeric film corresponds to physiological MGF time course.

Example 5

Effects of GF Released from MRS on Normoxic and Hypoxic Myocytes

The effective delivery of MGF and IGF from MRS may permit myocytes to thrive under normal and even under hypoxic conditions. This is tested by use of the prototype MRS with the desired physiologic release profile described above to have an initial bolus within 12 hours followed by 2 week sustained release. Both the native and a stable form of the MGF E-domain, 24 amino acids, are used first and act as paracrine/autrocrine growth factors for muscle. NRVM are grown in 3D gel and introduce variable quantities of different formulations for the native or stable MGF-loaded MRS, with the necessary controls. Empty MRS are used to control for cytotoxity by the PLGA vehicle. Peptide in free solution or delivered via the MRS permits evaluation of the effect of the time-release properties of the MRS MGF level. The same amino acids in MGF are used in scrambled order as a negative control. Dishes without cells are used to confirm characteristic release properties after storage. NRVM are harvested at day 1, 7 or 14 after GF addition for assays to study short and long term effects on gene expression and apoptosis by biological evaluation methods described below. Five different cell isolations are used for statistical evaluations.

NRVM Culture and MRS Loading of MGF

The NRVM are isolated and plated in 3D Matrigel™ as above. A 100 ng/ml bolus of stabilized or native MGF E-domain peptide is pipetted directly to the media, or we add the required number of MRS loaded to attain a similar total load. Sufficient MGF can be readily loaded into each MRS so that the quantity delivered can regulate the dosage for physiologic responses. Approximately two million NRVM is used per dish in culture. Calculations and data suggest that a ratio of 1 MRS per 1000 myocytes is sufficient, so we begin in that range.

Time Profile

The native MGF peptide degrades rapidly in vitro with the majority being lost by 30 minutes and all by two hours in plasma at 37° C. Thus, the native MGF delivered in vivo would degrade before it reached its destination in underperfused regions of the heart. FITC labeled MGF is used in the MRS to characterize the time course of MGF release. Fluorometric measurements of FITC levels in the supernatant media are taken every hour for 6 hours and less frequently for the next two weeks. As a control, MRS alone is used to confirm the profile of MGF release seen in the acellular experiments described above. Thus, time profiles are collected for native or stable MGF-MRS with and without NRVM growing.

Normoxia and Physiological Growth of NRVM

Differences in elution of GF makes is measured using phase microscopy for tissue architecture of living cells in the 3D composite and also use confocal microscopy with Z-stack to determine the distribution of proteins with specific antibodies. A number of different acrylamide/bisacrylamide ratios are used to optimally separate the extracted proteins. Proteins are transferred to nitrocellulose and probed with specific antibodies using standard western blotting techniques (Goldspink 2004). Quantitative real time RT-PCR is also used to assess changes in muscle gene expression normalized to the housekeeping genes (such as GAPDH or L7) with SYBR Green detection in the LightCycler thermocycler (Roche Diagnostics). Total RNA is extracted from cells using Trizol and 100 ng of total RNA is used in each RT-PCR reaction. Quantification of the RT-PCR reaction is based upon a series of in vitro transcribed mRNA standards prepared for each gene and run along side to develop a standard curve as previously published (Goldspink, 2004). Primers for both the $\alpha$- and $\beta$-myosin heavy chains are used as indices of contractile protein expression, and the $\alpha$-subunit of L-type calcium channel for rhythmicity of beating.

Hypoxia

Stress to cardiac cells initiates the undesirable pathways for apoptosis that is protected by members of the IGF-1 family (background). Therefore, stressing NRVM and introducing a second set of MRS supplying the exogenous IGF-1 alone or co-injected the MGF MRS is performed to determine the combinatorial effects. To induce hypoxic stress conditions, NRVM in the 3D composite MRS cultures are incubated in a humidified chamber (Billups-Rothenberg Inc) with 5% $CO_2$, 1% $O_2$ and the remainder balanced with $N_2$ for 12 hrs at 37° C. In addition to studies on normoxic cells, the effect of MGF on enhanced survival and recovery is assessed by using Western blots. Pathophysiologic markers for apoptosis with antibodies detect activated Caspase-3C (18 kD cleavage fragment), Bax and Bcl-2 (Cell Signaling). Stress triggers the release of the atrial natriuretic factor (ANF) and is a widely used index of hypertrophy. Therefore, RT-PCR is used to monitor mRNA levels of ANF.

Cytotoxicity

Propidium iodide (PI) can be used to assess dead cells. PI intercalates into double-stranded nucleic acids. It is excluded by viable cells but can penetrate cell membranes of dying or dead cells. PI is dissolved in buffer at 1 μg/ml. To assess viability of cell sample, 2 μL PI stock solution are added to each well and mixed well. Samples are kept in solution at 4° C. protected from light until analysis on the flow cytometer.

Beneficial Effects to Cardiac Stem Cells of GF Release from MRS

IGF-1 has a potent effect on many stem cells, particularly those in skeletal and cardiac muscle and therefore, is tested on stem cells. It is likely that MGF is also active alone, or that it works together with IGF-1. Therefore, as described above, both MGF E-domain and IGF-1 elution on mouse embryonic stem cells are tested. For normal heart development to proceed, complex interactions must take place among cardiac-restricted transcription factors to regulate early processes of commitment and differentiation, and to promote maturation (Garcia-Martinez and Schoenwolf, 1993; Olson and Schneider, 2003; Kelly and Buckingham, 2002). Early cardiac lineage markers, Nkx2.5, GATA-4, Isl-1 are assayed after MGF treatment. The molecular markers for maturation of the contractile phenotype are TnI contractile isoforms.

ESCM with unloaded MRS or treated with MGF alone, IGF-1 alone, or MGF and IGF-1 together are compared to determine the effects on their proliferative properties, apoptosis, differentiation and maturation ability. These experiments are used to determine the time course of cardiac lineage commitment and maturation of cells. Gene expression is attainable with RT-PCR with specific primers. Immunochemistry gives individual ES cell information. At least 5 cultures are assessed for statistical analysis.

Myocyte Lineage

A shift of a subpopulation towards the myocyte lineage must be tested. For these experiments, PCR analysis is used for early cardiac lineage markers, Nkx2.5, GATA-4, Isl-1 for cells at various time points after exposure to different stiffness MRS. Comparisons are made at 2 and 7 days after GF treatment. Individual cells are also identified to determine the proportion that are muscle-positive (ESCM) in the whole population. The heterogeneous cells are fixed, permeabilized, stained and used to compare cells with or without GF MRS over the experimental time course. DNA synthesis in cells is quantified by BrDU incorporation and cells are co-stained with muscle-specific markers (desmin and $\alpha$-actinin) to identify the ESCM sub-population. Random fields are counted for total BrDU stained cells and those that are also muscle positive.

Biological Assays

Contractile maturation of ESCM is assessed as using quantitative RT-PCR to determine the levels of cTnI and ssTnI isoform expression in ESCMs at 2 and 7 days after treatment with MGF. Proliferation of mES progeny is determined with or without GF by the WST-1 colorimetric assay. Apoptosis is assessed by Western blotting for activity of Caspase-C by 18 kD cleavage fragment, annexin V and PI staining. Stem cell proliferation and cytotoxicity of ESCM in the presence/absence of MGF MRS is determined by cell number assessed by propidium iodide. These methods have been described above.

The aforementioned methods have been employed as follows.

Growth Factor Release by Stress in Culture

NRVM showed that a 1 Hz cycle 20% strain was the required stimulus for MGF expression, while the 10% strain at 1 Hz was insufficient. Thus, the expression of MGF from stressed myocytes in vitro occurred after the first 2 days of extreme work. Rest and strain groups were the same for housekeeping gene, L7, and IGF-1Ea.

Time Course of MGF Eb Domain Degradation

To determine the time course of degradation of native, highly basic 24 amino acids and the stabilized E-domain MGF peptides, 1 mg was incubated with human plasma at 37° C. Degradation was assessed by blotting with a custom made E-domain specific antibody. The stable form had an amidated C-terminal and specific arginines switched to the D-stereoisomer. The data showed that there was almost complete degradation of the native peptide by 2 hours, whereas the stabilized peptide showed little or no degradation by 24 hrs. The E-domain region of MGF is an ideal candidate for MRS therapy.

NRVM Response to MGF

Figure 10:
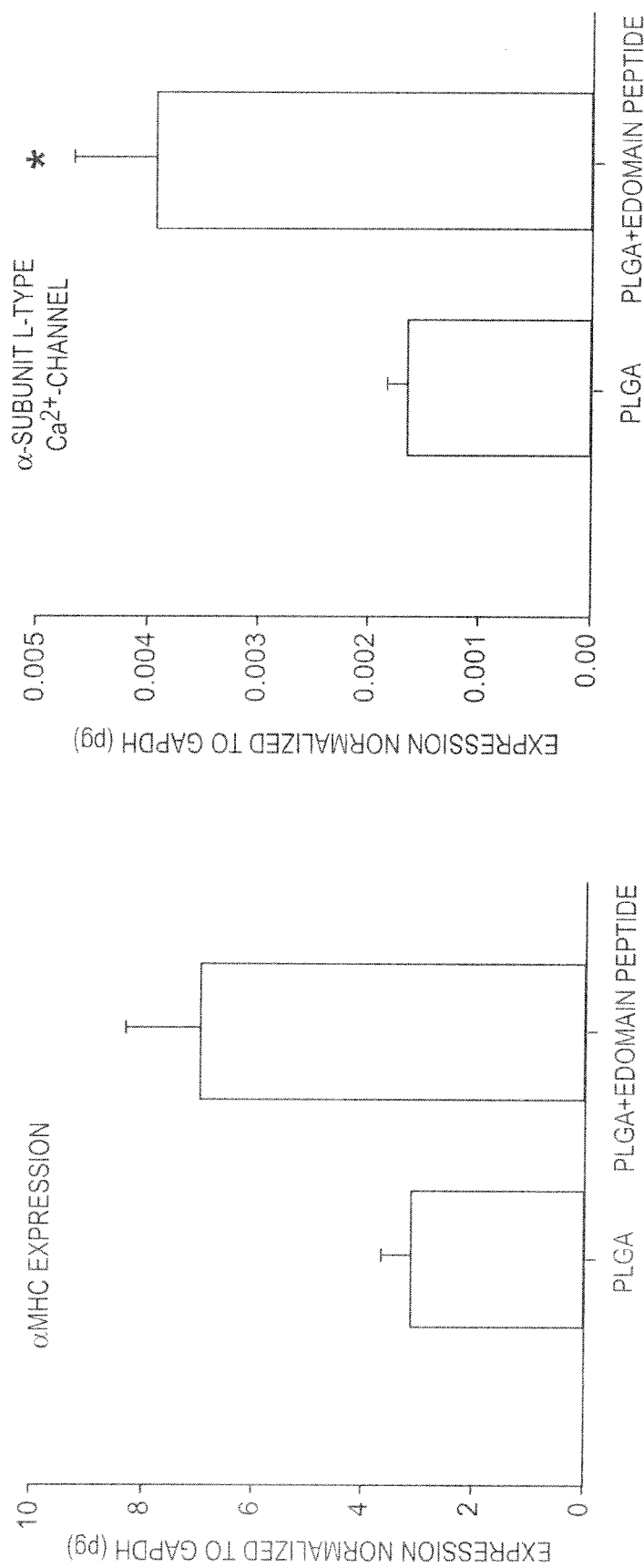
FIG. 10. shows gene expression analysis in neonatal rat ventricular myocytes (NRVM) grown for 7 days on MGF E-domain eluting sheets.

The bio-effectiveness of MGF on NRVM was demonstrated by growing them in culture on a thin film of a copolymer of polycaprolactone (PCL) and gelatin films, 10% (w/v). The stable MGF E-domain was used with NRVM plated at high density ($2 \times 10^6$ cells) on pieces containing about 50 ng MGF per dish. The tests showed that NRVM are viable, had abundant RNA and protein for analysis. NRVM were beating spontaneously and vigorously confirming physiologic function. The media was unchanged but additional media was added on day 3. At day 7 cells were lysed for protein and RNA. Analysis of physiological gene expression by quantitative real time RT-PCR showed an increase in the expression of the αMHC isoform and a significant increase in the L-type $Ca2+$-channel α-subunit) in NRVM grown on MGF E-domain eluting PCL sheets compared to PCL without peptide for 7 days (FIG. 10). This demonstrated the bio-effectiveness of the MGF E-domain peptide on NRVM. Also, note the lyophilized MGF was incorporated into biodegradable polymers and was bio-functional. The use of biodegradable microrods not only allows for injection but also provides a topographical scaffold.

Example 6

Growth Factor Delivery Via MRS In Vivo Enhances Cardiac Repair Following Myocardial Infarction Manipulation of the Microenvironment to Support Endogenous Cardiac Stem Cell Engraftment Treatment of hearts with the MGF E-domain peptide following infarction induces proliferation of stem cells with early cardiac lineage. Controlled delivery and release of the MGF E-domain peptide via the MRS may induce proliferation and mobilization of the cardiac stem cell pool and in conjunction with the 3D structure of the MRS, promotes engraftment and regeneration of new cardiac muscle cells. This combined approach of using the 3D structure and the elution of a physiologically relevant growth factor from the MRS, serves to promote stem cell therapy to rescue the infarcted heart.

Recent findings in the field have demonstrated that the functional improvement associated with the direct delivery of hematopoietic stem cells to the heart is not due to their capacity to differentiate into myocytes but rather their secretion of factors that appear to be beneficial (Fazel, 2006). Therefore, one potential mechanism that is explored is that localized delivery of the MGF E-domain improves the ability of the resident cardiac stem cells to survive (prevent cell death) in the heart following an infarction in an environment that would otherwise not permit sustained prolonged survival. The approach described herein investigates whether localized delivery of the MGF E-domain is sufficient to expand and sustain the resident cardiac stem cell population due to the release of the MGF E-domain peptide. Also, whether differentiation and regeneration into myocytes is due to their interactions with the 3D structure of the MRS is explored. As such, this novel and innovative application of the MGF eluting MRS may provide a means by which resident cardiac stem cells may be supported for therapeutic use in cardiac muscle regeneration.

To evaluate the efficacy of MGF eluting MRS, the MGF E-domain eluting MRS is administered following a myocardial infarct and determine the effects at 2 days and 2 weeks post-infarct. The effects of localized MGF E-domain delivered via MRS on the cardiac stem cell population size, distribution and interaction with the 3D MRS at 48 hours post-treatment is assessed, as is the expression of cardiac specific lineage proteins and cell-to cell contact after degradation of the MRS at 2 weeks post-treatment.

Myocardial Infarct and Administration of MRS Therapy.

Mice are anesthetized with methoxyflurane inhaled in a closed chamber and intubated with an 18-gauge angiocatheter. Surgical anesthesia is maintained using 0.5% isoflurane delivered through a vaporizer with a mixture of 95% oxygen/ 5% carbon dioxide connected in series to a rodent ventilator with the stroke volume set at 0.2 to 0.4 ml and a respiration rate of 125 breaths/min. A left thoracotomy is performed to expose the heart and the pericardium ruptured. The heart is exteriorized and the left coronary artery ligated to produce myocardial infarction. To administer the MRS therapy, the operator is blinded to which treatment is being delivered. 10 μl of MRS suspended in saline is injected into 5 sites in the ischemic LAD territory with a 27G needle (10 μL/site) 10 minutes after coronary artery ligation. The heart is replaced, a chest tube is placed in the wound and the thoracotomy closed in three layers (intercostal muscles, pectoral muscles, and skin) followed by evacuation of the chest cavity and removal of the tube. To reduce the extent of infarct variability and location, ligation of the left coronary artery as it emerges from under the left atrium will be done since it has been show to result in reproducible large infarction involving the anterolateral, posterior, and apical regions of the heart in mice (Kumar, 2005). Animals are allowed to recover in a heated cage before being returned to the animal facility. In a cohort of mice MGF-E-domain peptide are delivered via subcutaneous infusion using Alzet mini-osmotic pumps (100 μl/pump) implanted immediately after the infarct for 2 weeks. Pumps are loaded with peptide (1 mg/kg/day) dissolved in 5% mouse serum in saline and are surgically implanted and closed with a wound clip.

Following the MI and treatment at the 48 h, 2, 4 and 10-week time points, mice are euthanized with isoflurane (2%); the hearts within each group are processed and systematically analyzed as follows.

1. Immunohistochemical analysis on sections examines the expression of stem cell markers and expression of cardiac lineage specific proteins (5 hearts/group).

2. Resident stem cells are isolated from the cardiac myocyte depleted cell suspensions prepared by collagenase digestion of the heart (5 hearts/group).

3. The size and presence of the side population are determined by the Hoechst dye exclusion technique.

4. To identify the size and specific subpopulation of stem cells within the heart cells are incubated with antibodies against resident stem markers (Sca-1 and c-kit), hematopoietic markers (CD45), bone marrow markers (CD34) and cell adhesion markers (CD31) and subject to FACS analysis.

Histology and Immunohistochemistry

Routine histology is useful to determine the inflammatory responses at day 2 after injection of the MRS in vivo. Tissue architecture in the injection sites is also assessed for fibrosis and normal myocyte features at all time points. Sections are blocked with serum before incubation with primary antibodies to label stem cell markers (Sca-1, c-kit, CD45, CD34, CD31, (Pharmingen) cell cycling (Ki67 and BrdU), lineage specific proteins (NRx2.5, GATA4, Isl-1), cTnI, ssTnI, connexin 43, smooth muscle actin, and Von Willebrand factor. Confocal microscopy is used to visualize fluorescent conjugated secondary antibodies.

Stem Cell Isolation and Identification

Stem cells are isolated along with cardiac myocytes via collagenase digestion, but the isolate is then depleted of myocytes by centrifugation at 3,000 rpms for 10 minutes. Cell suspensions are incubated with 5 µg/ml Hoechst 33342 stain (Sigma) for 90 mins at 370 C in DMEM plus 2% fetal calf serum and 10 mmol/L HEPES, with (control) and w/out 0.1 mM verapamil (Sigma). Propidium iodide (2 µg/ml) is added to exclude dead cells. Cells are washed in cold HBSS before cell surface antigen staining (4° C. for 30 mins) with fluorochrome conjugated monoclonal rat anti-mouse antibodies. Flow cytometry is performed using MoFlo (Cytomation, Inc) equipped with triple lasers. Hoechst dye is excited at 350 nM using a multiline UV laser and emission collected at 405 nm (Blue) and 660 nm (Red). Phycoerythrin (PE) and PI are detected using 488 nM agarose laser. A 610 DMSP (610 nm short pass dichroic minor) is used to separate the emission wavelengths. The number of side population cells are expressed as a percentage of the isolate and the number of stem cells are expressed as a percent of the side population (Pfister, 2005).

Pathologic Hypertrophy and Early Dilation of Hearts Following Myocardial Infarction Controlled delivery and release via the MRS may provide an efficacious means for supplying the MGF E-domain peptide to potentiate the actions of the paracrine/autocrine IGF-1 and prevent apoptosis. Promoting cell survival and preventing cell death in cardiac myocytes and cardiac stem cells means more are viable and thus the need to normalize wall stress is minimized, thereby preventing hypertrophy. These changes prevent the remodeling of the heart and lead to long-term improvement in ventricular function.

In this way, the experimental approach is to administer the MGF E-domain eluting MRS following a myocardial infarct and determine the effects at 2, 4 and 10 weeks post-infarct. These time points are critical in the mouse model since they represent reproducible and measurable events that without treatment, herald the onset of the hypertrophic response (2 wks), compensatory hypertrophy (4 wks) and the decompensation to failure (10 wks). At each time point post-intervention we perform a complete analysis of the cardiac hemodynamic, geometric, biochemical and molecular data. These measures are determined relative to the administration and the actions of the MRS with or without the MGF E-domain peptide, which we predict serve as negative controls. Likewise, we compare localized delivery of the MGF E-domain peptide to localized delivery of recombinant IGF-1 via the MRS to determine whether the bioavailability of IGF-1 is improved with localized delivery. In addition, comparisons are made to the systemic delivery of the MGF E-domain via mini osmotic pumps, which serve as a positive control.

Following the stated time points (2, 4 and 10 weeks post MI), the mice within each cohort are systematically analyzed to ensure correspondence between, hemodynamic, geometric and biochemical data collection. The methodological approaches detailed below are first for the assessment of cardiac function in vivo and then for the molecular and biochemical studies.

1. Analysis of cardiac function is derived from the pressure-volume loops in instrumented animals.

2. Echocardiography is used to examine both the structural and functional changes within each group.

3. Following physiological measurements, hearts are removed for the determination of the heart weight to body weight ratio.

4. In one subset of the mice, ventricular tissue is used for quantification of the infarct size, histological analysis near MRS injection site, analysis of apoptosis using TUNEL staining and immunohistochemical staining.

5. In the other subset, RNA is extracted for analysis of gene expression using real time RT-PCR and protein expression evaluated using Western blot analysis.

Pressure-volume Loop Analysis

Cardiac functional studies in vivo require insertion of a 1.4 French pressure-conductance catheter (SPR-839, Millar Instruments, Houston Tex.) into the right carotid artery and fed retrogradely into the left ventricle, as previously published (Goldspink 2004).

Echocardiography

Echocardiography is used to examine the geometric changes of the heart. Transthoracic two-dimensional targeted M-mode and pulsed-wave Doppler echocardiography is performed with a 15-MHz linear array transducer attached to a *Sequoia* C256 system. Images of the left ventricle, LV, are taken from the parasternal short axis view at the level of the papillary muscles and LV internal dimensions are measured at the end of diastole and systole according to the American Society of Echocardiography leading-edge method on the M-mode tracings (Sahn, 1978). The LV fractional shortening (FS, %) is calculated from digital images as (LV end-diastolic dimension–LV end-systolic dimension)/LV end-diastolic dimension×10–2. Velocity of LV circumferential fiber shortening (Vcf, sec–1) is calculated as FS/LVET, where LVET=LV ejection time derived from the Doppler recordings from the ascending aorta. Stroke volume (SV) is calculated as product of main pulmonary artery (MPA) mean velocity time integral (VTI) and corresponding MPA mean cross sectional area. Multiplying SV by heart rate yields cardiac output (CO). All calculations are made from at least three consecutive cardiac cycles (Goldspink, 2004).

After euthanasia of the mice with an overdose of isoflurane (2%), the following structural, biochemical and molecular assays are done. The hearts are removed for determination of the heart weight to body weight ratio, followed by subsequent molecular and biochemical analysis. Mice are divided into two subsets (6 in each group). In one group, hearts are fixed and used for histological analysis of the effects of the MRS in the tissue, quantification of infarct size, analysis of apoptosis with TUNEL staining. In the remaining group, myocytes are freshly isolated and processed for analysis of apoptosis using FACS plus gene and protein expression analysis.

Infarct Quantification

The abdominal aorta is cannulated, the heart(s) arrested in diastole with KCl, and then perfused with 10% (vol/vol) formalin at a pressure equal to the in vivo measured end-diastolic pressure. The left ventricular intracavity axis is measured, and three transverse slices from the base, mid-region, and apex are fixed, dehydrated and embedded in paraffin for sectioning. Sections are incubated with triphenyltetrazolium chloride (TTC) (20 mins, 37° C.), which permits clearer discrimination of the various regions. The tissue in the center of the infarct zone is white, whereas the healthy tissue distal to the infarct zone has the typical deep red appearance. The mid-section is used to measure left ventricular wall thickness and chamber diameter. The infarct size is determined by planimetry of the scarred portion of the ventricle and expressed as a percent of scar/viable myocardium yielding the extent of fibrosis. Histology and immunochemistry is performed as described above.

Apoptosis

Apoptosis is observed using TUNEL staining in situ (apoptosis detection kit from CardiacTACS, Trevigen, Inc). The kit is based on DNA end labeling using terminal deoxynucleotidyl transferase (TdT) with a modified nucleotide that is subsequently detected via a colorimetric detection system. Sections are examined using transmitted light microscopy and digital images captured for quantification. Approximately 1000 nuclei are counted per section (n=4 sections for each heart) by using a 10×10 micron eyepiece grid positioned at 20 areas around the LV. The percentage of TUNEL positive nuclei are counted in the border region of the infarct and the viable myocardium. To determine the hypoxic region in the absence of an overt scar (2 weeks post-MI), pimonidazole hydrochloride are used as a marker of hypoxia (Hypoxyprobe TM-1 Kit, Chemicon International). Animals will be injected with pimonidazole hydrochloride (60 mg/kg body weight), 90 minutes before sacrifice. Sections from these hearts are incubated with hypoxyprobe1-Mab1 for 40 minutes at room temperature (working dilutions 1:50) and with goat anti-mouse IgG antibody FITC for 60 minutes (Sigma). Based on the hypoxia marker, pimonidazole hydrochloride, areas are designated as ischemic and periischemic for the MI group as previously published (Zampino, 2006).

Western Blotting and Quantitative RT-PCR

A number of different acrylamide/bisacrylamide ratios are used to optimally separate various proteins. Proteins are transferred to nitrocellulose and probed with specific antibodies using standard western blotting techniques. Membranes are incubated in Blocking Buffer consisting of 5% nonfat dry milk in TBS (20 mM Tris-HCl, pH 7.6, 137 mM NaCl) for 1 h. Affinity-purified antibodies against phospho-Akt (Ser473/308), phospho-Bad (Ser136), activated Caspase-3 C (18 kD cleavage fragment), total Akt, FOXO3α, Bad (Cell Signaling), incubated overnight at +4° C. After washing the membranes in TBS-T, secondary antibody (goat anti-rabbit diluted 1:10,000 in blocking buffer) is added for 1 h at room temperature. Immunoreactive bands are visualized by enhanced chemiluminescence using a Chemidoc XRS, (Bio-Rad) fitted with a cooled CCD camera, which allows integration of the signal over real time. The percentage of the protein phosphorylation is determined by signal analysis over the linear range of acquisition and expressed as phospho-protein/total protein+phospho-protein)×100%. Gene expression is assessed by real-time quantitative RT-PCR. Total RNA is extracted using Trizol and a 100 ng of total RNA is used in each RT-PCR reaction (Goldspink, 2004).

Statistics and Sample Size Estimates

Based upon preliminary studies, we expect changes in the mean hemodynamic measurements (e.g. +/−dp/dt) to be approximately 25% in experimental groups (sham vs. expt group for each treatment) with a standard deviation of 10-12%. These differences are detected with a sample of 6 animals in each group. With this sample size, the power of test for the two-sided hypothesis is 0.8, when alpha is set at 0.05. However, a greater number of animals are required for the post functional analysis (biochemical, cell isolations). Data are expressed as mean±standard error (SEM). Differences are tested for statistical significance (P<0.05) using student's t-test, paired or unpaired, two-way analysis of variance (ANOVA), followed by post-hoc analysis to test for significance within the groups where appropriate.

The aforementioned methods have been employed as follows.

Time Course of Expression of Isoforms of IGF-1 Family in Mouse Heart

Figure 11:
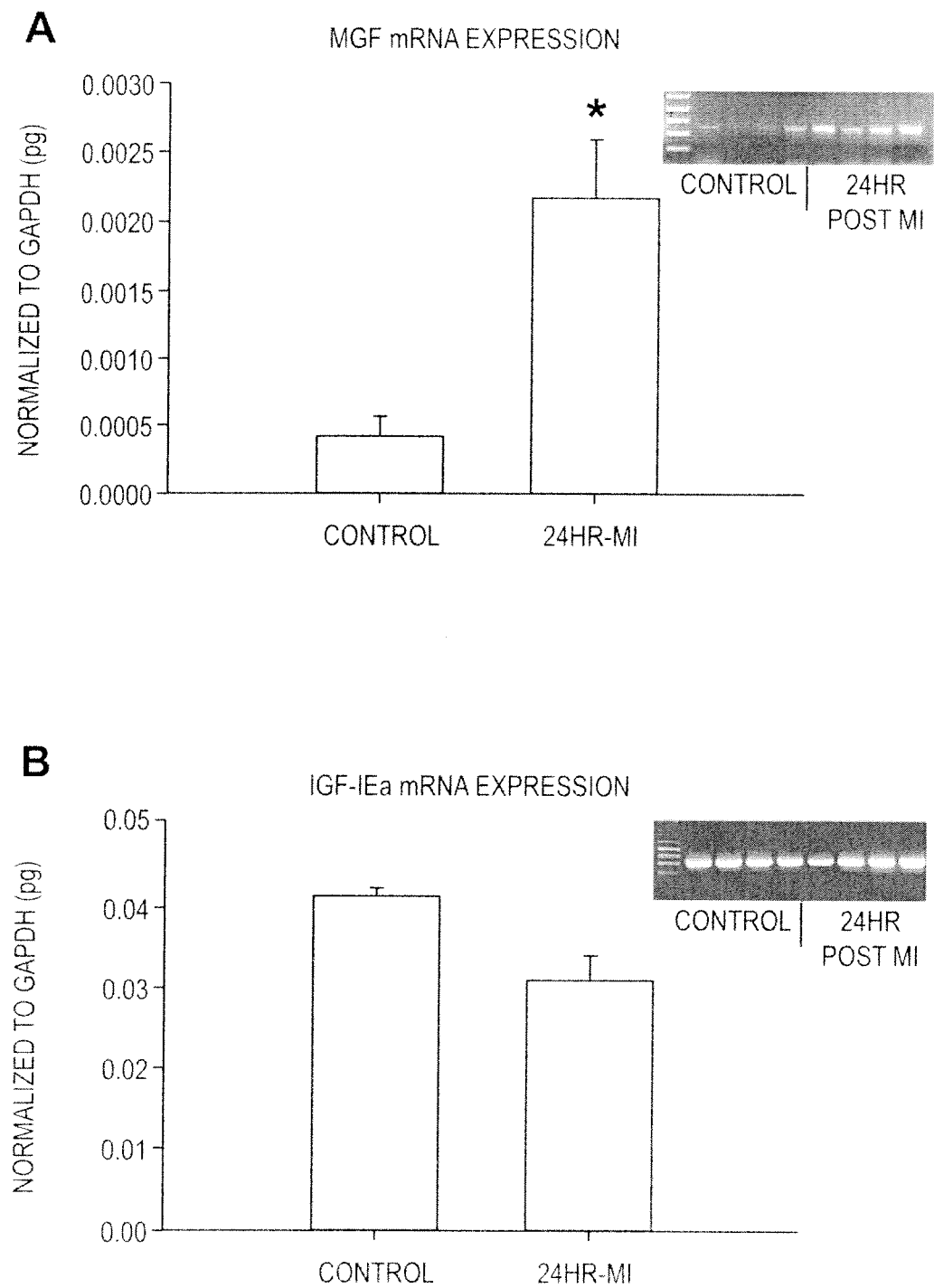
FIG. 11. shows quantification of MGF and IGF-1 isoform expression in the mouse heart following myocardial infarct using real time RT-PCR.

Increased expression of the IGF-1Eb (MGF) occurred within 24 hours following myocardial infarct at a time when the predominant IGF-1Ea isoform did not change (FIG. 11). Therefore, providing more E-domain, the actions of IGF-1 produced by the heart were enhanced following stress or a myocardial infarct (MI).

Expansion of the Cardiac Side Population with MGF E-domain Treatment.

To evaluate the potential benefits of the MGF E-domain peptide, the stabilized peptide was delivered systemically (2 weeks) via mini-osmotic pumps implanted prior (12 hrs) to coronary artery ligation in mice. Whether the E-domain peptide is sufficient to either expand the resident population of stem cells or act as a mobilization/homing factor attracting stem cells to the heart was determined. A side population of stem cells in the heart was identified defined by efflux of Hoechst and sensitivity to verapamil treatment (Asakura, 2002). Based upon reports in the literature, these cells usually constitute 0.03-0.06% of the total digest (Oh 2003). However, the side population was increased ~ten-fold in hearts of mice treated with the MGF E-domain peptide for 48 hrs. Analysis of the Sca1+ cells within the side population revealed a similar ten-fold increase indicating there is expansion of the stem cell pool within the hearts of mice treated with MGF E-domain peptide.

Expansion of Cardiac Stem Cell with MGF E-domain Peptide Treatment to Infarcted Mouse Heart.

Figure 12:
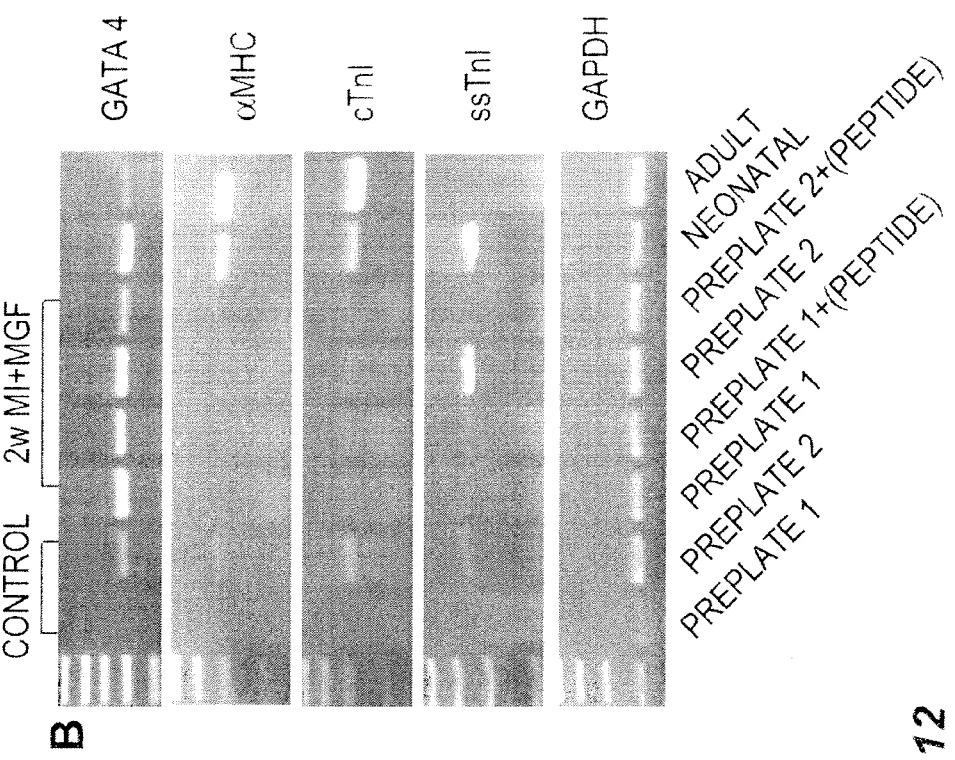
FIG. 12. shows expansion of stem cells in mouse heart with MGF treatment after myocardial infarction.
Figure 12:
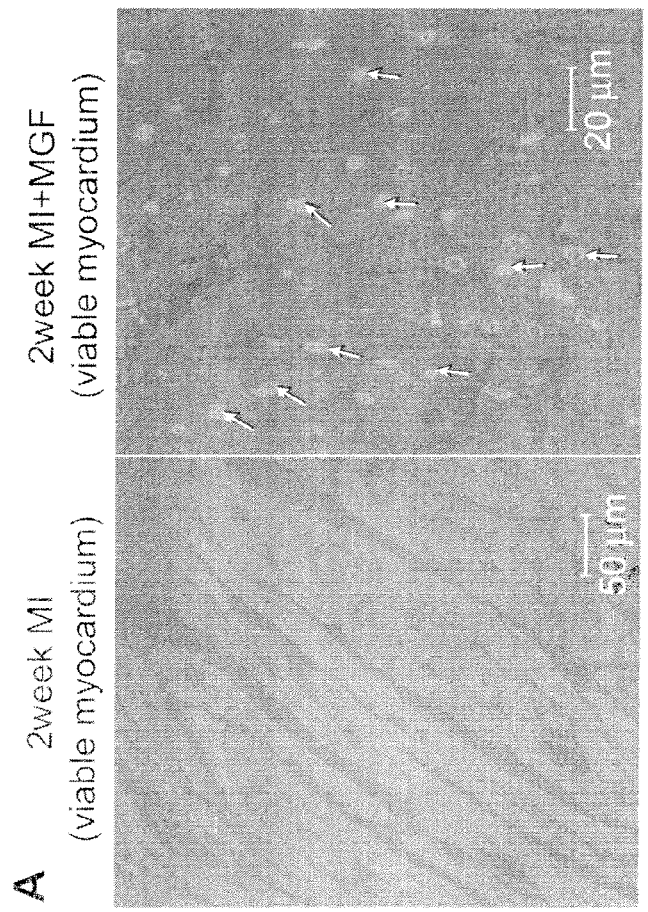

Evaluation using immuno-histochemical analysis of the mouse hearts treated with the E-domain peptide post-infarct reveals a large number of small troponin I staining positive cells in the septum and viable ventricular tissue but not in the infarct region (FIG. 12A). Conversely, these cells were not detected in sham-operated or infarcted hearts. Further characterization of these cells shows that the expression of the muscle lineage protein (TnI) is also co-expressed with the cardiac specific transcription factor (NRx2.5) and a cardiac progenitor cell marker (Isl-1) in the nuclei (data not shown). In order to isolate, characterize and enrich these cells, hearts were digested with collagenase and the resultant cells subjected to a series of pre-plating steps. Gene expression analysis confirmed that the second pre-plating step is enriched for cells expressing the slow skeletal troponin (ssTnI), which is normally expressed during embryonic development and the cardiac transcription factor GATA 4. The adult isoforms of myosin heavy chain (alphaMHC) and cardiac TnI (cTnI) were not expressed in cells present in the second pre-plating step indicating a lack of contamination with differentiated cardiac myocytes (FIG. 12B).

Functional Improvement with Delivery of Stable MGF E-domain Peptide Post-infarct.

Figure 13:
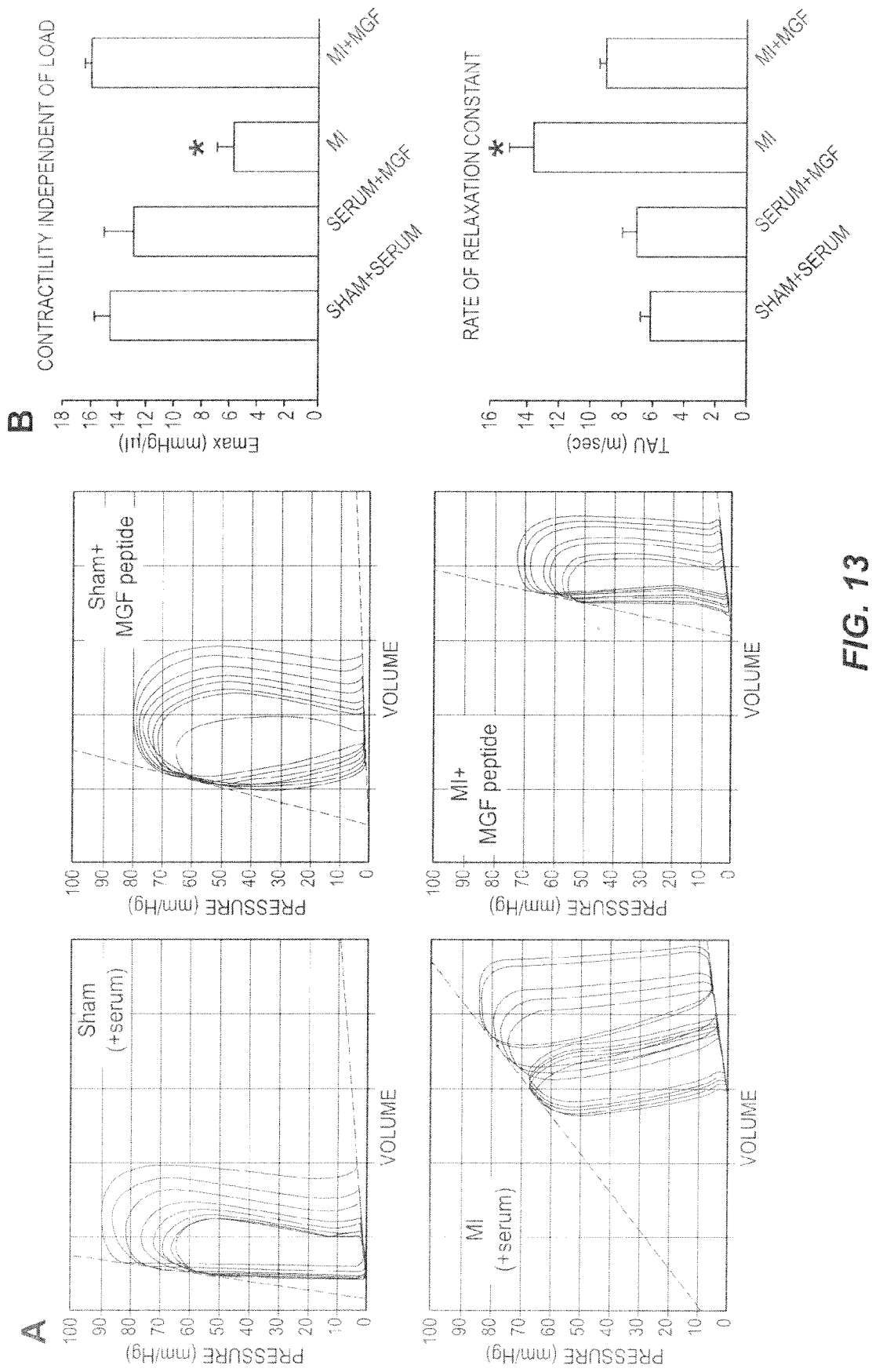
FIG. 13. shows pressure-volume loops from instrumented mice 2 weeks post myocardial infarction with and without systemic delivery of MGF E-domain peptide.

Four groups of mice are used: Sham, MI, Sham+MGF (E-domain peptide, 1 mg/Kg/day), and MI+MGF (FIG. 13A). At 2 weeks post-infarct, cardiac function was evaluated by pressure-volume analysis in situ, along with assessment of cardiac mass index and changes in gene expression. Analysis of cardiac function showed no significant differences in the hemodynamic parameters between the Sham and Sham+MGF groups. However, there was a 63% decrease in Emax and a 32% decrease in dP/dtmax with MI, which was ameliorated in the MI+MGF group. Other hemodynamic parameters (LVSP, both +/−dP/dt, Tau) were also preserved in the MI+MGF group, and were significantly different in the MI group (FIG. 13B). Analyses of gene expression in these hearts showed significant increases in both ANF and β-MHC mRNA expression was associated with an increased heart to body weight ratio in the MI group, indicative of hypertrophy. Conversely, there was no increase in the heart weight to body weight ratio in the MI+MGF group, which was associated with the inhibition of the hypertrophy/fetal gene program. These data demonstrated that there was improved contractile function with 2 wk systemic application of the stabilized E-domain peptide in infarcted mice. The improvement at 2 weeks was associated with decreased expression of the pathophysiological gene program and prevention of hypertrophic remodeling of the heart.

Effect of Stable MGF E-domain Peptide on Apoptosis in Mouse Heart Post-infarct

Figure 14:
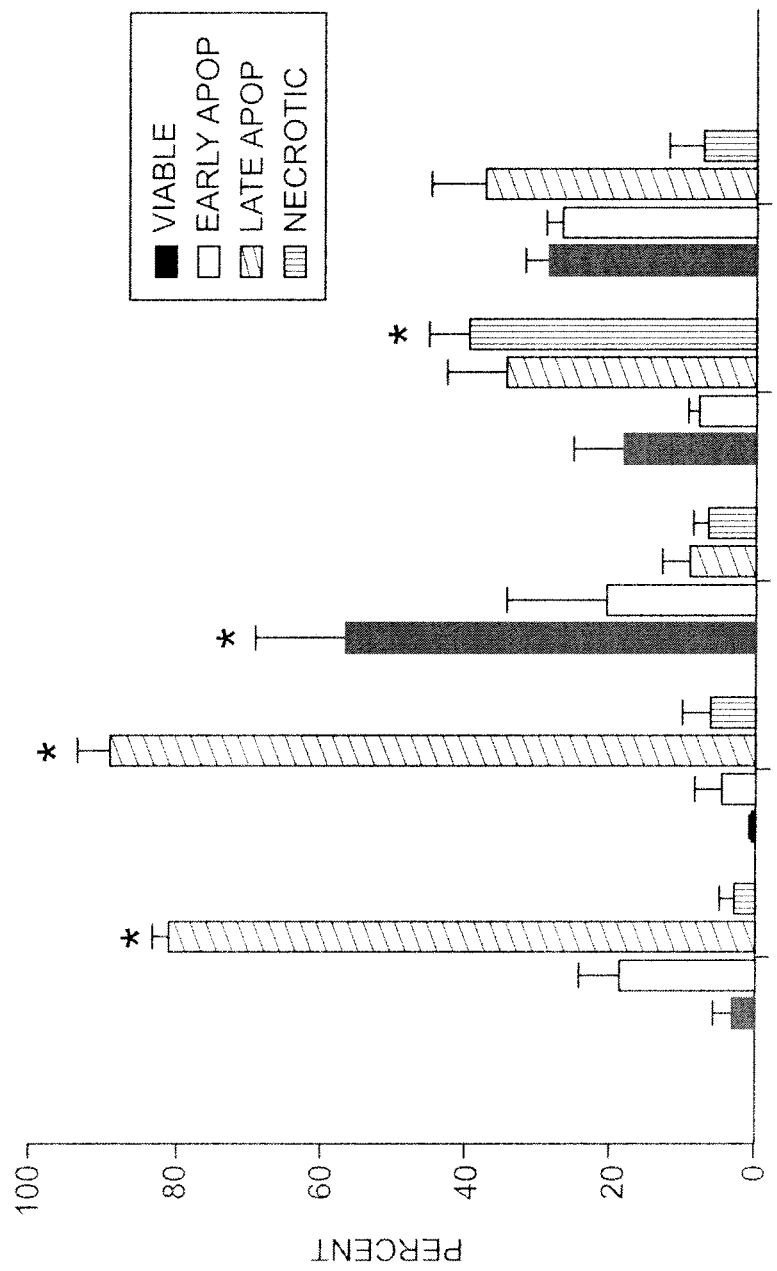
FIG. 14. shows apoptosis analysis of mouse cardiac myocytes post-infarct.

To determine whether an inhibition of apoptosis may contribute to the functional improvement seen in the mouse heart post-MI with MGF E-domain peptide treatment, adult cardiac myocytes were isolated by collagenase digestion and stained with propidium iodide (PI) and annexin V (AV). The extent of apoptosis was examined using flow cytometry (FACS). Staining revealed a greater percent of necrotic and apoptotic myocytes isolated from the untreated 2 wk MI group compared to the 2 wk MI+MGF treated group, which showed a greater number of viable myocytes (FIG. 14). These data showed that systemic administration of the stable MGF E-domain peptide during the acute phase of a myocardial infarct protected the myocardium by preventing apoptosis, which in turn, may contribute to preserving contractile function and prevent pathologic remodeling of the heart.

Injection of Microrods into the Mouse Heart

Figure 15:
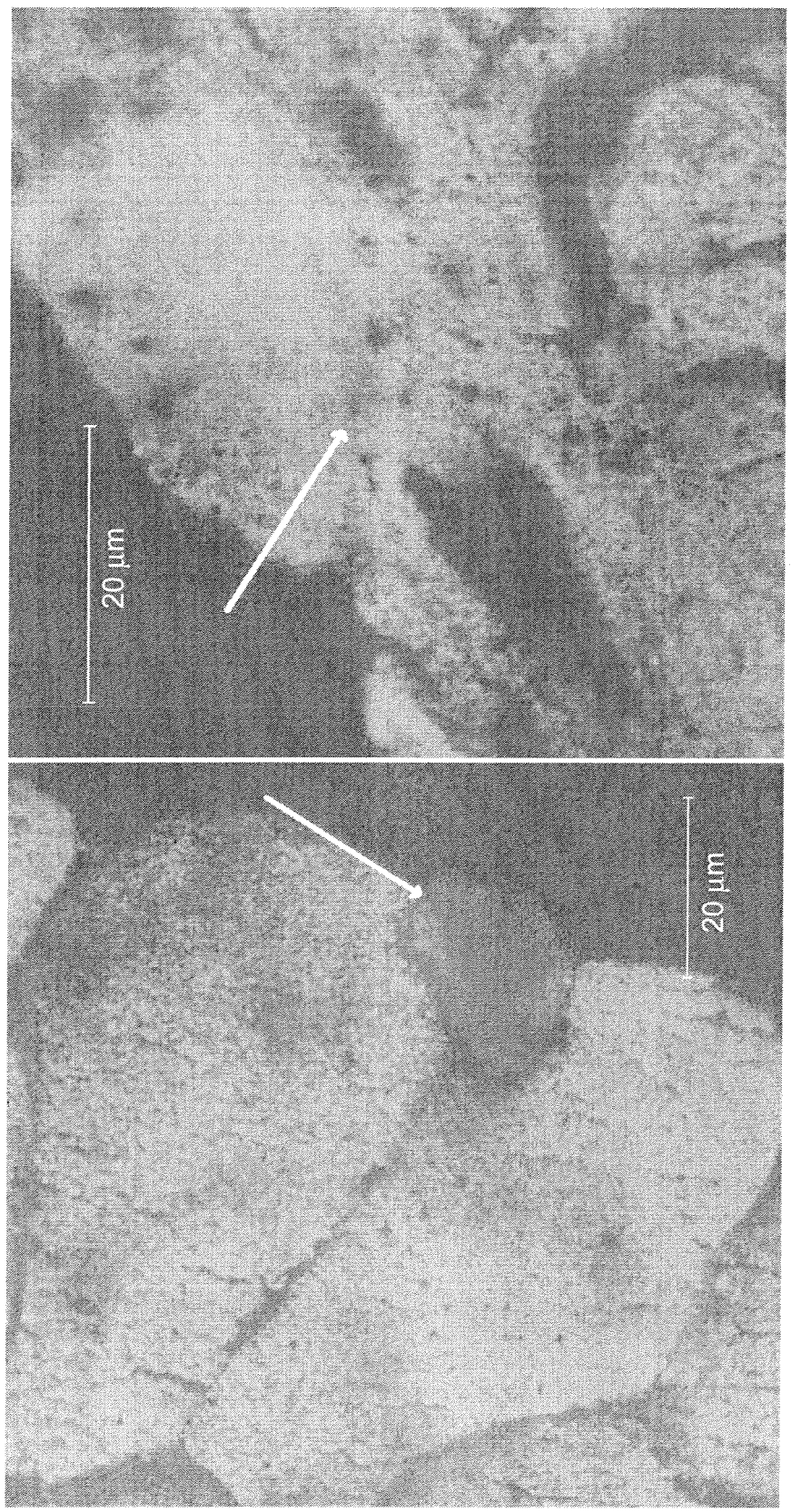
FIG. 15. shows fluorescent images of SU-8 microrods injected into mouse tibialis anterior (left) and myocardium (right) for 2-days.

10 μl of 1000 SU-8 microrods/μl were injected directly in the ventricle and skeletal muscle. The tissue was fixed sectioned and examined for the presence of the SU-8 microrods after 48 hours. Blue fluorescing SU-8 could be detected indicating that the delivery of the MRS is achieved (FIG. 15).

Example 7

Cardiac Function Improves in Infracted Mouse Heart Two Weeks after MGF-MRS Elution Therapy Approximately 3,000 PEGDA MGF E-domain-eluting microrods were injected into the infarct region of mouse hearts 10 minutes post-infarct in one conhort of mice and compared to mice that did not receive either an infarct (control) or infracted mice without treatment (2 weeks post myocardial infarction). Cardiac function and hypertrophy were measured 2 weeks following treatment. Stroke volume, ejection fraction, cardiac output and cardiac mass index were all statistically better in mice treated with MGF-MRS therapy (FIG. 19A-D). Cardiac function was improved and hypertrophy was prevented with MGF-MRS therapy (FIG. 19C and FIG. 19D, respectively).

MGF-MRS elution therapy also promotes and supports cardiac regeneration. 50% PEGDA MRS loaded with MGF E-domain peptide were injected into the hearts of control mice at three sites in the apex. Controls were empty PEGDA MRS. The mice were sacrificed four weeks following injections and sections were cut for histological analysis. FIGS. 20A and 20B show sections of cardiac tissue injected with empty PEGDA MRS and E-domain loaded PEGDA MRS stained with H&E. Immunohistochemical analysis with anti-Ki67 (cell cycling) and slow skeletal troponin I (ssTnI; marker for resident cardiac progenitor cells and fetal myocytes) suggest that proliferating and newly formed myocytes can be detected in the vicinity of the E-domain loaded PEGDA MRS, but not in the vicinity of the empty MRS in vivo (FIGS. 20C and 20D). This indicates that the delivery of the MGF E-domain peptide via the MRS-eluting system may provide a means to direct and support stem cell therapy in the heart and other tissues following injury.

Example 8

Characterization of Resident Cardiac Progenitor Cells Isolated from the Hearts of MGF E-domain MRS Treated Mice Resident cardiac progenitor (RP) cells were isolated from the hearts of E-domain MRS treated mice. At about day 7 post-treatment, the RP cells start to form colonies (FIG. 21A). Staining of fixed cells with an antibody that recognizes the slow skeletal isoform of troponin I (ssTnI) demonstrates protein expression in RP cells, similar to the RP cells in vivo (FIG. 21C). Furthermore, gene expression analysis of RNA extracted from colonies at day 10 shows expression of several cardiac transcription factors, ssTnI and SERCA2 transcripts (FIG. 21D). These data are consistent with gene and protein expression data derived from this population in vivo (data not shown). Thus, these data demonstrate we can isolate and maintain in culture RP cells that are responsive to MGF E-domain MRS treatment.

To demonstrate whether this population of RP cells would commit and differentiate into cardiac myocytes, RP cells were treated with 50 ng/ml Wnt 5a (an activator of the non-canonical Wnt pathway) and Dkk1 (Dickkopf-1) for various times (FIG. 22). After 2 weeks of treatment, cells start to form connected branches which beat spontaneously at 3 weeks (FIGS. 22A-C). Labeling with Fluo-4 AM revealed spontaneous calcium oscillations in beating clusters (video images not included). Gene expression analysis of RNA extracted from a single colony after 3 weeks of treatment, shows increased expression of genes associated with calcium handling (L-type calcium channel (Cav1.2), phospholamban (PLB); FIG. 22D). In addition, there was increased expression of the fetal contractile protein isoforms of troponin T (cTnT2) and myosin heavy chain (βMHC) (FIG. 22D). Interestingly, the Ryanodine receptor did not appear to be expressed at this time point, which may explain a lack of synchronous beating in these cells. These data demonstrate that the RP cells derived from hearts of MGF E-domain MRS treated mice are capable of committing to the cardiac linage. They also support with a high degree of probability the ability to target and instruct RP cells in vivo, with the delivery of the MGF E-domain peptide via the MRS to aid in cardiac regeneration.

References

Alberts, B., Bray, D., Lewis, J., Raff, M., Roberts, K., and James, D. Watson. Cell junctions, cell adhesions, and the extracellular matrix. In: Molecular Biology of the Cell. New York: Garland Publishing, 1994, pp. 950-1006.

Angst B D, Khan L U, Severs N J, Whitely K, Rothery S, Thompson R P, Magee A I and Gourdie R G. Dissociated spatial patterning of gap junctions and cell adhesion junctions during postnatal differentiation of ventricular myocardium. Circ Res 1997; 80:88-94.

Asakura A, Rudnicki M A. Side population cells from diverse adult tissues are capable of in vitro hematopoietic differentiation. Exp Hematol. 2002 November; 30(11):1339-45.

Biehl, J. K., Yamanaka, S., Desai, T., Boheler, K. R. and Russell, B. Proliferation of mouse embryonic stem cell progeny and the spontaneous contractile activity of cardiomyocytes are affected by microtopography. *Dev. Dyn.* 2009; 238: 1964-1973.

Bloch R J, Gonzalez-Serratos H, Lateral force transmission across costameres in skeletal muscle. Exerc Sport Sci Rev. 2003 April; 31(2):73-8.

Boateng S Y, Hartman T J, Ahluwalia N, Vidula H, Desai T A, Russell Inhibition of fibroblast proliferation in cardiac myocyte cultures by surface microtopography. Am J Physiol Cell Physiol. 2003 July; 285(1):C171-82.

Boheler K R, J Czyz, D Tweedie, H T Yang, S V Anisimov and A M Wobus. Differentiation of pluripotent embryonic stem cells into cardiomyocytes. Circ Res., 91:189 B201, 2002.

Boheler K R. ES cell differentiation to the Cardiac Lineage. In Methods in Enzymology. Editors: P. M. Wassarman and G. M. Keller, Volume 365, Chapter 16, pp. 228-241, 2003.

Boron, W. F., and Boulpaep, E. L. Hepatobiliary function. In: Medical Physiology. Philadelphia, Pa.: W. B. Saunders, 2003, pp. 975-1002.

Buerke M, Murohara T, Skurk C, Nuss C, Tomaselli K, Lefer A. Cardioprotective Effect of Insulin-Like Growth Factor I in Myocardial Ischemia Followed by Reperfusion. Proceedings of the National Academy of Sciences USA 1995; 92:8031-8035.

Caspi O, Gepstein L. Potential applications of human embryonic stem cell-derived cardiomyocytes. Ann N Y Acad Sci. 2004 May; 1015:285-98.

Chicurel, M. E., Chen, C. S, and Ingber, D. E. (1998). "Cellular control lies in the balance of forces." Curr Opin Cell Biol 10(2): 232-9.

Cheng W, Kajstura J, Nitahara J, Li B, Reiss K, Liu Y, Clark W, Krajewski S, Reed J, Olivetti G, Anversa P. Programmed Myocyte Cell Death Affects the Viable Myocardium after Infarction in Rats. Experimental Cell Research. 1996; 226: 316-327.

Chicurel M E, Singer R H, Meyer C J, Ingber D E, Integrin binding and mechanical tension induce movement of mRNA and ribosomes to focal adhesions. Nature. 1998 Apr. 16; 392(6677):730-3.

Collins, J. M., Ayala, P., Desai, T. and Russell, B. Three-dimensional culture with stiff microstructures increases proliferation and slows osteogenic differentiation of human mesenchymal stem cells. *Small*, 2009 (E-pub ahead of print; PMID: 19943257).

Cooper G t, Mercer W E, Hoober J K, et al. Load regulation of the properties of adult feline cardiocytes. The role of substrate adhesion. Circ Res. 1986; 58:692-705.

Cohen, S., Yoshioka, T., Lucarelli, M., Hwang, L. H. & Langer, R. Controlled delivery systems for proteins based on poly(lactic/glycolic acid) microspheres. Pharmacol. Res. 8, 713â?"720 (1991).

Crotts G. and T G Park, Protein delivery from poly(lactic-co-glycolic acid) biodegradable microspheres: release kinetics and stability issues, J. Microencapsul. 15: 1998, pp. 699-713.

Davis M E, Hsieh P C, Takahashi T, Song Q, Zhang S, Kamm R D, Grodzinsky A J, Anversa P, Lee R T. Local myocardial insulin-like growth factor 1 (IGF-1) delivery with biotinylated peptide nanofibers improves cell therapy for myocardial infarction. Proc Natl Acad Sci. 2006 May 23; 103(21):8155-60.

Deutsch-Snyder, J and T A Desai. Fabrication of Multiple Microscale Features on Polymer Surfaces for Applications in Tissue Engineering. Journal of Biomaterials Science, Polymer Edition, 3:293-300, 2001.

Duerr R L, McKirnan M D, Gim R D, Clark R G, Chien K R, Ross J. Jr. Cardiovascular effects of insulin-like growth factor-1 and growth hormone in chronic left ventricular failure in the rat. Circulation. 1996 Jun. 15; 93(12):2188-96.

Dluzniewska J, Sarnowska A, Beresewicz M, Johnsomn I, Srai S K, Ramesh B, Goldspink G, Gorecki D C, Zablocka B. A strong neuroprotective effect of the autonomous C-terminal peptide of IGF-1 Ec (MGF) in brain ischemia. FASEB J. 2005 November; 19(13):1896-8.

Edelman, E. R., Mathiowitz, E., Langer, R. & Klagsbrun, M. Controlled and modulated release of basic fibroblast growth factor. Biomaterials. 12, 619-626, (1991).

Ennett A B, Kaigler D, Mooney D J. Temporally regulated delivery of VEGF in vitro and in vivo. J Biomed Mater Res A. 2006 October; 79(1):176-84.

Engler A J, Griffin M A, Sen S, Bonnemann C G, Sweeney H L, Discher D E. Myotubes differentiate optimally on substrates with tissue-like stiffness: pathological implications for soft or stiff microenvironments. J Cell Biol. 2004 Sep. 13; 166(6):877-87.

Engler A J, Sen S, Sweeney H L, Discher D E. Matrix elasticity directs stem cell lineage specification. Cell. 2006 Aug. 25; 126(4):677-89.

Fawcett, D. W. Blood lymph vascular systems. In: Textbook of Histology. Philadelphia, Pa.: W. B. Saunders, 1986, pp. 367-400.

Fazio S, Sabatini D, Capaldo B, Vigorito C, Giordano A, Guida R, Pardo F, Biondi B, Sacca L. A preliminary study of growth hormone in the treatment of dilated cardiomyopathy. N Engl J Med. 1996 Mar. 28; 334(13):809-14.

Fazal F, Gu L, Ihnatovych I, Han Y, Hu W, Antic N, Carreira F, Blomquist J F, Hope T J, Ucker D S, de Lanerolle P, Inhibiting myosin light chain kinase induces apoptosis in vitro and in vivo. Mol Cell Biol. 2005 July; 25(14):6259-66.

Fazel S, Cimini M, Chen L, Li S, Angoulvant D, Fedak P, Verma S, Weisel R D, Keating A, and Li R K. Cardioprotective c-kit+cells are from the bone marrow and regulate the myocardial balance of angiogenic cytokines. J Clin Invest. 2006 July 3; 116(7): 1865-1877.

Fishman G I, Hertzberg E L, Spray D C and Leinwand L A. Expression of connexin43 in the developing rat heart. Circ Res. 1991; 68:782-7

Foyt H T, LeRoith D, Roberts C T. Differential association of insulin-like growth factor I mRNA variants with polysomes in vivo. J Biol Chem. 1991 Apr. 15; 266(11):7300-5.

Fu J D, Li J, Tweedie D, Yu H M, Chen L, Wang R, Riordon D R, Brugh S A, Wang S Q, Boheler K R, Yang H T. Crucial role of the sarcoplasmic reticulum in the developmental regulation of Ca2+ transients and contraction in cardiomyocytes derived from embryonic stem cells. FASEB J. 2006 January; 20(1):181-3.

Goldspink P H, Montgomery D E, Walker L A, Urboniene D, McKinney R D, Geenen D L, Solaro R J Buttrick P M. Protein kinase Ce over-expression alters myofilament properties and composition during the progression of heart failure. Circ Res. 95(4): 424-32. 2004.

Goldspink G. Impairment of IGF-I gene splicing and MGF expression associated with muscle wasting. Int J Biochem Cell Biol. 37:2012-22 (2005).

Gray D S, Tien J, Chen C S, Repositioning of cells by mechanotaxis on surfaces with micropatterned Young's modulus. J Biomed Mater Res A. 2003 Sep. 1; 66(3):605-14.

Grossman W, Jones D, McLaurin L P. Wall stress and patterns of hypertrophy in the human left ventricle. J Clin Invest. 1975; 56:56-64.

Holmes J W, Borg T K, Covell J W. Structure and mechanics of healing myocardial infarcts. Annu Rev Biomed Eng. 2005; 7:223-53.

Huang R, Jiang Y and Liang H. Effect of architecture on the tensile properties of triblock copolymers in a lamellar phase. Chemphyschem. 2006 Sep. 11; 7(9):1950-6.

Huang S and Ingber D E, The structural and mechanical complexity of cell-growth control. Nat Cell Biol. 1999 September; 1(5):E131-8.

Ingber D E. Cellular mechanotransduction: putting all the pieces together again. FASEB J. 2006; 20:811-827.

Ingber D E. Mechanobiology and diseases of mechanotransduction. Ann Med. 2003a; 35:564-577.

Ingber D E. Tensegrity I. Cell structure and hierarchical systems biology. J Cell Sci. 2003b; 116:1157-1173.

Ingber D E, Madri J A, Jamieson J D, Neoplastic disorganization of pancreatic epithelial cell-cell relations. Role of basement membrane. Am J. Pathol. 1985 November; 121(2): 248-60.

Ingber D E, Mechanical control of tissue morphogenesis during embryological development. Int J Dev Biol. 2006; 50(2-3):255-66.

Jain R A. The manufacturing techniques of various drug loaded biodegradable poly(lactide-co-glycolide) (PLGA) devices. Biomaterials. 21 (2000) 2475-90.

Kajstura J, Cheng W, Reiss K, Clark W A, Sonnenblick E H, Krajewski S, Reed J C, Olivetti G, Anversa P. Apoptotic and necrotic myocyte cell deaths are independent contributing variables of infarct size in rats. Lab Invest. 1996 January; 74(1):86-107.

Kelly R G, Buckingham M E. The anterior heart-forming field: voyage to the arterial pole of the heart. Trends Genet. 2002 April; 18(4):210-6.

Kim, Kwangsok, K Yu, X Zong, J Chiu, D Fang, Y-S Seo, B S Hsiao, B Chu and M Hadjiargyrou. Control of degradation rate and hydrophilicity in electrospun non-woven poly (D,L-lactide) nanofiber scaffolds for biomedical applications. Biomaterials. Accepted May 30, 2003.

Krieg M, Arboleda-Estudillo Y, Puech P H, Käfer J, Graner F, Muller D J, Heisenberg C P, Tensile forces govern germ-layer organization in zebrafish. Nat Cell Biol. 2008 April; 10(4):429-36. Epub 2008 Mar. 23.

Kumar A, Chaudhry I, Reid M B, Boriek A M, Distinct signaling pathways are activated in response to mechanical stress applied axially and transversely to skeletal muscle fibers. J Biol Chem. 2002 Nov. 29; 277(48):46493-503.

Kumar D, Hacker T A, Buck J, Whitesell L F, Kaji E H, Douglas P S, Kamp T J. Distinct mouse coronary anatomy and myocardial infarction consequent to ligation. Coron Artery Dis. 2005 February; 16(1):41-4.

Kurpinski K, Chu J, Hashi C, Li S. Anisotropic mechanosensing by mesenchymal stem cells. Proc Natl Acad Sci USA. 2006 Oct. 31; 103(44):16095-100.

Langer, R. Drug delivery and targeting. Nature. 1998 Apr. 30; 392 (6679 Suppl):5-10. Review. Langer R, Vacanti J P. Tissue engineering. Science. 1993 May 14; 260(5110):920-6. Review.

Lanza R P and R W L Langer. Chick Principles of Tissue Engineering, 2000.

Lee K Y, Peters, M. C., Anderson, K. W. & Mooney, D. J. Controlled growth factor release from synthetic extracellular matrices. Nature. 408, 998-1000 (2000).

Lele T P, Thodeti C K, Ingber D E. Force meets chemistry: analysis of mechanochemical conversion in focal adhesions using fluorescence recovery after photobleaching. J Cell Biochem. 2006; 97:1175-1183.

Lele T P, Pendse J, Kumar S, Salanga M, Karavitis J, Ingber D E, Mechanical forces alter zyxin unbinding kinetics within focal adhesions of living cells. J Cell Physiol. 2006 April; 207(1):187-94.

Lemaire V., J. Bélair and P. Hildgen, Structural modeling of drug release from biodegradable porous matrices based on a combined diffusion/erosion process. Int. J. Pharm. 258 (2003), pp. 95-107.

Li Q, Li B, Wang X, Leri A, Jana K, Liu Y, Kajstura J, Baserga R, Anversa P. Overexpression of Insulin-Like Growth Factor I in Mice Protects from Myocyte Death after Infarction, Attenuating Ventricular Dilation, Wall Stress, and Cardiac Hypertrophy. Journal of Clinical Investigation 1997; 100:1991-1999.

Lo C M, Wang H B, Dembo M, Wang Y L, Cell movement is guided by the rigidity of the substrate. Biophys J. 2000 July; 79(1):144-52.

Lo C M., Wang, H. B., Dembo, M. and Wang, Y. L. (2000). "Cell movement is guided by the rigidity of the substrate." Biophys J. 79(1): 144-52.

Mahoney, M. & Saltzman, W. Millimeter-scale positioning of a nerve-growth-factor source and biological activity in the brain. Proc. Natl. Acad. Sci. 96, 4536-4539 (1999).

Mansour, H., P. P. de Tombe, A. M. Samarel and B. Russell (2004). Restoration of resting sarcomere length after uniaxial static strain is regulated by protein kinase Cepsilon and focal adhesion kinase. Circ Res. 94(5): 642-9.

Matthews K G, Devlin G P, Conaglen J V, Stuart S P, Mervyn Aitken W, Bass J J. Changes in IGFs in cardiac tissue following myocardial infarction. J Endocrinol. 1999 December; 163(3):433-45.

McKoy G, Ashley W, Mander J, Yang S Y, Williams N, Russell B, Goldspink G. Expression of insulin growth factor-1 splice variants and structural genes in rabbit skeletal muscle induced by stretch and stimulation. J. Physiol. 1999 Apr. 15; 516 (Pt 2):583-92.

Motlagh, D, S E Senyo, T A Desai and B Russell. Microtextured substrata alter gene expression, protein localization and the shape of cardiac myocytes. Biomaterials. 24: 2436-2476, 2003a.

Motlagh D, Hartman T J, Desai T A, Russell B. Microfabricated grooves recapitulate neonatal myocyte connexin43 and N-cadherin expression and localization. J Biomed Mater Res. 67A:148-57, 2003b.

Muta K, Krantz S. Apoptosis of Human Erythroid Colony-Forming Cells is Decreased by Stem Cell Factor and Insulin-Like Growth Factor I as Well as Erythropoietin. Journal of Cellular Physiology. 1993;156: 264-271.

Nahta R, Yuan L X, Zhang B, Kobayahi R, Esteva F J. Insulin-like growth factor-I receptor/human epidermal growth factor receptor 2 heterodimerization contributes to trastuzumab resistance of breast cancer cells. Cancer Res. 2005 Dec. 1; 65(23):11118-28.

Oh H, Bradfute S B, Gallardo T D, Nakamura T, Gaussin V, Mishina Y, Pocius J, Michael L H, Behringer R R, Garry D J, Entman M L, Schneider M D. Cardiac progenitor cells from adult myocardium: homing, differentiation, and fusion after infarction. Proc Natl Acad Sci USA. 2003 Oct. 14; 100(21): 12313-8.

Olson E N, Schneider M D Sizing up the heart: development redux in disease. Genes Dev. 2003 Aug. 15; 17(16): 1937-56.

Reinecke, H, M Zhang, T Bartosek and C E Murry. Survival, integration, and differentiation of cardiomyocyte grafts: A study in normal and injured rat hearts. Circulation. 100:193 B202, 1999.

Pelham R J Jr, Wang Y, Cell locomotion and focal adhesions are regulated by substrate flexibility. Proc Natl Acad Sci USA. 1997 Dec. 9; 94(25):13661-5.

Pfister O, Mouquet F, Jain M, Summer R, Helmes M, Fine A, Colucci W S, Liao R. CD31− but Not CD31+cardiac side population cells exhibit functional cardiomyogenic differentiation. Circ Res. 2005 Jul. 8; 97(1):52-61.

Reiss K, Kajstura J, Zhang X, Li P, Szoke E, Olivetti G, Anversa P. Acute myocardial infarction leads to upregulation of the IGF-1 autocrine system, DNA replication, and nuclear mitotic division in the remaining viable cardiac myocytes. Exp Cell Res. 1994 August; 213(2):463-72.

Reiss K., W Cheng, A Ferber, J Kajstura, P Li, B Li, G Olivetti, C J Homcy, R Baserga, and P Anversa. Overexpression of insulin-like growth factor-1 in the heart is coupled with myocyte proliferation in transgenic mice. Proc Natl Acad Sci USA. 1996 Aug. 6; 93(16):8630-5.

Richardson T P, M C Peters, A B Ennett & D J Mooney. Polymeric system for dual growth factor delivery. Nature Biotechnology. 19, 1029-1034 (2001)

Rodriguez-Tarduchy G, Collins M, Garcia I, Lopez-Rivas A. Insulin-Like Growth Factor I Inhibits Apoptosis in IL-3-Dependent Hemopoietic Cells. Journal of Immunology 1992; 149:535-540.

Russell S M, Spencer E M. Local injections of human or rat growth hormone or of purified human somatomedin-C stimulates unilateral tibial epiphyseal growth in hypophysectomized rats. Endocrinology. 1985 June; 116(6):2563-7.

Samarel A M. Costameres, focal adhesions, and cardiomyocyte mechanotransduction. Am J Physiol Heart Circ Physiol. 2005 December; 289(6):H2291-301.

Sahn, D. J., DeMaria, A., Kisslo, J., Weyman, A. Recommendations regarding quantitation in M-mode echocardiography: results of a survey of echocardiographic measurements. Circulation. 58: 1072-83. 1978.

Samarel A M, Costameres, focal adhesions, and cardiomyocyte mechanotransduction. Am J Physiol Heart Circ Physiol. 2005 December; 289(6):H2291-301.

Sauer H, Theben T, Hescheler J, Lindner M, Brandt M C, Wartenberg M. Characteristics of calcium sparks in cardiomyocytes derived from embryonic stem cells. Am J Physiol Heart Circ Physiol. 2001 July; 281(1):H411-21.

Schiaffino S, Reggiani C. Molecular diversity of myofibrillar proteins: gene regulation and functional significance. Physiol Rev. 1996 April; 76(2):371-423.

Semler E J, Ranucci C S, and Moghe P V. Mechanochemical manipulation of hepatocyte aggregation can selectively induce or repress liverspecific function. Biotechnol Bioeng 69: 359-369, 2000.

Senyo S E, Koshman Y E, Russell B, Stimulus interval, rate and direction differentially regulate phosphorylation for mechanotransduction in neonatal cardiac myocytes. FEBS Lett. 2007 Sep. 4; 581(22):4241-7.

Shimizu T, Yamato M, Kikuchi A and Okano T. Cell sheet engineering for myocardial tissue reconstruction. Biomaterials. 2003 June; 24(13):2309-16. Review.

Shimatsu A, Rotwein P. Mosaic evolution of the insulin-like growth factors. Organization, sequence, and expression of the rat insulin-like growth factor I gene. J Biol Chem. 1987 Jun. 5; 262(16):7894-900.

Shive M. S., J. M. Anderson. Biodegradation and biocompatibility of PLA and PLGA microspheres. Adv Drug Del Rev. 28 (1997) 5-24.

Shyy J Y, Chien S. Role of integrins in endothelial mechanosensing of shear stress. Circ Res. 2002 Nov. 1; 91(9):769-75.

Shyy J Y, Chien S, Role of integrins in endothelial mechanosensing of shear stress. Circ Res. 2002 Nov. 1; 91(9):769-75.

Sharp W W, Simpson D G, Borg T K, Samarel A M, Terracio L. Mechanical forces regulate focal adhesion and costamere assembly in cardiac myocytes. Am J Physiol. 1997; 273:H546-556.

Siegfried J M, Kasprzyk P G, Treston A M, Mulshine J L, Quinn, K A, Cuttitta F. A mitogenic peptide amide encoded within the E peptide domain of the insulin-like growth factorIB prohormone. Proc Natl Acad Sci USA. 1992 Sep. 1; 89(17):8107

Snyder J and T A Desai, Microscale three-dimensional polymeric platforms for in vitro cell culture systems. J Biomater Sci Polym Ed. 2001; 12(8):921-32.

Sommer J R. Comparative anatomy: in praise of a powerful approach to elucidate mechanisms translating cardiac excitation into purposeful contraction. J Mol Cell Cardiol. 1995 January; 27(1):19-35.

Spach M S, Heidlage J F, Dolber P C and Barr R C. Electrophysiological effects of remodeling cardiac gap junctions and cell size: experimental and model studies of normal cardiac growth. Circ Res. 2000; 86:302-11.

Street S F, Lateral transmission of tension in frog myofibers: a myofibrillar network and transverse cytoskeletal connections are possible transmitters. J Cell Physiol. 1983 March; 114(3):346-64.

Streeter D D. Gross morphology and fiber geometry of the heart. Washington, D.C.: American Physiological Society; 1979. 61-112

Sung H J, Su J, Berglund J D, Russ B V, Meredith J C, Galis Z S The use of temperature-composition combinatorial libraries to study the effects of biodegradable polymer blend surfaces on vascular cells. Biomaterials. 2005 August; 26(22): 4557-67.

Tao, S L and T A Desai. Gastrointesinal patch systems for oral drug delivery. Drug Discov Today. 2005 Jul. 1; 10(13): 909-15.

Torsoni A S, Marin T M, Velloso L A, Franchini K G. RhoA/ROCK signaling is critical to FAK activation by cyclic stretch in cardiac myocytes. Am J Physiol Heart Circ Physiol. 2005; 289:H1488-1496.

Tracy M A, K L Ward, L Firouzabadian, Y Wang, N Dong, R Qian and Y Zhang, Factors affecting the degradation rate of poly(lactide-co-glycolide) microspheres in vivo and in vitro, Biomaterials 20 (1999), pp. 1057-1062.

Ungaroa F, M. Biondia, I d'Angeloa, L Indolfia, F Quaglia, P A Netti and M I La Rotondaa. Microsphereintegrated collagen scaffolds for tissue engineering: Effect of microsphere formulation and scaffold properties on protein release kinetics. Journal of Controlled Release. 113, 2006, Pages 128-136.

Vetter U, Zapf J, Heit W, Helbing G, Heinze E, Froesch E R, Teller W M. Human fetal and adult chondrocytes. Effect of insulinlike growth factors I and II, insulin, and growth hormone on clonal growth. J Clin Invest. 1986 June; 77(6):1903-8.

von Oepen, R and W Michaeli. Injection Moulding of Biodegradable Implants. Clinical Materials. 10:21-28, (1992).

Wang N, Ingber D E. Control of cytoskeletal mechanics by extracellular matrix, cell shape, and mechanical tension. Biophys J. 1994; 66:2181-2189.

Wang N, Butler J P, Ingber D E. Mechanotransduction across the cell surface and through the cytoskeleton. Science. 1993; 260:1124-1127.

Wilson, C G, L J Bonassar and S S Kohles. Modeling the dynamic composition of engineered cartilage. ABB. 408: 246-254, 2002.

Welch S, Plank D, Witt S, Glascock B, Schaefer E, Chimenti S, Andreoli A M, Limana F, Leri A, Kajstura J, Anversa P, Sussman M A. Cardiac-specific IGF-1 expression attenuates dilated cardiomyopathy in tropomodulin-overexpressing transgenic mice. Circ Res. 2002 Apr. 5; 90(6):641-8.

Westfall M V, Samuelson L C, Metzger J M. Troponin I isoform expression is developmentally regulated in differentiating embryonic stem cell-derived cardiac myocytes. Dev Dyn. 1996

Wobus A M, Guan K, Yang H T, Boheler K R. Embryonic stem cells as a model to study cardiac, skeletal muscle, and vascular smooth muscle cell differentiation. Methods Mol. Biol. 2002; 185:127-56.

Wobus A M and Boheler K R: Embryonic stem cells—Prospects for developmental biology and cell therapy. Physiol Rev. 2005; 85(2):635-678.

Yang S, Alnaqueeb M, Simpson H, Goldspink G. Cloning and characterization of an IGF-1 isoform expressed in skeletal muscle subjected to stretch. J Muscle Res Cell Motil. 1996 August; 17(4):487-95.

Yang S Y, Goldspink G. Different roles of the IGF-I Ec peptide (MGF) and mature IGF-I in myoblast proliferation and differentiation. FEBS Lett. 2002 Jul. 3; 522(1-3):156-60.

Zampino M, Yuzhakova M A, Hansen J C, McKinney R M, Goldspink P H, Geenen D L, Buttrick P M. Sex-related dimorphic response of HIF-1 alpha expression in myocardial ischemia. Am J Physiol Heart Circ Physiol. 2006 August; 291(2):H957-64.

Zimmermann W H, Schneiderbanger K, Schubert P, Didie M, Munzel F, Heubach J F, Kostin S, Neuhuber W L, Eschenhagen T. Tissue engineering of a differentiated cardiac muscle construct. Circ Res. 2002 Feb. 8; 90(2):223-30.

Zimmermann W H, Didie M, Doker S, Melnychenko I, Naito H, Rogge C, Tiburcy M, Eschenhagen T. Heart muscle engineering: an update on cardiac muscle replacement therapy. Cardiovasc Res. 2006 Aug. 1; 71(3):419-29. Epub 2006 Apr. 7.

We claim:

1. A scaffold comprising microrods and optionally a carrier, wherein the microrods have a stiffness ranging from about 1 kPa to about 1 GPa, and wherein the microrods have a rod shape having dimensions of A×B×L, wherein A is 1-30 μm, B is 1-30 μm, and L is 50-120 μm.

2. The scaffold according to claim 1 wherein the carrier is a matrix.

3. The scaffold according to claim 2 wherein said matrix is selected from the group consisting of collagen, gelatin, gluten, elastin, albumin, chitin, hyaluronic acid, cellulose, dextran, pectin, heparin, agarose, fibrin, alginate, carboxymethylcellulose, a hydrogel formed by a solubilized basement membrane preparation extracted from the Engelbreth-Holm-Swarm (EHS) mouse sarcoma, hydrogel and organogel.

4. The scaffold according to claim 1 wherein said microrods modulate the local microenvironment of a cell.

5. The scaffold according to claim 1 wherein said microrods alter cellular cytoskeletal architecture.

6. The scaffold according to claim 1 wherein said microrods alter cellular proliferation.

7. The scaffold according to claim 1 wherein said microrods are biodegradable.

8. The scaffold according to claim 1 wherein said microrods regulate cellular organization, structure, phenotype or function.

9. The scaffold according to claim 1 wherein said carrier is aqueous.

10. The scaffold according to claim 1 wherein said carrier is saline.

11. The scaffold according to claim 1 wherein said carrier is a buffer.

12. The scaffold according to claim 1 wherein said microrods are synthesized from one or more polymers.

13. The scaffold according to claim 1 wherein said microrods are synthesized from one or more copolymers.

14. The scaffold according to claim 12 wherein said polymer is selected from the group consisting of polylactic acid (PLA), polyglycolic acid (PGA), poly(ϵ-caprolactone) (PCL), poly(ethylene glycol) diacrylate (PEGDA), poly(ethylene glycol) dimethacrylate (PEGDMA), and SU-8.

15. The scaffold according to claim 13 wherein said copolymer is selected from the group consisting of poly(lactide-co-glycolide) (PLGA) and poly(DL-lactide-co-ϵ-caprolactone) (DLPLCL).

16. The scaffold according to claim 1 wherein said microrods are porous.

17. The scaffold according to claim 1 wherein said microrods have a shape of a regular polyhedron.

18. The scaffold according to claim 1 wherein said microrods have the shape of an irregular polyhedron.

19. The scaffold according to claim 1 wherein said microrods have a textured surface.

20. The scaffold according to claim 1 wherein said microrods are porous and have a textured surface.

21. The scaffold according to claim 1 wherein said microrods are associated with a biomolecule.

22. The scaffold according to claim 21 wherein said biomolecule is a an insulin-like growth factor (IGF) protein.

23. The scaffold according to claim 21 wherein said biomolecule is an E-domain peptide of an IGF protein.

24. The scaffold according to claim 21 wherein said biomolecule is an Ea, Eb, or Ec domain peptide of an IGF protein.

25. The scaffold according to claim 21 wherein said biomolecule is mechano-growth factor (MGF).

26. The scaffold according to claim 21 wherein said biomolecule is an E-domain peptide of mechano-growth factor (MGF).

27. The scaffold according to claim 26 wherein said MGF E-domain peptide is stabilized.

28. The scaffold according to claim 26 wherein said MGF E-domain peptide is native.

29. The scaffold according to claim 21 wherein said biomolecule is a biologically active fragment of mechano-growth factor (MGF).

30. The scaffold according to claim 21 wherein said biomolecule is elutable from the microrod.

31. The scaffold according to claim 1 wherein said microrods are associated with a targeting molecule that interacts with target cells expressing a binding partner for said targeting molecule.

32. The scaffold according to claim 1 which is an injectable composition.

33. The scaffold according to claim 1 which is surgically implantable.

34. The scaffold according to claim 1 wherein A is 15 μm, B is 15 μm, and L is 100 μm.

35. The scaffold according to claim 1 wherein the microrods have a stiffness ranging from 20 kPa to 100 kPa.

* * * * *